US011053498B2

(12) United States Patent
Kordasiewicz

(10) Patent No.: US 11,053,498 B2
(45) **Date of Patent: *Jul. 6, 2021**

(54) COMPOUNDS AND METHODS FOR REDUCING TAU EXPRESSION

(71) Applicant: Biogen MA Inc., Cambridge, MA (US)

(72) Inventor: Holly Kordasiewicz, San Diego, CA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/527,574

(22) Filed: Jul. 31, 2019

(65) Prior Publication Data

US 2020/0199589 A1 Jun. 25, 2020

Related U.S. Application Data

(63) Continuation of application No. 15/721,366, filed on Sep. 29, 2017, now Pat. No. 10,407,680.

(60) Provisional application No. 62/450,469, filed on Jan. 25, 2017, provisional application No. 62/401,723, filed on Sep. 29, 2016.

(51) Int. Cl.

| | |
|---|---|
| ***C07H 21/04*** | (2006.01) |
| ***C12N 15/113*** | (2010.01) |
| ***A61K 9/00*** | (2006.01) |
| ***A61P 25/14*** | (2006.01) |
| ***A61P 25/28*** | (2006.01) |
| ***A61P 25/08*** | (2006.01) |
| ***A61K 31/7125*** | (2006.01) |
| *A61K 47/02* | (2006.01) |
| *A61K 47/46* | (2006.01) |

(52) U.S. Cl.

CPC .......... *C12N 15/113* (2013.01); *A61K 9/0019* (2013.01); *A61K 31/7125* (2013.01); *A61P 25/08* (2018.01); *A61P 25/14* (2018.01); *A61P 25/28* (2018.01); *A61K 47/02* (2013.01); *A61K 47/46* (2013.01); *C12N 2310/11* (2013.01); *C12N 2310/31* (2013.01); *C12N 2310/315* (2013.01); *C12N 2310/322* (2013.01); *C12N 2310/3341* (2013.01); *C12N 2310/341* (2013.01); *C12N 2310/345* (2013.01); *C12N 2310/3525* (2013.01)

(58) Field of Classification Search

CPC .................................................... C12N 15/113

See application file for complete search history.

(56) References Cited

U.S. PATENT DOCUMENTS

| | | | |
|---|---|---|---|
| 3,687,808 | A | 8/1972 | Merigan et al. |
| 4,845,205 | A | 7/1989 | Huynh Dinh et al. |
| 4,880,635 | A | 11/1989 | Janoff et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 5,034,506 | A | 7/1991 | Summerton et al. |
| 5,130,302 | A | 7/1992 | Spielvogel et al. |
| 5,134,066 | A | 7/1992 | Rogers et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,185,444 | A | 2/1993 | Summerton et al. |
| 5,367,066 | A | 11/1994 | Urdea et al. |
| 5,432,272 | A | 7/1995 | Benner |
| 5,434,257 | A | 7/1995 | Matteucci et al. |
| 5,457,187 | A | 10/1995 | Gmelner et al. |
| 5,459,255 | A | 10/1995 | Cook et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,540 | A | 9/1996 | Haralambidis |
| 5,587,469 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,645,985 | A | 7/1997 | Froehler et al. |
| 5,681,941 | A | 10/1997 | Cook et al. |

(Continued)

FOREIGN PATENT DOCUMENTS

| | | |
|---|---|---|
| CN | 1696294 | 11/2005 |
| CN | 105264091 | 1/2016 |

(Continued)

OTHER PUBLICATIONS

U.S. Appl. No. 14/387,853, U.S. Pat. No. 10,273,474, filed Sep. 25, 2014, Miller.

(Continued)

*Primary Examiner* — Kimberly Chong

(74) *Attorney, Agent, or Firm* — Fish & Richardson P.C.

(57) ABSTRACT

Provided are compounds, methods, and pharmaceutical compositions for reducing the amount or activity of Tau mRNA in a cell or animal, and in certain instances reducing the amount of Tau protein in a cell or animal. Such compounds, methods, and pharmaceutical compositions are useful to ameliorate at least one symptom of a neurodegenerative disease. Such symptoms include loss of memory, loss of motor function, and increase in the number and/or volume of neurofibrillary inclusions. Such neurodegenerative diseases include tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome.

38 Claims, No Drawings

Specification includes a Sequence Listing.

(56) References Cited

U.S. PATENT DOCUMENTS

| | | | |
|---|---|---|---|
| 5,698,685 | A | 12/1997 | Summerton et al. |
| 5,750,692 | A | 5/1998 | Cook et al. |
| 5,763,588 | A | 6/1998 | Matteucci et al. |
| 5,801,154 | A | 9/1998 | Baracchini et al. |
| 5,808,027 | A | 9/1998 | Cook et al. |
| 5,811,534 | A | 9/1998 | Cook et al. |
| 5,830,653 | A | 11/1998 | Froehler et al. |
| 5,837,853 | A | 11/1998 | Takashima et al. |
| 5,859,221 | A | 1/1999 | Cook et al. |
| 5,948,903 | A | 9/1999 | Cook et al. |
| 6,005,096 | A | 12/1999 | Matteucci et al. |
| 6,166,199 | A | 12/2000 | Cook et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,670,461 | B1 | 12/2003 | Wengel et al. |
| 6,673,661 | B1 | 1/2004 | Liu et al. |
| 6,770,748 | B2 | 8/2004 | Imanishi et al. |
| 6,794,499 | B2 | 9/2004 | Wegel et al. |
| 7,034,133 | B2 | 4/2006 | Wengel et al. |
| 7,053,207 | B2 | 5/2006 | Wengel |
| 7,084,125 | B2 | 8/2006 | Wengel |
| 7,217,805 | B2 | 5/2007 | Imanishi et al. |
| 7,314,923 | B2 | 1/2008 | Kaneko et al. |
| 7,399,845 | B2 | 7/2008 | Seth et al. |
| 7,427,672 | B2 | 9/2008 | Imanishi et al. |
| 7,547,684 | B2 | 6/2009 | Seth et al. |
| 7,569,575 | B2 | 8/2009 | Sorensen et al. |
| 7,569,686 | B1 | 8/2009 | Bhat et al. |
| 7,696,345 | B2 | 4/2010 | Allerson et al. |
| 7,741,457 | B2 | 6/2010 | Seth et al. |
| 7,750,131 | B2 | 7/2010 | Woldike et al. |
| 7,858,747 | B2 | 12/2010 | Woldike et al. |
| 7,875,733 | B2 | 1/2011 | Bhat et al. |
| 7,939,677 | B2 | 5/2011 | Bhat et al. |
| 8,022,193 | B2 | 9/2011 | Swayze et al. |
| 8,030,467 | B2 | 10/2011 | Seth et al. |
| 8,034,909 | B2 | 10/2011 | Wengel et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,124,745 | B2 | 2/2012 | Allerson et al. |
| 8,153,365 | B2 | 4/2012 | Wengel et al. |
| 8,178,503 | B2 | 5/2012 | Rigoutsos et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,329,890 | B2 | 12/2012 | Davidson et al. |
| 8,440,803 | B2 | 5/2013 | Swayze et al. |
| 8,501,805 | B2 | 8/2013 | Seth et al. |
| 8,530,640 | B2 | 9/2013 | Seth et al. |
| 8,546,556 | B2 | 10/2013 | Seth et al. |
| RE44,779 | E | 2/2014 | Imanishi et al. |
| 8,796,437 | B2 | 8/2014 | Swayze et al. |
| 8,871,729 | B2 | 10/2014 | Yague et al. |
| 9,005,906 | B2 | 4/2015 | Swayze et al. |
| 9,012,421 | B2 | 4/2015 | Migawa et al. |
| 9,084,813 | B2 | 7/2015 | Roberson et al. |
| 9,198,982 | B2 | 12/2015 | Roberson et al. |
| 9,644,207 | B2 | 5/2017 | Rigo et al. |
| 9,683,235 | B2 | 6/2017 | Freier |
| 1,027,347 | A1 | 4/2019 | Miller et al. |
| 10,793,856 | B2 | 10/2020 | Kordasiewicz |
| 2001/0053519 | A1 | 12/2001 | Fodor et al. |
| 2002/0018995 | A1 | 2/2002 | Ghetti et al. |
| 2003/0158403 | A1 | 8/2003 | Manoharan et al. |
| 2003/0175906 | A1 | 9/2003 | Manoharan et al. |
| 2003/0219770 | A1 | 11/2003 | Eshleman et al. |
| 2003/0228597 | A1 | 12/2003 | Cowsert et al. |
| 2004/0054156 | A1 | 3/2004 | Draper et al. |
| 2004/0171570 | A1 | 9/2004 | Allerson et al. |
| 2004/0241651 | A1 | 12/2004 | Olek et al. |
| 2005/0108783 | A1 | 5/2005 | Koike et al. |
| 2005/0130923 | A1 | 6/2005 | Bhat et al. |
| 2005/0153336 | A1 | 7/2005 | Bennett et al. |
| 2005/0244851 | A1 | 11/2005 | Blume et al. |
| 2005/0255487 | A1 | 11/2005 | Khvorova et al. |
| 2006/0216722 | A1 | 9/2006 | Betsholtz et al. |
| 2007/0031844 | A1 | 2/2007 | Khvorova et al. |
| 2007/0203333 | A1 | 8/2007 | McSwiggen et al. |
| 2007/0287831 | A1 | 12/2007 | Seth et al. |
| 2008/0003570 | A1 | 1/2008 | Rogers et al. |
| 2008/0039618 | A1 | 2/2008 | Allerson et al. |
| 2008/0249058 | A1 | 10/2008 | Roberson et al. |
| 2008/0318210 | A1 | 12/2008 | Bentwich |
| 2009/0012281 | A1 | 1/2009 | Swayze et al. |
| 2009/0076725 | A1 | 3/2009 | Bhogal et al. |
| 2009/0162365 | A1 | 6/2009 | Feinstein |
| 2009/0176728 | A1 | 7/2009 | Yague et al. |
| 2010/0261175 | A1 | 10/2010 | Rasmussen et al. |
| 2011/0041191 | A1 | 2/2011 | Platt et al. |
| 2011/0054005 | A1 | 3/2011 | Naito et al. |
| 2011/0150897 | A1 | 6/2011 | Meyer et al. |
| 2011/0244561 | A1 | 10/2011 | Davidson et al. |
| 2011/0263687 | A1 | 10/2011 | Mattick et al. |
| 2013/0046007 | A1 | 2/2013 | Bennett |
| 2013/0123133 | A1 | 5/2013 | Ward et al. |
| 2013/0130378 | A1 | 5/2013 | Manoharan et al. |
| 2013/0203836 | A1 | 8/2013 | Rajeev et al. |
| 2014/0155462 | A1 | 6/2014 | Brown et al. |
| 2014/0315983 | A1 | 10/2014 | Brown et al. |
| 2015/0057329 | A1 | 2/2015 | Bhanot et al. |
| 2015/0191727 | A1 | 7/2015 | Migawa et al. |
| 2015/0275205 | A1 | 10/2015 | Miller et al. |
| 2016/0032285 | A1 | 2/2016 | Rigo et al. |
| 2016/0145617 | A1 | 5/2016 | Kordasiewicz et al. |
| 2017/0211064 | A1 | 7/2017 | Rigo et al. |
| 2018/0051283 | A1 | 2/2018 | Rigo et al. |
| 2018/0094261 | A1 | 4/2018 | Kordasiewicz et al. |
| 2020/0032257 | A1 | 1/2020 | Miller et al. |

FOREIGN PATENT DOCUMENTS

| | | |
|---|---|---|
| JP | 2010525303 | 7/2010 |
| WO | WO9839352 | 9/1998 |
| WO | WO9914226 | 3/1999 |
| WO | WO1999062548 | 12/1999 |
| WO | WO0063364 | 10/2000 |
| WO | WO2001032703 | 5/2001 |
| WO | WO01072765 | 10/2001 |
| WO | WO02081494 | 10/2002 |
| WO | WO03004602 | 1/2003 |
| WO | WO2004017072 | 2/2004 |
| WO | WO2004035765 | 4/2004 |
| WO | WO2004058940 | 7/2004 |
| WO | WO2004011613 | 9/2004 |
| WO | WO2004106356 | 12/2004 |
| WO | WO2005017143 | 2/2005 |
| WO | WO2005021570 | 3/2005 |
| WO | WO2005040180 | 5/2005 |
| WO | WO2006047673 | 5/2006 |
| WO | WO2007027775 | 3/2007 |
| WO | WO2007107789 | 9/2007 |
| WO | WO2007134181 | 11/2007 |
| WO | WO2008101157 | 8/2008 |
| WO | WO2008124066 | 10/2008 |
| WO | WO2008131807 | 11/2008 |
| WO | WO2008150729 | 12/2008 |
| WO | WO2008154401 | 12/2008 |
| WO | WO2009006478 | 1/2009 |
| WO | WO2009067647 | 5/2009 |
| WO | WO2009100320 | 8/2009 |
| WO | WO2010036698 | 4/2010 |
| WO | WO2010148249 | 12/2010 |
| WO | WO2011005786 | 1/2011 |
| WO | WO2011005793 | 1/2011 |
| WO | WO2011017521 | 5/2011 |
| WO | WO2011131693 | 10/2011 |
| WO | WO2011139702 | 11/2011 |
| WO | WO2012005898 | 1/2012 |
| WO | WO2012018881 | 2/2012 |
| WO | WO2012177639 | 12/2012 |
| WO | WO2013148260 | 10/2013 |

(56) References Cited

FOREIGN PATENT DOCUMENTS

| | | |
|---|---|---|
| WO | WO2013173647 | 11/2013 |
| WO | WO2014012081 | 1/2014 |
| WO | WO2014114937 | 7/2014 |
| WO | WO2014153236 | 9/2014 |
| WO | WO2014179620 | 11/2014 |
| WO | WO2015010135 | 1/2015 |
| WO | WO2015106128 | 7/2015 |
| WO | WO2016019063 | 2/2016 |
| WO | WO2016126995 | 8/2016 |
| WO | WO2016127002 | 8/2016 |
| WO | WO2016151523 | 9/2016 |
| WO | WO2017015555 | 1/2017 |
| WO | WO2017109679 | 6/2017 |
| WO | WO2013148283 | 10/2017 |
| WO | WO2018064593 | 4/2018 |

OTHER PUBLICATIONS

U.S. Appl. No. 16/298,607, filed Mar. 11, 2019, Miller.
U.S. Appl. No. 14/906,047, U.S. Pat. No. 9,683,235, filed Jan. 19, 2016, Kordasiewicz.
U.S. Appl. No. 15/593,173, filed May 11, 2017, Kordasiewicz.
U.S. Appl. No. 16/336,443, filed Mar. 25, 2019, Kordasiewicz.
U.S. Appl. No. 15/721,366, U.S. Pat. No. 10,407,680, filed Sep. 29, 2017, Kordasiewicz.
U.S. Appl. No. 60/130,377, filed Apr. 21, 1999, Pachuk et al.
U.S. Appl. No. 60/399,998, filed Jul. 31, 2002, Pachuk et al.
U.S. Appl. No. 60/419,532, filed Oct. 18, 2002, Pachuk et al.
Agrawal, S. et al., Proc. Natl. Acad. Sci. USA 87, 1401-1405 (1990).
Albaek et al., J. Org. Chem., 2006, 71, 7731-7740.
Allshire, 2002, Science 297, 1818-1819.
Altmann et al., Biochem. Soc. Trans., 1996, 24, 630-637.
Altmann et al., Chimia, 1996, 50, 168-176.
Altmann et al., Nucleosides Nucleotides, 1997, 16, 917-926.
Altschul et al., J. Mol. Biol., 1990, 215, 403-410.
Andorfer et al., "Hyper phosphorylation and aggregation of tau in mice expressing normal human tau isoforms" Journal of Neurochemistry (2003) 86: 582-590.
Australian Patent Examination Report for Application No. 2013202595 dated Jul. 4, 2014 (15 pages).
Australian Patent Examination Report for Application No. 2013202595, dated Mar. 17, 2016, 3 pages.
Australian Patent Examination Report for Application No. 2016202220, dated Jan. 12, 2017, 4 pages.
Badiola et al., "Tau phosphorylation and aggregation as a therapeutic target in Tauopathies," CNS Neurol. Disord. Drug Targets, Dec. 2010, vol. 9, No. 6, pp. 727-740.
Baker et al., J. Biol. Chem., 1997, 272, 11944-12000.
Baker, C. et al., Nucleic Acids Res. 18, 3537-3543 (1990).
Bevins, R.A. and Besheer, J., J. Nature Protocols, Jan. 2006: 1306-1311.
Bi et al., Tau-Targeted Immunization Impedes Progression of Neurofibrillary Histopathology in Aged P30 IL Tau Transgenic Mice Plos One (2011) 6(12):e26860.
Boiziau et al., "Antisense 2-0-alkyl oligo ribonucleotides are efficient inhibitors of reverse transcription", Nucleic Acids Research, 1995, 23(1):64-71.
Braasch et al., "Novel antisense and peptide nucleic acid strategies for controlling gene expression" Biochemistry (2002) 41(14):4503-4510.
Braasch et al., Chem. Biol., Aug. 1-7, 2001.
Branch et al., "A good antisense molecule is hard to find," TIBS (1998) 23:45-50.
Buck et al., "Design strategies and performance of custom DNA sequencing primers", Bio techniques, 1999, 27(3):528-536.
Caceres et al "Inhibition of neurite polarity by tau antisense oligonucleotides in primary cerebellar neurons" Nature (1990) 343:461-463.
Caceres et al., "The Effect of Tau antisense Oligonucleotides on Neurite Formation of Cultured Cerebellar Macro neurons" J. Neuroscience (1991) 11(6):1515-1523.
Canadian Patent Office Action for Application No. 2866392, dated Feb. 5, 2018, 6 pages.
Chernolovskaya et al., "Chemical modification of siRNA", Current Opinion in Molecular Therapeutics, 2010, 12(2):1-10.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
ClinicalTrials.gov, "Safety, Tolerability, Pharmacokinetics, and Pharmacodynamics of Ionis-Maptrx in patients with mild Alzheimer's Disease", NCT03186989 online Jun. 14, 2017.
Craig et al., "Towards a small molecule inhibitor of tau exon 10 splicing: Identification of compounds that stabilize the 5'-splice site stem-loop" Alzheimer's & Dementia: The Journal of the Alzheimer's Association (2012) 8(4): p. 636.
Crooke et al., "Antisense Drug Technology", Second Edition, CRC Press, 2008, Chapters 1-28.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277(2):923-937.
Davies et al., "Hyper phosphorylation and aggregation of tau in mice expressing normal human tau isoforms", Journal of Neurochemistry, 2003, 86:582-590.
Dawson, "Tau Exon 10 Splicing Tauopathy", presentation given at CurePSP 2010 International Research Symposium, Nov. 18, 2010, San Diego, CA, 39 pages.
Dawson, "The Effects of the CBD-Associated Tau Gene H1 Haplotype on Tau Expression," Abstract presented at CurePSP 2010 International Research Symposium, Nov. 18, 2010, San Diego, CA (retrieved online Jan. 13, 2016).
Dawson, H.N. et al., J. Neurosci. 27: 9155-9168, 2007.
Deacon, R. M., Nat. Protocol. 2006, 1:1117-9.
DeVos et al., "Antisense oligonucleotides: treating neurodegeneration at the level of RNA" Neurotherapeutics (2013) 10(3): 486-497.
DeVos et al., "Antisense Reduction of Human Tau in the CNS of P301S mice both Prevents and Reverses Hyper phosphorylated Tau Deposition" abstract presented at Keystone Symposium: Long Noncoding RNAs: Marching toward Mechanism, Feb. 27-Mar. 4, 2014, Santa Fe, NM, 1 page.
DeVos et al., "Antisense Reduction of Tau in Adult Mice Protects against Seizures" J. Neuroscience (2013) 33(31): 12887-12897.
DeVos et al., "Antisense Reduction of the Human Tau Transgene in the CNS of P301S mice Robustly Decreases Tau Deposition" abstract presented at Keystone Symposia: New Frontiers in Feb. 3-8, 2013, Santa Fe, NM, 1 page.
DeVos et al., "Reducing Human Tau in the CNA of P301S mice Dramatically Reverses Tau Pathology" abstract presented at 14th International Conference on Alzheimer's Drug Discovery, Sep. 9-10, 2013, Jersey City, NJ, 1 page.
DeVos et al., "Tau reduction prevents neuronal loss and reverses pathological tau deposition and seeding in mice with Tauopathy", Science Translational Medicine, 2017, 9(374):1-14.
DeVos et al., "Using antisense oligonucleotides to knockdown endogenous brain tau in vivo" Alzheimer's & Dementia: The Journal of the Alzheimer's Association (2012) 8(4): p. 205.
DeVos et al., "Using antisense oligonucleotides to knockdown endogenous brain tau in vivo" poster presentation at AAIC 2012; Jul. 14-19, 2012, 1 page.
Donahue et al., "Stabilization of the Tau Exon 10 Stem Loop Alters Pre-mRNA Splicing" J. Biol. Chem. (2006) 281(33):23302-23306.
Duff et al., "Characterization of Pathologyin Transgenic Mice Over Expression Human Genomic and cDNA Tau Transgenes", Neurobiology of Disease, 2000, 7:87-98.
Elayadi et al., Curr. Opinion Inves. Drugs, Feb. 2001, 558-561.
Englisch et al., "Chemically Modified Oligonucleotides as Probes and Inhibitors" Angewandte Chemie, International Edition (1991) 30(6): 613-629.

(56) References Cited

OTHER PUBLICATIONS

European Patent Office Action for Application No. 13770075.3 dated Aug. 16, 2018, 8 pages.
European Patent Office Action for Application No. 13770075.3 dated Feb. 8, 2018, 5 pages.
Extended European Search Report for Application No. 13770075.3 dated Oct. 2, 2015, 8 pages.
Extended European Search Report for Application No. 14767904.7, dated Sep. 19, 2016, 10 pages.
Freier et al., Nucleic Acids Research, 1997, 25(22), 4429-4443.
Frieden et al., Nucleic Acids Research, 2003, 21, 6365-6372.
Frost, S. Digital Telerential Screen, 2012, 91-100.
Furdon, P. et al., Nucleic Acids Res. 17, 9193-9204 (1989).
Gautschi et al., J. Natl. Cancer Inst., 93:463-471, 2001.
GenBank Accession No. AK226139.1 (2007), 3 pages.
GenBank Accession No. NM_001123066.3 (2015), 6 pages.
GenBank Accession No. NM_001123067.3 (2015), 5 pages.
GenBank Accession No. NM_001203251.1 (2015), 5 pages.
GenBank Accession No. NM_001203252.1 (2015), 6 pages.
GenBank Accession No. NM_001285455.1, 2013, 4 pages.
GenBank Accession No. NM_005910.5 (2015), 6 pages.
GenBank Accession No. NM_016834.4 (2015), 4 pages.
GenBank Accession No. NM_016835.4 (2015), 19 pages.
GenBank Accession NT_010783.15 (2013), 5 pages.
GenBank Accession NT010783 (2008), 7 pages.
GenBank Accession No. NM_16841.4 (2015), 3 pages.
Goedert et al., "Cloning and Sequencing of the cDNA Encoding a Core Protein of the Paired Helical Filament of Alzheimer's Disease: Identification as the Microtubule-Associated Protein Tau" PNAS (1988) 85(11):4051-4055.
Goedert, M. et al., Neurosci. Lett. 1995, 167-9.
Gordon et al., "Antisense suppression of tau in cultured ray oligodendrocytes inhibits process formation", Journal of Neuroscience Research, May 2008, 86(12):2591-2601.
Gupta, N. et al., Can. J. Ophthalmol 2008, 43:53-60.
Hall et al., 2002, Science, 297, 2232-2237.
Hatta et al., "Mechanisms of the inhibition of reverse transcription by unmodified and modified antisense oligonucleotides", 1993, 330(2):161-164.
Ho, W. L. et al., Molecular Vision, 2012, 18:2700-2710.
International Search Report and Written Opinion for Application No. PCT/US2013/31500 dated Jun. 5, 2013 (12 pages).
International Search Report and Written Opinion for Application No. PCT/US2014/047486, dated Feb. 9, 2015, 12 pages.
International Search Report and Written Opinion for Application No. PCT/US2015/042740, dated Dec. 15, 2015, 13 pages.
International Search Report and Written Opinion for Application No. PCT/US2015/042740, dated Feb. 4, 2016, 13 pages.
International Search Report for application PCT/US2014/029752 dated Sep. 18, 2014, 10 pages.
International Search Report for Application PCT/US2017/054540 dated Jan. 18, 2018, 11 pages.
Japanese Patent Office Action for Application No. 2015503306, dated Jun. 12, 2018, 13 pages with English Translation.
Japanese Patent Office Action for Application No. 2015503306, dated Nov. 22, 2016, 5 pages with English Translation.
Jenuwein, 2002, Science, 297, 2215-2218.
Jiang et al., "Aberrant Splicing of tau Pre-mRNA Caused by Intronic Mutations Associated with the Inherited Dementia Frontotemporal Dementia with Parkinsonism Linked to Chromosome 17" Mol. Cell Biol. (2000) 20(11):4036-4048.
Jones et al., "Targeting hyper phosphorylated tau with sodium selenate suppresses seizures in rodent models" Neurobiology of Disease (2012) 897-901.
Jones, L.J. et al., Analytical Biochemistry, 1998, 265, 368-374.
Kabanov et al., "A new class of antivirals: antisense oligonucleotides combined with a hydrophobic substituent effectively inhibit influenza vims reproduction and synthesis of vims-specific proteins in MDCK cells" FEBS Lett. (1990) 259:327-330.
Kalbfuss, B. et al., "Correction of Alternative Splicing of Tau in Frontotemporal Dementia and Parkinsonism Linked to Chromosome 17," Journal of Biological Chemistry, 2001, vol. 276, pp. 42986-42993.
Koshkin et al., Tetrahedron, 1998, 54, 3607-3630.
Kroschwitz, The Concise Encyclopedia of Polymer Science and Engineering, John Wiley & Sons, 1990, 858-859.
Kumar et al., Bioorg. Med. Chem. Lett., Aug. 1998, 2219-2222.
Lane et al., "Discovery and early clinical development of Ionis-Maptrx, The first tau-lowering antisense oligonucleotide, in patients with mild AD", abstract presented at the Alzheimer's Association International Conference, Jul. 2017, London, England.
Letsinger et al., "Cholesteryl-conjugated oligonucleotides: Synthesis, properties, and activity as inhibitors of replication of human immunodeficiency vims in cell culture" PNAS (1989) 86:6553-6556.
Leumann, J. C., Bioorganic & Medicinal Chemistry, Oct. 2002, 841-854.
Maher and Dolnick, Nuc. Acid. Res. 16:3341-3358, 1988.
Manoharan et al., "Chemical Modifications to Improve Uptake and Bioavailability of Antisense Oligonucleotides" Ann. N.Y. Acad. Sci. (1992) 660:306.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids", Tetrahedron Lett., 1995, 36(21):3651-3564.
Martin, P., Helv. Chim. Acta, 1995, 78, 486-504.
Mishra et al., "Improved leishmanicidal effect of phosphorotioate antisense oligonucleotides by LDL-mediated delivery" Biochim. Biophys. Acta (1995) 1264:229-237.
Morita et al., Bioorganic Medicinal Chemistry, Nov. 2003, 2211-2226.
New-England Biolabs 1998/99 Catalog (cover page and pp. 121 and 284), 3 pages.
Nishina et al., "Chimeric antisense oligonucleotide conjugated to alpha-tocopherol", Molecular Therapy Nucleic Acids, 2015, 4:e220.
Nishina et al., "Efficient in vivo delivery of siRNA to the liver by conjugation of alpha-tocopherol", Molecular Therapy, 2008, 16(4):734-740.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Oka et al., "An Oxazaphospholidine approach for the steroid controlled synthesis of oligonucleotide phosphorothioates", J. Am. Chem. Soc., 2003, 125:8307-8317.
Orum et al., Curr. Opinion Mol. Ther., Mar. 2001, 239-243.
Pal-Bhadra et al., 2004, Science, 303, 669-672.
Peacey et al., "Targeting a pre-mRNA structure with bipartite antisense molecules modulates tau alternative splicing" Nucleic Acids Research (2012) 40(19):9836-9849.
Pizzi et al., "Antisense Strategy Unravels Tau Proteins as Molecular Risk Factors for Glutamate-Induced Neurodegeneration" Cellular and Molecular Neurobiology (1994) 14(5):569-578.
Reynolds et al., "Rational siRNA design for RNA interference" Nature Biotechnology (2004) 22(3):326-330.
Rodriguez-Martin, T. et al., Reprograming of tau alternative splicing by spliceosome-mediated RNA trans-splicing: Implications for Tauopathies, Proceedings of the National Academy of Sciences, 2005, Vo. 102, No. 43, pp. 15659-15664.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi et al., "Heterocyclic Base Modifications in Nucleic Acids and Their Applications in Antisense Oligonucleotides" Antisense Research and Applications (1993) pp. 273-288.

(56) References Cited

OTHER PUBLICATIONS

Sapir et al., "Tau's role in the developing brain: implications for intellectual disability" Human Molecular Genetics (2012) 21(8):1681-1692.
Sazani et al., "Therapeutic potential of antisense oligonucleotides as modulators of alternative splicing", J. Clinical Invest, 2003, 112:491-486.
Schoch et al., "Antisense oligonucleotide-mediated tau splicing reduces behavioral deficits and tau pathology in a Tauopathy model" abstract presented at Keystone Symposium: Alzheimer's Disease, Mar. 2-7, 2014, Keystone, CO.
Schoch et al., "Antisense oligonucleotide-mediated tau splicing reduces behavioral deficits and tau pathology in a Tauopathy model" poster presented at Keystone Symposium: Alzheimer's Disease, Mar. 2-7, 2014, Keystone, CO.
Shea et al., "Synthesis, hybridization properties and antiviral activity of lipid-oligodeoxynucleotide conjugates" Nucl. Acids Res. (1990) 18(13):3777-3783.
Singh et al., Chem. Commun., Apr. 1998, 455-456.
Singh et al., J. Org. Chem., 1998, 63, 10035-10039.
Smith and Waterman, Adv. Appl. Math., Feb. 1981, 482-489.
Spicakova et al., "Expression and silencing of the Microtubule-Associated Protein Tau in breast cancer cells", Molecular Cancer Therapeutics, Nov. 2010, 9(11):2970-2981.
Sproat, B. et al., Nucleic Acids Res. 17, 3373-3386 (1989).
Srivastava et al., J. Am. Chem. Soc., 2007, 129(26), 8362-8379.
Svinarchuk et al., "Inhibition of HIV proliferation in MT-4 cells by antisense oligonucleotide conjugated to lipophilic groups" Biochemie (1993) 75:49-54.
Usman et al., "Exploiting the chemical synthesis of RNA", Trends in Biochemical Sciences, Sep. 1992, 17(9):334-339.
Verdel et al., 2004, Science, 303, 672-676.
Volpe et al., 2002, Science, 297, 1833-1837.
Wahlesledt et al., Proc. Natl. Acad. Sci. U.S.A., 2000, 97, 5633-5638.
Walder, R. and Walder, J., Proc. Natl. Acad. Sci. USA 85, 5011-5015 (1988).
Wan et al., "Synthesis, biophysical properties and biological activity of second generation antisense oligonucleotides containing chiral phosphorothioate linkages", Nucleic Acids Research, 42(22):13456-12468.
Wang et al., "A Novel Tau Transcript in Cultured Human Neuroblastoma Cells Expression Nuclear Tau" J. Cell Biol. (1993) 121(2):257-267.
Wolfe et al., "Tau Mutations in Neurodegenerative Diseases", J. Biol Chem, 2009, 284(10):3021-3025.
Wolfe M.S., "The Roll of Tau in Neurodegenerative Diseases and Its Potential as a Therapeutic Target" Scientifica (2012) 1-20.
Woolf et al., Proc. Natl. Acad. Sci. USA 89:7305-7309, 1992.
Yamada et al., Neurosci. 2011, 31: 13110-117.
Yoshiyama, Y. et al., Neuron 53: 337-351, 2007.
Zhang and Madden, Genome Res., Jul. 1997, 649-656.
Zhou et al., "Fine Tuning of Electrostatics around the Internucleotide Phosphate through Incorporation of Modified 2',4'-Carbocyclic-LNAs and -ENAs Leads to Significant Modulation of Antisense Properties" J. Org. Chem. (2009) 74:118-134.
Bennett et al., "Pharmacological Properties of 2'-O-Methoxyethyl-Modified Oligonucleotides", Antisense Drug Technology: Principles, Strategies and Applications, 2nd Edition, 2007, pp. 273-303.
Prakash, "An overview of sugar-modified oligonucleotides for antisense therapeutics", Chemistry and Biodiversity, Sep. 2011, 8(9):1616-1641.

SEQUENCE LISTING

```
<160> NUMBER OF SEQ ID NOS: 11

<210> SEQ ID NO 1
<211> LENGTH: 137001
<212> TYPE: DNA
<213> ORGANISM: Homo sapiens

<400> SEQUENCE: 1

caaaaattag ccgggagtgg tggcatatgc ctgtaatccc agtagctggg aggctgagac      60

aggaaaatcg cttgaacccg ggaaacaggt tgcagtgagc cgagatcgtg ccactgcact     120

ccagcctggg caacagagcg agactccatc tcaaaaaaac aaaacaaaca cacacaaaaa     180

accaaaaata aataaataaa atgatcactt ctgaatactg atctaactag gggttgcagg     240

gtgggctgat atagggagaa actggagagc aaggagatca ctaaggtccc tacatgtcca     300

gaaccaagat agaggtcttg aactaggatg gtggcagtta gaacaacaac aacaaaaagt     360

caattccagg ctgagtgcag tggctcatgc ttgtaatccc aacgctttgg gaggctgagg     420

tgggagttag aaagcagcct gggcaacact gcaagacctc ctctctaaaa aaaaaaaaaa     480

aaaaaagtta gccaggtgtg gtggtgccca cctgtagtcc cagcaactca gaaggctgag     540

gtgggaagat tgcttgagcc ccaggagttc aagcttgccg tgagctacga ttgtgccact     600

gcactccagc ctgagcaaga ccttgtctcc aaaaaaaggt caattccact gacttttcta     660

aggtgtacac catcaagggg cagctccatc tccaggccat tggctcatga gacattctgt     720

agtcagaagg ctagggcaga ttgctttgag caagccccca tggtggttct cactcctact     780

tctttgggta tatgcccctc tgtttaaaaa taaagttaat atgcatttaa aaaaaaaaag     840

gagaaaaagg tcagttccag aaactgtgtg aataaagcat tttacttgct ttttctatta     900

atctataaca tatgttgatt ttttaaaaag aatataagag ctatgcaaat tggagcttca     960
```

```
agacaacttc ccatctccct aggaggagat ggctgcccta aacccccta catagaaatc    1020
atcccactgc ttgggcttaa acttgatgtt ggggaaatga aaaatccaag ctaaggccga   1080
agcctggggc ctgggcgacc agcagaatga ggaccactgg tcagtttcag gctgaggtgc   1140
gtcttccagg ggacaatctc tagctggccc ttaaacattc agacttcaag ctctatttac   1200
agcataaagg tgtttcaaaa gacgtgatac aaataactgc aaatgctctg cgatgtgtta   1260
agcactgttt gaaattcgtc taatttaaga tttttttttc tgacgtaacg gttagattca   1320
cgtttctttt tttttaagta cagttctact gtattgtaac tgagttagct tgctttaagc   1380
cgatttgtta aggaaaggat tcaccttggt cagtaacaaa aaaggtggga aaaaagcaag   1440
gagaaaggaa gcagcctggg ggaaagagac cttagccagg ggggcggttt cgggactacg   1500
aagggtcggg gcggacggac tcgagggccg gccacgtgga aggccgctca ggacttctgt   1560
aggagaggac accgccccag gctgactgaa agtaaagggc agcggaccca gcggcggagc   1620
cactggcctt gccccgaccc cgcatggccc gaaggaggac acccaccccc acaacgacac   1680
aaagactcca actacaggag gtggagaaag cgcgtgcgcc acggaacgcg cgtgcgcgct   1740
gcggtcagcg ccgcggcctg aggcgtagcg ggagggggac cgcgaaaggg cagcgccgag   1800
aggaacgagc cgggagacgc cggacggccg agcggcaggg cgctcgcgcg cgcccactag   1860
tggccggagg agaaggctcc cgcggaggcc gcgctgcccg cccccctccc tggggaggct   1920
cgcgttcccg ctgctcgcgc ctgcgccgcc cgccggcctc aggaacgcgc cctcttcgcc   1980
ggcgcgcgcc ctcgcagtca ccgccaccca ccagctccgg caccaacagc agcgccgctg   2040
ccaccgccca ccttctgccg ccgccaccac agccaccttc tcctcctccg ctgtcctctc   2100
ccgtcctcgc ctctgtcgac tatcaggtaa gcgccgcggc tccgaaatct gcctcgccgt   2160
ccgcctctgt gcacccctgc gccgccgccc ctcgccctcc ctctccgcag actggggctt   2220
cgtgcgccgg gcatcggtcg gggccaccgc agggcccctc cctgcctccc ctgctcgggg   2280
gctggggcca gggcggcctg gaaagggacc tgagcaaggg atgcacgcac gcgtgagtgc   2340
gcgcgtgtgt gtgtgctgga gggtcttcac caccagattc gcgcagaccc caggtggagg   2400
ctgtgccggc agggtggggc gcggcggcgg tgacttgggg gagggggctg cccttcactc   2460
tcgactgcag ccttttgccg caatgggcgt gtgtgtgtgt gtgtgtgtgt gtgtgtgtgt   2520
gtgtgtgtgt gtggaggggt ccgataacga cccccgaaac cgaatctgaa atccgctgtc   2580
cctgccgctg ttcgccatca gctctaagaa agacgtggat cgggttctag aaaagatgac   2640
tccctgcacg cccctccctg cacctcccga gcagtgattc cgacagggcc ttcactgccc   2700
ctgattttag gcgggggccg gccccctccc cttttcctcc ttcagaaacc cgtaggggac   2760
atttggggc tgggagaaat cgaggagatg gggaggggtc cacgcgctgt cactttagtt   2820
gcccttcccc ctgcgcacgc ctggcacaga gacgcgagca gcgccgtgcc tgagaacagt   2880
gcgcggatcc cactgtgcac gctcgcaaag gcagggttca cctggcctgg cgatgtggac   2940
ggactcggcg gccgctggtc cccgttcgcg ggcacgcaca gccgcagcca cgcacggatg   3000
ggcgcggggc tgcaggtgca tctcggggcg gatttctttc tcagcgctcg gagcgcaggg   3060
cgcccggcgt gtgcgctccc tgccggaggc gcggggctgg cgcgcagggc tcgcccctca   3120
ctgcggcagt gggtgtggac cctggtgggc gaggaagggg gaggataggc tgtgcctcct   3180
cccactcccg cccccagccc cccttttttt ccccctcgga acgcgaggtg ccatcttttt   3240
tcggcgtgtc acgtctttac ggtgccatgc caaaccgggt ggccgggctt cataggacag   3300
ggcggggcct ggcattaaag ggagggggac aatcagcgct gaaatcttgg cgttttgctg   3360
```

```
ctgcgggcgt gagcactggg ggcgttcgcc cagcaccttc ttcgggggct ctttgctttg   3420
tctgtagagg ttacgtgatc tgcgctccca gccctggttt ctggctttta ttctgagggt   3480
gttcagtcaa cctcccccct acgcccatgc gcctctcttt cctttttcgc tcctcatttc   3540
cgagcccatt gttggatctc gaggcttgct gggttcgatg aactcgagtc aacccccccga   3600
cccccggcac gcatggaacg ggcgtgaccg cgcgcagcct cgtctcggag tctgccggcg   3660
ccgggaagct tctgaaggga tgggattcga gtctccgtgc gcgctgcggg cggcggcaga   3720
gggatctcgc ccctccctac accccaagtg tcctgagggc cacgccacac caggttgccc   3780
agcgagggac gctggctacc catccgggga tgggtgggga gccctggcgg ggcctctccg   3840
gctttacgcc ctgttgcttc gcctggccgg agaatgtgag gaaggggcat aaggttactg   3900
gtgcttcggc cacacccatc tttctgagcc cactggactg ggcgcagagg ggggattgcc   3960
atggaaacca caggtgtccg gagaggggat cttggggctg gcctcacccc ttccctgcgg   4020
agattgggga ccctggggta gggggagccg cgcccagtcg gcctcctgga ggacacggga   4080
ggaagccccg aacccccgcg cctgaggctg tttctgattg gcccctggag gccgcagaca   4140
cgcagatagg cggccctggg tgtattttta ttaatattat gtccgtactg attaatatta   4200
tttatcttaa ataaatttca cccgtgtcca agttcaccgc gcccccaaaa ccgagtctgg   4260
ggcggcaggg ggaactcctg gccaacgaat ccatgcctcg ccctcctgtg atgaacctgg   4320
tacgcacggt tttctggtta attctatcgc tgaaaactgg tgcggggggc gcacttctga   4380
gacggaagag catctaggag ctgaatcctc cacgcgggtc gcccaggttg atctgaattt   4440
ctggggaatg gcttggctgc ccgcccggga ccaggccgac cctccttgac ggtggcgtag   4500
agggctggag cctgggtact gcgaggctcc tcgcatggct gggcccgccg cgaggggttg   4560
cagagcggct cagggatcga ttcaagcatc gtctctcctc cctcgccccc agacagagct   4620
gggcgcgggg ttccccttcc agatggagcg agggtctcgg ggtggccccg gaaaagggga   4680
gcccgcggcc acggctacgt attgccatct cgcgagcaga gatgtcacct cctgcctttg   4740
gaggaaaggg agcccggtgg ggatgagcgc atttagccca atgctgggaa caaagcgcac   4800
tccgcgcttc tgcgatttcg ctccattttg aaatgtgttg gcgctttggt ggggccgctg   4860
cggtgggcaa ggccgggggc gctgttaatg gaggaacctc agggggacgg tccttcgtag   4920
gaaactctat cctggctctg cgcgcgcttt aaggaaatgg cttccctcca ggacctcgag   4980
ggatgcagct tttgcgcgga tgacggtggg gtgctgaacc agccggtgcg cctctggaaa   5040
tgtctgggca cggatcctgg ggccatcgac gactcctccc cattcccagc aggcgggagc   5100
tcttacattc cgagcgagtg acccctctca ccctctggcg ctcacacacc tgtaactcca   5160
aacctccgtc tcagaatggt ccaggctgga agggatgatg gggctccgga cagcgactgc   5220
ctagctcacc cctctgcgtg ctcaggctcc aggctcagca ggaccaattt gagttctatc   5280
tgatcccccct cggcccctta actgacccat cctacaggag acagggaaat gtctttccta   5340
ccgcggttga ttctggggtg tcattttgtg ttttgtgatg gctgcttata tttactgtat   5400
aagcattgta tttactgtat aagcattgta ttataattac tgtataagct gcttatattt   5460
actgtataag catctccaaa tcctccctct acgtaaacaa attaatggat aaacagataa   5520
gtgtatcccc tgcccccacc cctgctacgc aggtccggag tgactcttga agctcataca   5580
ttccttggcc aagtttgctt ctctaacaga tgtttatata gcaataacct ggcttggctc   5640
ttgggttcac ctttggacga tttggggaag ggcttgttg gctttgctgg gttttggatg   5700
```

```
agtgacagtc catgactgtt cctgctggaa gggcgtgact tttaagtggt ttctaatatc   5760
aggcattgct cctccgacag gaacaaaaga aatggatact gcccataaat tgttagaaaa   5820
cttagaatcg ctttgattga ggaaaggtta gatttattcc ggttggaaaa agtggccttt   5880
ctattaaacg tgccctttga ccctcatgcc cttggaggtc ggtgccagcc tggagatggg   5940
ataagattgt ggttttcctt ctgccttttt aacatctgtt gttacagtcc atttgttgaa   6000
aatttaaaga aactgtttta ttccactttc cctcagcatt tatgtgtgtg gtttcagtag   6060
ctctgtggct atatgtacga acacgtgtta tttttccaat tggacatgtg ataattttcc   6120
aactggacct tgccttctat tgatgtattt atttagcatc ttccttactc cctccttgaa   6180
aaagaatcac tcaaaaacaa ataaaaacag ccgtaggggc ctaatacagt gctagacata   6240
caagaggtat tcggtccata ccaaatggat tttatccatg aaggataaat ggggaaatac   6300
agtgggaagc aggtgggaaa ctgcgtttga ctctgctctt tcctccacca ccactttcct   6360
catcaccgtg ttcagagacc cccaaagccc cctcacactc ccagaaacac ccccctggcc   6420
actcctaact tgccatgccc aggagttagg tgcttccact agtgacatgg agctggcgtt   6480
tggggggcac ctcagcaggt gacgggaaga gaagacccca gcctcaccag ctgggctgca   6540
gcagggagag gagtcctcat gttccagcag ggactctcag ctgttttcct gtaaaaccat   6600
ggttctcaac tgggggccac tgagatgtct agagagatgt ttttgttttc acaactcggg   6660
gagggtgcta ctgacatctt gtgggtagag gccaggaatg ctgttaaaca tcctacaagg   6720
aaggcacagg acagtctcct acatcaaaat atgacccagt cccaatgtca ccactgctgg   6780
ggttgacact ggcactgcta tcttaattac attcattgag tgtcttttag gaggccctat   6840
tctaagtgct tgctaagatt atctcattta atcctcacaa cacttccgct atgtagcagg   6900
tgctgttatt atctccgtga tggggaaact gaagcacaga gagggttagt aacttgctaa   6960
aggtcacaga gccagtgggt ggtggagctg gttgcctgac actagttccc tcccctctca   7020
gccacatgtg ggtttacttg gccattgtgg actagtctgg gaacccagat atgatctata   7080
acattgaccc agtagaatat tgattccaaa accactgtct cacaaatgaa tttttacaag   7140
agtctgtaat cggagcatga cccagaataa ggttagggag atgtggagtt aaagctctca   7200
atttcttatc tggccccgac acagagagca aggcatttca ctctacattg gtgctctgtt   7260
tataaaacaa agagcaaata tctcttccta aggtccttaa acctcttccc ccaatccagg   7320
gtttctggac tgctctgcca tatgacgggg cagctggttt gattgaccca gggaaggctg   7380
gaaatcaaga ctgggggatc aagacgtaga ttcagtgtgg ccaaggtcaa gtctctgagg   7440
tttagggaca tcagatcccc agcttaggtt ctgtacctcg gcaaggtgaa agcgttggcg   7500
cccactgatg aggcctgctc tgagattgtg ggtgtgggtt gagttgggtg ggcataggca   7560
agtcctcttg taagaatctt ttggcaaaga tgggcctggg aggcttttct cacttcctgg   7620
ggcccaggct ttgcaataag tattccatta tactgtggta ccttggggct acctgagaat   7680
cctctgtctc gcccctgttg ccttgccaaa gagtttgctg tccaagaatt cctttcctgt   7740
ctccaggtgc catgctcctg ccacctctgc caggttccct gcctgcccag atggctccca   7800
actgagtgtg aggaggaatt tgagacaggt tttgagcttt ctgggttctc cagttaggaa   7860
actttctgta agcatgcaga tagaatgggc ttcagcaaaa tacaaactcg aacaacttcc   7920
atgtatagtc ccttaatttt ctttgctttt ttcatatttc atcaggctcc atgctgagcc   7980
caatcaggga cccgatagaa atccaaacac catgtcagcg agtccccaag aaatgcattt   8040
tgtgccaagg ctattcaagg aaggtttggg agcagctcaa gggcagacac tgttaccctc   8100
```

```
ccccaggtcc ccagtgcagg gcagtgttct gcatgtggag gcagtttggc ctaatggtta   8160
aggaggtagg ctctgatcgg gcctcctggg cacaaatccc agctccctgc tcactgtgag   8220
acctaagcca tattgtttag ctgcttggag agttttttgt catccacaac ttggagtatg   8280
atggtacctg tctcacgggt tgccatgggg ttcacacaag ctaacccggt actcactagg   8340
gccaagcaca tagtaactgc tcagtaaatg gcatcatcgg cggtgtcctg tggatgagtg   8400
cttgtgattg gctgaatgac cagaggggtc taaagatcct ggtgatggaa tcagttgtac   8460
agataaattg ttacactgag tagggatcaa gataggaaaa gtcggcaact acccagctcc   8520
cctgcaccaa actgggcaga agtggatcct ctgaaaattg cacacaccca tgtttaaatg   8580
tacacacaga actcttgcca caggcaagcg gagatttgtc atctgctgtc cctgcctcat   8640
cttcttcctg aaatccactc catgccagga ataaactgca tgctctccac cagcccaaac   8700
tgacctgcct tcccgccagc catcccgggc agggtgacct ggcttagtac atcgggttca   8760
gagatctttc cagtttactc gttgaataaa aagtgagggc tgatcgagaa agtaatggca   8820
gtcagggaag gcgaaggagg taaagaagag attttacaaa tgaagtaatt caacagagtg   8880
ctgacattgg taaactggca aacagatttc agggtggttg gttgagagta gagtagaaaa   8940
ggattaaata aagcaaactt gtggtgtact gaatcttagg aattccatgt atccaataag   9000
tatagtcatt tatgaattaa taaattcggc ctaagaagcc ttcttatcgc ttaaatcaag   9060
actaagtaac aatatatcag ttttaaaaag tcattatatc agaaaatcat ttaaatgata   9120
cacatagatt tccaagattt tactttaacc gaaactatat aaatgtgaat ttgttcaccc   9180
atcttttgac acagggctca ggtcttctct tggtgtctgg atcagccagt tgaaatttct   9240
tgtctgtttt gcctatgcca cattaataat gcactgtctg ggtcctccga tttcagtttg   9300
gattttgggt ttacattgtg gagtcatctg aatgcagaat ccttcaggga ttttactttt   9360
tttttttttt ttcatggtct ttaccatccc atttgatagt aaatattact cacctttatg   9420
aagtctttcc aaaacattca actaaatttt cttaaaatca ttgaatgatt tgaagagctt   9480
attcctcagc acttttactc catcagcttg caccttattt tttaatcttt ttttgagacg   9540
gagtctcgct ctatcgccca ggcttaagtg caatggcgcg atcttggctc actgcgacct   9600
ccacctcctg ggttcaagca attccgcctc agcctccgcc gtagccggga ctacaggtac   9660
acaccataat gctcggctga tttttgtatt tttgtaggga tggggtatcg ccatgttggc   9720
caggctggtc ccgaacttct gacccaagtg atccacccac ctcggcctcc caaagtgctg   9780
ggattacagg tgtgagccac cgcgcccggc cagcttgcac cttatttagg atatgtgatt   9840
attatagcaa gtctggtgta catacaagat tttgaatggg cacagatgac ctttagtaag   9900
tgcttggctg tgataagagg cagtcctgac tgcagatcag gctgtgtgga ccccagcctt   9960
gcatgtttac agaccttcat gtcttattct tacagggtat cagaagaaca cctactgggg  10020
aaacttataa attagtaaaa ggtgggcatt ctccccgccc atcttctgtc tgtctgccag  10080
gactagcaca gcactttgaa gtcattcaca tagaatccca acttaagagg gtaaaatcct  10140
cctcaacaga ctgaaaataa gtttaaattc cctttgctat attaactccc ctgaggaaag  10200
agtcttagat caatgtccaa cactaaaaac agttttaaat cagcaagtga gaattaaatc  10260
tgaagcaatt gataataatg tttcattcat tcctctcctt tggccccgtc caccctactg  10320
ctaaatccag gcatcaaaga gaagagggac ataattatct ctagtcccag ctgctggttt  10380
tccttccagc ctatggccca gttttctgtt ttactgagaa ggctggtgat gttatcttgg  10440
```

```
gatctaagtc tgcagtttca ccacaaaaag tccagggatg cactttcatg cttgtgtcct  10500
cctccctggg atagcaagga tattagaaga cccctggctc tgtaattgct tgtcatgtgc  10560
tctacagacg ccacagaatg ccaagaacga agtgctggga aggacaaatt catggaaccg  10620
tgggacggtg ctcctccccc agcgtaaagg acagctcctc ctcctgaatt ggagccagcg  10680
ttctaaatca tgtgtcaaca gagttgtcct ggatcggatc cagttctgcc attgatttgc  10740
aggtcatttc agtggtacct gtttccagtt gttcttaatt gaacagtggc accaaactat  10800
tgtcttgcct catccccctc ccatggcctg tcccccaaaa agagacttct tgggtaatta  10860
atcagggcaa catcaggcag tctgggcgcg gtggctcacg cctgtaatcc cagcactttg  10920
ggaggccgag gcgggcagat catgaggtta ggagattgag accatcctgg ctttgtgaaa  10980
ccccgtctct actaaaaata caaaaaatta gccgggcgtg gtggcgggcg cctgtagtcc  11040
cagctactcg agaggctgag gcaggggaat ggcgtgaacc cgggaggtgg aggttgcagt  11100
gagccgagat cgcaccactg cactctagcc tgggcgacag agctagactt cttctcaaaa  11160
aaaaaaaaaa aaaggaatct ctttggtttt atatattttt ttttatatat ataatatata  11220
ttaaaatata atatatatat ttatataata taatatataa atatattata tattatatat  11280
ttttatatat tatatattat atatattata tattatatat ttatatattt atatattata  11340
tatatttata tattatatat ttatatatat tatatattta tatataatat atattatata  11400
ttatatatta tatattatat attatatatt tatatatatt atatattata tatattatat  11460
attatatatt tatatattat atatttatat atattatata ttatatatta tatatttata  11520
tattatatat ttatatatta tatatattta tatatattat atattatata ttatatatgt  11580
atatattata tatgttatat attatatata tttatatata taatatattg tatatattat  11640
atatctaata tattatatat attatatata ttatatatta taatatatat tatatattat  11700
atatattttt atatatataa tatgtataat atataatata tataaaaaca tatataatat  11760
atattatata ttatatatat attatatata ttatatatat taaatatatt ttatatatat  11820
tatatatatt atatatatta aatatatttt atatatatta tatatatata cacatatata  11880
tatataaatg aggccaggct cggtggctca cacttgtaat cccagcactg tgggaggatc  11940
acttgaagcc aggagtctga gactagcctg ggcaacaaaa caagatcctg tctctacaaa  12000
aggaaactgt aaaaattagc tgggcatgat ggcatgtgtc tgtagcccta gctacttggg  12060
aggccgaagc aggaggatcg cttgagccca ggagttcaag gctacagtga gctatgattg  12120
tcccatagca ctccagcctg ggtaacacag caaggccctg tctctaaact tttttttttt  12180
aattctattt atatttacat gtatttaaat gtgaatattc actacctatt tgttgcatgc  12240
ctgcattttt tatactgggc ttgccaaaaa cccgaacagc tttctacttt gacaatgtat  12300
cagaatttaa atcagcaata tgttaataag ccaagcaaag gttatatatg caaataaaac  12360
tgttgtctat aacctcctgt tacactgggg cacagcaaaa gtcatggtgt agtcgcatgt  12420
gaacctgtcc ctttcatagc tgctcattgc caggaaacat caggaatagc catttggaag  12480
agtcatcagc cctcccacca tccgttttct gtcttgtctt ttccctatga gcaggggaaa  12540
ttccacgctg gccccaatcc ccagtgcagc ggctcagcct ctgcctctgc tgctggtccc  12600
catgaggcca gcttagaaac ggaggatttt gcagaacatc cctaaatccg cttgaataat  12660
gaagtgatca ttcataaact cacctgaacc ttattaaaac ctatttaata tttttcctgg  12720
ataatcctat agggataact tgcctcctgg gcttctctcc accgggttca gttcttcctt  12780
tagtggtgaa gttcctccct tcttagcatc tcaactgtgc ctgagaaaag gccagtggcg  12840
```

```
gctgcactct gttccctgtg gagtgttaat aaagactgaa taaattgaaa taaatccctt  12900
tcaatgtcat taagtgctat aaataatcat gaaccaatgt tcgatggctg atgagaaatg  12960
caagaaaaaa tttttaatca gtaggattca taagttgaca atctgggcca agttaaaaaa  13020
aataaaaata aaaagacttt taaaaagatc ttatcgtttg ttaccagtaa gactgaattc  13080
cagaagcaag ctactccctc atttgtgggc ccctgttatc actggctgct tagggttgcc  13140
aagccctgaa ttcatttgtc aactaagaga tttttggcca agattaagat ttcccatgcc  13200
tccatatttc catctgagaa atggagatta tactgtcttc cccctcagaa tggatgataa  13260
tgtggtctct cttctgttcg catagtcata gaactgaaat aaaacaactt aagagaattc  13320
ctttgagctt ctcagaagtg ctgcagggct gggggatgcc tcccaggagc cgcagtcagg  13380
tgctgatctg aagtctttgg tgggctgact ttagcctgac ctgaaatagt atagctgctg  13440
ccacctggct cccttagcgt cagtcagacg gtgcagctgg ttcctagggg tgagggctga  13500
gccagcaggg tccgtgccca ggagggatgc atgggtggcc acagcccagc ctgcactgat  13560
cttgtctgtc cccttctttg gaaggaagga gccccaaacc agggtgcaag acagtgggtg  13620
ggggtgcctt gagcatgacc tcaagtgatt tccagcccct gccagtgctg acttctctgg  13680
ggaagggctg ggacttcctt ctgggctcaa gtcacgaccc ttggatggaa tttcctggga  13740
gcttttctgt tttttctgga gttttcagtt ttttcctaac cagacaggga cttggtacag  13800
aatctcatat tctaattatg cctaggagca gcctctcccc accactcaca gtgtttagca  13860
tgtgacagga atcgattaag gcatgagtga ttaaattaaa gccaggcatt gacttggatg  13920
gtgtaatatt ctgacatctg tttggtgtca aaggcacggg gcaggcgcgt taattgaact  13980
gcttgcacct ggcatttgaa ttgagccaga gcggggctaa agtcagtttg ccttcaccct  14040
gtaaatggag ggtttctccg gagcgtggat ggtgggaggt atttcagggt gtatgcataa  14100
cccccaccct gacaatggcc catctcttct ccagcgtggc caggtttgag tgccagtcct  14160
gggtgtccag tggccccata gccttgcgtt ttagtaaaat gctgccccca ttaccacctg  14220
gtctgtgcac ttcggtcact ggaatttgcc atcttccagt cccgaatgtg gcaagccatg  14280
gagccttaag ctcttctccc tccacatcct ggaacagacc cgccagtttc ttccaggcat  14340
tgcctcagtt tgcccctctg tttccagtca cactctcacc agcgataaaa tgattttaga  14400
ccttatcatc tcaccctcgg atccttatgg aaacaataat gagttgttcc ctgtttcaat  14460
tccaaaattc atatccaatc cgttttgcat gccattgcca aattcctccc agagcaaccc  14520
cgtcacctgc cctggccctc tccaagtgtg gtcctgccat gggcatcgcc tgctaagcca  14580
agctggcctc gagctgcctg cccgggtccc cacaccttgg ctcacctccc tgcccagtcc  14640
cgcctcctgc cagcctgccc tgtggctcct tcatagatgc cgtgctcttt ctgccccttg  14700
ctcacccatg gcagccttgc ccctctctcc ctgccccacc ccctatttaa attgacctga  14760
ccttcctcag tgtccatctt ccccgaagct ttccccagcc ttggcactca aggtccagag  14820
gctacgcgtt tcctctcacc tgtggcagcg ccgtgctccc cagtgcctca cagtttcctt  14880
cttgcccccg cttcctgtgt aggactcatc tgcccacagg ttgcacgtcc tgtgagggca  14940
aggactgtgt cttatgtgac tttccttctc cagtcacaga gctgggcaca tagatagctc  15000
aaaaccctct ttattaacac agttggatgt tgagaaatca aacaggccaa tgtcaaatga  15060
gctctcctta tttaaatcaa gtcagttctc cacctcctag cactcagttc cagtactcta  15120
tatacatgga aataataaaa aacacatttc ctttgaaaca ttctataatc gttcctttgc  15180
```

```
cctacttcag accaacttaa cgcactcccc attggtccaa atgagttttg ctatacgaag  15240
atgctgataa taatagcagc agtggattat tctgctaaaa ccattgcctc gttaatcctc  15300
agtcccgagg tggggattat tatcctcatt ttgcagagaa gcaaactgag actcagagat  15360
ttcacagctg gggagggagc cagctcatcc ctctgtccag gcccaagctc tctcccgctt  15420
gccttcctgc ctctgcaacc tcagagcatc cccatctgg ttctactgcc tgtgctagtc  15480
gtgcaggagc caaaagacac gtctttagtg ctaaggactg gagaagccat gccctccagc  15540
ctctgtgaat gggtcatatg taacatgagc ctggagaaat tatttgaaac caaaggcaag  15600
cctctaaacc aggctgctgc ttcatggcgc cggtgacggc agaaccaaat ttagtgctgt  15660
gggcaggtcc acacttatca aatagagaag ctcatttttc ttccggctca catcaagcat  15720
gaaaaatgtt cacacatacc ccccacacac acatgctttc cggaggggtc catgtggcta  15780
gaggctggaa gatgtggatg agaggagcct ggcaggtaag cccagggaag atgacattca  15840
gcttcccaga cagcatctac agggagaaat ttaattaaaa gtggggcggt ttccctgagc  15900
aaggcagaca aagtcagccc tctactgtta agaaaaaggg tcacagtgag aggggaggtg  15960
aggagactga gtctgtattt tctagtctgt tgggctacac tacctgatcc cccttcctca  16020
aaaatccact ttactttccc catgtctaca ccaatgtggt tcacactctg ggaccaggaa  16080
aagggggagt gatggggaac agagaaggga ggagctcaca cagctgaggc tggggttatg  16140
catatcgaat tacttagaat ttgcaacctc acagggtact ttcatggcgt tgaaatacac  16200
ttcccacagc caccctccct ctaactaaaa gcaagagtca tttctcagtt ctggtcttgc  16260
ctcccacgtt ctcctccaca tttaagaaaa tccaccagct acaaagtgaa gataccatat  16320
gtgatatccc accctagttt ctgttttatc agggtttgga gcaggtggag caggcagagg  16380
gatcatttca gcctataaat tgtattaagg gtgagtactg agtcattctt caagaaaagt  16440
tttagaagca tccaaaactg aagggtggag ccacctggag acagtatcat cagtcctggc  16500
cccgagcatg gcctgcatag gcccccatgg atcccagcgg gagctgcaga gtgcgggcac  16560
cttggcacac agccctgagt gcaaaattag gagctgggca gagggcatct ctctgtcgcc  16620
attgggcagc ccagggcaca ctggtcatag ccttagacca cgaacaccct gtgcccgggg  16680
gacagatgca accagtgtgc cctgggctgc ccaatggcaa cagagagatc gacacctgga  16740
ccccatgtca cggggactcc actactaagg ctcctaagac tgccaccttc cagtgggata  16800
agccctgcct cctactgggc ccacaatgtg cagagaacac ttgggactac ctggctttct  16860
ggatacacaa atattgatcc aatctggact aattagaagg tcagtcccaa taacaaatcg  16920
aagtcagctg ggcgtgatgg ctcactccta taatcccagc actttgggag gctgaggtgg  16980
gcagatcatt tgaagccaga agttcaagac cagcctgggc aacatagcaa aaccctgtct  17040
ctactaaaaa tacaaataat taggctgggt gtggtggctc atgcctgtaa tcccaacagt  17100
ttgggaggct gaggcaggtg gtcacctgag gtcaggagtt tgagaccagc ctggccaaca  17160
gggtgaaacc ccgtgtctac taaaaacata aaaattagcc aagcatgatg gcatgtgcct  17220
ataatcctgg ctactaggga ggctgagaca ggagagaatc gcttgaatcc aggaggtggt  17280
tgcagtgagc tgagatggtg ccactgcact ccagcctggt tgacagagca agactctgtc  17340
tcaaaaaaaa aaaaaaaaaa aaaaaaagcc atgcctggtg gagcactacg tgtaatctca  17400
gctatttggg aggctgaggc acgagaatca cttgaacctg ggaggcagtg gttgcagtga  17460
gctgagatcg cgccactgca ctccagcctg ggcgacagag tgagtgagac tccatttcaa  17520
aaaaataata aatctgagtc actttaatat tgttatttgg atgtcaacct ctaggtgttt  17580
```

gagacaggag agtgatatgg gggcactgga aacacacagg cacggggtgt cctcacactt 17640
gggtagccca cacgatgtga tttcagggtg ctgggaggtc cccccactcc ccaaattact 17700
aacaagtgga tagtacttta cagtttatat gatctcattt gattcttaac atgagcctgt 17760
gagtgaaaaa ttccttcccc tcttctacag attaggacgt tgagattcag ggaggttcag 17820
agggattcag ggaagtcaag tggcacctgg agtcccgtgg ctaatttgag gccggtaggg 17880
gattcgaacc caggatttgt gcttcttatg cctgggcttc tgctccctgg ggcatggtct 17940
tccccctagc tttcccattc actgctttag cctaggggtc ctacccttta ttaaactgcc 18000
agtgcctcac tgcttttctc ccccaaagac aaaaaaaaag tgtttttgct tttgttttgt 18060
ttttcatggg cagagacctg gaatttcagc ttgagaattt gtgccatatg ataaataaat 18120
caacagatgg ctttttcctt aaaaaaaaaa aaaaaaaaaa ctaagatgta tttgcagtga 18180
ggcataattt gtaccaaaaa gtgctcacca cactgtagtc atgggggcag gaggcagccg 18240
cgggtgaagg gagaaatctt ggagtccagg cagccccctt ctgggctgaa ctggggagct 18300
gggggtgctg ccagccctgc caggttctcc taggaggcgg cagctcatat ggctgtggga 18360
ggaggcagag ggagcctcat atgcacccac atttccaggg atctagaaga cagaaggagg 18420
aaaaccacca tcatgttaaa gcagacagtt aggtaacaca tcctgtaata caagttattt 18480
tttccacatc taaaggctaa aaatagttgt tagaatttaa agataattgg taaatgagtt 18540
tctatccttc tagtttcaca tcaaatggaa tcatgctgcc ttcacatcac tagtgcccgt 18600
tatttgtgtt taatttccac aatgttgtct aattccactc tttgggcttc cccagggatc 18660
cagcctccct cactcgccca tcgcagggag atgctttatt catctttgtg tcttctgtgc 18720
cgggcatagc gcatggcaca gaataagcac tcagtaattg attcacgagt gaataaatgg 18780
atgagtgggt gagttcaata ttgactacaa aaaccctaag gccacactgg tgagtggctg 18840
cgcctgtagt cccagctgct ggggaatctg aggcaggagg atctcttgag cccaggagtt 18900
tgaaactagc ctgggcgata tagcgagaac ctgtctcaaa tgacaaaaac agggccaggt 18960
gcagtggctc acgcctggaa tcccagcact ttaggaggcc aagatgggag gatcacttga 19020
ggccaggagt ccgagaccag cctgggcaac atagggagac cctgtctcta caaaaaattt 19080
tttaaaaatt agctgggcat ggcggtgtgc gcttgtagtc ccagctactc aggaggctga 19140
ggcaggagga tcacttgagc ccaggaaatt gaggctgcag cgagccatga tggcaccact 19200
gcactgcagc ctgggcgtca gaacgagacc tgctctcaaa aaaacaaaca aacaacaaaa 19260
aaaaaggctt tcttaaagag acttgagaac agaaagggga acagatacat aacttatata 19320
tttatttgtt catctttcca ccttcctgga gggtggaggg gaacaggtct gtatttggag 19380
ttttgaatgc taaaagtggg aatacatgta ctgtttgcca tgatctgttc aaaagttaag 19440
ccaaatgcct tagattctcc tgaaaactgg aatgccactg taaactataa gccccacttc 19500
aaagataaaa gatcttgatg aacagggctg ggtctgtgga ctgggcctct ccccaccaca 19560
caaggaaggg tggtgccagt tgaaggaaaa tcacttaaat ccttgctgtc tcctaataag 19620
gtgtggtccc aggtagggct gtcagaatta gcaaattaaa acacagggca tctgtgaaaa 19680
ttagaatttc agataacaac aaataattgg cataggctgc ataatgtccc tcaaagatat 19740
caggtcctaa tctccagaac ctgtaaatgt gatcttattt ggaaaagggg tctttgtaga 19800
tgtggttaaa ttaaggattt tgagatgggg ggattatcct gtattatcta ggtaggtcct 19860
aaatgcagtc acactcatcc ttgtaagagg aaggaagaga gagatggaaa acacagaaga 19920

```
gaagacaatg tggtgatgga ggcagagatt ggagtgaggt ggccacaagc caaggactgc  19980
tggcagctac cagcagccag aaaagtccag gaaccaattc tctcttggag ctccagaggg  20040
agtgtggccc tgctgacacc ttagcttcaa cctagtgatc ctgattttgg actttggcct  20100
tcagaagtgt gagggaatga atatctgttg ttttaagcca ccaagtttat ggtcatttcc  20160
tacagcagcc acaggaatca aaaacagtaa gtatgtccca tgcaatgttt gtgacacaca  20220
ccaaaaatat tacttgttgt tcacctgaaa ttcaaattta actgggtctc ctgtatttta  20280
tttggccaac ctagttccca ggcccaaaga aagaggcttt tgaaatttgc aagaaagctg  20340
gttggagctg tcagaaagtg gactttgtaa acacagtacc accgaaccaa tttgaactgt  20400
actacctcta gacaaaagag agggcagtca gacagttgtt cgtgatttct tctttcaaca  20460
gtcatttgag cacttactac aaaacagaag ctatgtgtaa gggtggaggc gttagctgtt  20520
aatcaggacc tccaggctaa gtttctgtat tagtccgttt tcacgctgct gataaagaca  20580
tacccgagac tggggaattt acaaaagaaa gaggtttaat tggacttaca gttccaagtg  20640
gctggggaag cctcacaatc atggcagaag gcaaggagga gcaagccaca tcttacatgg  20700
atggcagcag acagacaggg agagagagct tgtgcagggg aactcctctt tttaaaacca  20760
tcagatctcg ttagacttat tcactatcaa gagaacagca cagaaaagac ctgcccccat  20820
gattcagtta cttcccacca gatccctccc acaacatgtg ggaattcaag atgagatttg  20880
ttaccatatc agttaccaac ccttccagat aaatcacgtg aaatatcgcc attaacagag  20940
tgagctcagg tggttcttca gtgcatttct gatacctgaa ccttccctgg gaatttcaca  21000
gaccatcagg ctctccaccc tttgatagca ggatagcagg gcccaggttc tgcaggagga  21060
gatgttacca caggcctgaa agggagggag gggcagatgc tacaggaaga tgctggctct  21120
ggattcgctg gaggagcttt caagggaagt agatacacac tgtctccatc atttcatgtc  21180
catcacactc taaaatgctt tggacaagaa gcaaatgtta aagacaaatg tggcccattt  21240
tcctgtacaa agagggctgc tcccatgcca ggctattggc actggtgggc atgaggcttc  21300
tctgctgccc tggccggggg gttctctcac tcaccattgg ctctctgaca cctggagaga  21360
ccaccaccct tgggctttca tgatgctcac agaatccaca ctgttggagc tttaaggagc  21420
ctggatcaac tggaacaggc agggagtact aggacagccc agcattgccc caaaatatcc  21480
aggcctgata aaagagaaaa acaggtagct cacaggaaaa ggataaaaaa aggaggaggg  21540
atttaacatg aaaaggtgct tgatctccct cataataaaa agactgctga ttccatccag  21600
gcaagtgaca gaaaaaaaaa atttaattta aaaagactgc tgataaaacc acagcgagac  21660
actgctgctc agggatctga gggtgtgggc agccaggctg ccacgcatca tgggtcggag  21720
aggaagacca cacccctgga gcagagggcg gctgatctgt cagatgccct ttgacagcac  21780
ctcagcttcc aagaattaac cctttctatg tgagcagagg catccatggg gggacacact  21840
ggtgaatcat ctgttatgta gaagtctgga aaacatcagg atggaactgg tgaaataagt  21900
gtggcctctg acggaatgga gcggtccgtc tgcactgctg cgggtgcccc tcagatcctg  21960
tgggtcagtg agaaaagcag tgaggaacaa ggcaggtact gtgtactgtc ctctgcgtgc  22020
aaggaaggcc agcgcatgca acagagtcca cacagacata gcctaactct ggaaggaaga  22080
atgagaatgc agtttcagtg gtggcctctg gtggggagaa actgggtgaa gggagatgtc  22140
atttccattt ctctactatt aattttgtat taccatgctt aaatgttact ttttaccttt  22200
ttttttttt ttgagacagg gtctctctct gttgcccagg caggagtgca gtggtacaat  22260
catggttcac tgcagcctga acctcccagg ctcaagcaat cctcccacct cagcctcctg  22320
```

```
agtagctggg actataggca cgcataccac cgtgcccagc tattttttt aatcaagatg  22380
gagtttttct atgttgccca ggctggtctc aagctcctgg actcaagcaa tcctcctgcc  22440
tcagcctccc aaagggctga gattaaaacg tgagtcaccc tgcccagcca attgcttttt  22500
aaaaaagatt aaatgcatgt atacgctcag gcatcagcac acttggaaag gatgaaaata  22560
tccggaagaa gggttctttt aaaaggctcc tcaagtgatg ctggcaggca tgacgaatgt  22620
ccctggtcac aaaagctctg atctggccta accctgtcat gttagagact ggagtgcgtg  22680
tgtgtgcgcg caaagtgtgg ggggatgggg gtgagtgtgt gtggtgtgta agcatgagtg  22740
tgtatgtgtg tggtgtgggg gtgtgtgctg tgtgagcgtg tgtgagtctg tgtgtgtagt  22800
gtgtgtgtga agtatgtggt gtgtatgtgt gacgtgaggt gtgtgtggtg tgtgagttgt  22860
gtatggtgtg tgcatgagca tgtgtgtggg catgtgatgt gtgtgtggtg tgtaagcatg  22920
tgtgagtgtg tatgtttgag catgtgtggt gtgttgtgat atgtgtgtgg tgtgtgagca  22980
tgtgtgtgtg atgtgtctgt gtgtggtgtg tgtgagcatg tgtgttgtgt gtgtggtgca  23040
tgtgtgtggc gtgtgagcgt gtgtgtgcat tgtgtctgtg agcatgtgtg agtgtgtgtg  23100
tgttcagcat atataaggca tgtaactgaa cacagcactt tagagggctc tcctggagtc  23160
agagggggtg ggtaggagga gaagggaggt gggctagtgt gctgaagtat ctactccttg  23220
tcatagtctg tgacaaccca gactagccca tgagccaccc tgttccctgc atttccaatg  23280
agacctcggt ggacatgttc cctgaggtga ggctgactga tgtcatttga cgatcttgat  23340
gccaaatcct tttatatcaa aaacaaccag aacactctct tttctcttag tgctttcacc  23400
cagatgacca catttcatcc tcccagccac tctgggccag gtggcactgc tggtttgaaa  23460
gggaggtctc ccctggagta acttccgtgg gcggattcac accctgccca cagtcctgtc  23520
ccagtcagcc caccatggtg gtctccggtt cctccagaat tcccgctttt cagctcatcc  23580
ccacattccc ggagggactg agagcgcagc cccagggccc tgctctttgg gggccgtctc  23640
tacacccaga gaagcagcaa ggcattccta ggtttctctt tcagatgcag aacttcagtg  23700
ttcagagatg ttcccactgg tcctgagagg gctcagttca gctttaatga ctgcgctgtt  23760
gcgtgtgctc tgcagagggc gggtggccca gcgtggctga ctgcagtttt cctgacgtgg  23820
agcccgagcc tgccccgctg tttattaatt aaggatcact ctgcttgcag aaccctgaac  23880
tccccagaac tgtgaggtgg gagaaccccg agaggccacc tggccccact tcccacctgc  23940
tgcccaaacc ccctctctgc cttcctgaca gtcaccccaa ctcccagtga tccccatcaa  24000
ccatctgaca aggggactga gagggaagag aaaggagggg cccaaagagg aaggtaaaac  24060
tgtcgggaac agcccccaaa tgtgtgacag ccttcagtgg agttgcccac tttccctttt  24120
ctcctccctg caggacctcc cttctcccca gtcctcccca acttctgagg ttacattgag  24180
aaaagtctgc agagaggtgc cagcatcaca aggtgttaag gaccacgagt ttggcatttt  24240
aacagatgcc agagccactt gagaaatgtg gtaactaagc ccagagaggt acagttaacc  24300
tccccagagt cacacagcag gttcatggca aagctggact agcacaggtg tccttcccct  24360
gcagatcccc ttctgtgccc cacatcacct ccctccagtg tctgggccac ctggagatgg  24420
gccctcagac tcacccggcc agaggtgcca tctcatggga gaggtctggc caggaagcat  24480
cgatatttga gatcccaaga aatgaagact tggcctgtca gatgacagac ttcggtcatg  24540
ggaacacgtg atctgtttta cacatgcgtc ccctcagcag cagctttcca gaacattccc  24600
actttcttct gtagtgagaa gaactctttc cctgcagcct cctgcccaac tcctccttca  24660
```

gtgtctttgc ttcagtgtct ttgataaacc attctgcttt gcagagtgcg agctctgcct 24720
tgcagggttc gcatctgcct gtgctgagta accaacgcta aggtcgagtg gtcggtcacc 24780
tctcataaga gctagggttg tctcatgctg atgactagga cttgccctca aggagaaaaa 24840
taaatcaaaa caaaagcaaa aacagcaaac atgcatctct taaagaaggc tctgagtcca 24900
ggtaaatttc cttccactga agcagccagg ctgaattcga attatctttg cccctgctta 24960
aaaactaatg caaattttcc tagagaatat ccactaattc ctggaggggg catgggcatt 25020
cctgatgccc atgagaggac catttgctct tccctcagta tgctaaataa cagaagcgac 25080
atttgttgct ggaaagtatc agtgaagtta ataaggtttt tcttgcccag ggtgagggaa 25140
cagttcccaa tgacaaatgc tgtatgggaa ggggctgtag aactgccagc ccctttggtc 25200
catccgtaaa gtgaactctg tggatcctgg aggattccag cgtctttttt tttttttctt 25260 ttttttaag acagagcctt gctgtcaccc aggctggagt gcagtggcac gatctcagtt 25320
cactgcaacc tccgcctccc gggttcaagc gattctcatg tctcggcctc ccgagcagca 25380
agactacagg tgcgcaccac catgcccgac taatttttgt attattagta gagacggggg 25440
tttcactctg ttggccaggc tggtctcaaa ctcctgacct caggtgatcc acccgcctca 25500
gcctcccaaa gtgctgggat tacaggcatg agccaccatg cccagccagc atctttcatt 25560
tttctgtctg ctttggccct ttcctctctc actgtcttcc ttttccattt ccaaagtcag 25620
tccatctcac tattagcaca aaaactgcta gagcgcttgt cattggtcat ctctccctgc 25680
acctggctgg tctgttcttg gccactgaag cgtttccccc agctgttgct ttaatcattt 25740
tattgttatt atgccttact taagaaatgg atatgagatg catttacctg tctcttcctg 25800
ccactctgca gagccagtaa gatgtggtgg aaagggccca ggctttggag gagggctggc 25860
tggggttgga tcttggctgc cccctactag ctgtgtgacc ttgggtaagt agctggacct 25920
ctctgagcct ggttcggaat catagcacct ctctttcagg gctgctgtaa ggaatagcag 25980
tggtgtgtat aaagcagagc gcacagccag caactggccc ctagccacac tgctgagcac 26040
ctactgtgat aagctgccat tgtggtgtgt gaagcaaagg ggaaacatgc ctgctgtagt 26100
gagcttcctg tagggcaggt tgtagaacca gaggtgggtt ccaaggttac aaagggactc 26160
ttagtgtatt agtctgttct cacattacta taaagaccta cctgagactg gatcatttat 26220
aaagaaaaga ggtttaattg gctcacattg gctgggtgcg gtggctcacg cctgtaatcc 26280
cagcattttg ggaggccaag gccggcggat cacttgaggt caggaatttg agaccagcct 26340
ggccaacatg gtgaaaccct gtctcttcta aaataaaata caaaaattag ctggccatgg 26400
tggtgtgcgc ctggaatccc agctactcag gaggctgagg tggaagaatt gcttgagccc 26460
gggaggtgga ggttgcagtg agccaagatc gccccactgc actctagcct gggcagcaga 26520
ctgagactct gtctcaataa aaaaaaaaaa aaagaaaaga aaaagaattg caagaaataa 26580
attattgttt atgagctata tggtctgtgg taccttgttg tgggactggg agtcttggcg 26640
tctccctgac cctgcctgtt gctgcagcac cgctcagccc tgcctgctcc ctacctgcct 26700
cccctcggcc tctcctgcct ccaccgggcc cctggtgcct cctctagaga cagtcctcct 26760
gggaccgatt gtgttctcac ttacacgagg catccaggac tacagataac cagaggaagg 26820
ggcgcccccc ccgcctgccc tcctccctgg catcctcacg ctgcagaggt cagagcctca 26880
tcccagcccc ttacctgccc ctactctgtg gagaaccgtg gtcagttcgc caggccggat 26940
ccacgaacgg ccttgtggaa gatggtgagc tcacacccag agctggctcc gatgaccctg 27000
tctcctttac atgtttctac cttcccctcc ctaccttccc ccactgctgg gcgcagagtg 27060

```
gaggcagatg aggtttaaag ctcagaaggg cttaaacggg ttggggcgca gtggctcatg  27120
cctgtaatcc cggcactttg ggaggccaag gcagaggatc acttgagccc aggagttcga  27180
gaccaacctg agcaacatag tgagaccgcg tctctacaaa aaataaaata aataaaatta  27240
gctttgcagg gtggcatgca cctgcagtcc ctgctactca gaaggctgag gtgggaggat  27300
cgcttgtgcc caggagtttg aggctgcagt gagctatgct ggcaccacag cactccagcc  27360
tgagtaacag aatgagatcc tgtctcaaaa caaacaaaca aacaaacaaa agaaggctta  27420
aagggggctc caggtgggct tggcagcaca aagctatgaa gttctatctt agacacaagt  27480
tctgttactg ggcctttgca ggctggcctg ggtacctggc tgccatagac agggaacctt  27540
ccagatgagc tgcaggcgtg gagcacagga gccagggtgc tcttcctggg ctctgtccac  27600
aggcagaacg tacacagtct ttgtacacgt ccggcggctc tggtgcctat ttttgtttgt  27660
gtttttcttt tgtttggggg gatggatttg gtttccccccg agccctctgt cctcctgtca  27720
cctggctggt gctcggcaat gttgaccagc tgcctggctg gagttggcag tggctaaggc  27780
tgtgacagct aacatgttcc tgagtcctct catttcttca ccataatgcc ctgttgagtt  27840
tgcagatact gtctctgttt ttatctcccg gggaaactga ggctcagagt ggctaggcca  27900
ccttcccatg gtccctcagc tcatgagggc cacacagggc attgcggtgg ccttctcctc  27960
agccttgacc ctccggcccc agcattgctg cctcaagggg tctcctctgc tgagccgtgc  28020
accttctgcc tggcagctcc aactctgtgg ctgtgttcag tggctcagca ctgccccttg  28080
accctccctg gccttctgcg gatgccagac tggagcactc tgacaaggtc tggggtggtt  28140
gtatgggtcc tgtgacctct atacacctcc cagtgcctgg gaatcctgca gatacaccct  28200
ccttagccgt ccctaaccat agaggacatt tctgaggtcc ccgagagagt ggggcacccc  28260
tgcaggatcc aactgctggg cccaggaagg atagcagcag catgaggggt tccattagcc  28320
acaaactcac ggcatggaac cttcacccac ctcgcccctc atctgctgtt tagcacctgg  28380
cacgccgtgt atacttactg attattacat tttaatggca aattatagtg gcaaacgtat  28440
gcatctttgc acaattgttg tacagcatga tgaacaagtc attaatagta aagaataaat  28500
gtgaaagtga gaaaaatctg actgccaaag tttttactcc ttccttccct ccccagactt  28560
ttaaatgaaa gtttagggat aatcccttag ttgtcctgct agtaggactt gcaattaaaa  28620
gaattgggcc aagaacactt ctacgcttct ccttttaggt ttgggtgtaa attcggggta  28680
tttctcactg atgaaagcct ggtgcagggc agaccgtggg aagctttcat ttccggaatg  28740
gaccatcaac atcccttgga gaagaattct cttctccaga cccagacctg gtgtcctggc  28800
acccattggg caagtgggtc ctagaagaca aacctggtca gagcctggag gctgcttagc  28860
attccccacg cacattagca gctcggagag ctcaggaagc cgcagcccct ccttgcctca  28920
ccagcctgga tcaggacagc atcccctgga agacacacag ggcctggcct ctgattaccc  28980
agcctggagg gaaagctcaa tcgagcatca tgtcacccgg tgccccccatg cagggtggca  29040
ctggtgagac ccccaagcca atgataccac ctcacaggag tgcaggccca ttgtggccag  29100
atcatcttga cttttcaaga taaatcagaa atcgtatttc catgagatat ccctatttgc  29160
aagtgatggt gactaaatta gaagtttttg aatattgtaa catgttcgta ggctgtttgt  29220
ctggtttaaa ctctatctgg aggaattcaa gctagacttc aggaataact tcttgaggca  29280
aggattttga gaccttaggg aaagaaggac gtcttggggg tattctgact gttgtcctcc  29340
tggaagggaa gaacagagaa ctagaagact gcccttagcg aagttcaaag cacctaagcc  29400
```

```
cgggaccctc agcaagtgtt cttgagtcac agattctccc tgaggcgcct ctttctggct  29460
ccatagaatg gctgattctg taactcggtg agtttgcttt ttttttttcc tccatcaccc  29520
aggctggagt gcagtgaagc tggagtgccg tggagcgatc actgcaacct ctgtctccca  29580
ggttcaagca attctccttc ctcagcctcc caagtagctg ggattacaag catgcagcac  29640
cacacctggc taatttttgt gtttttaata gagacggccc gaagtgctag gattacaggc  29700
atgagccacc gcggccagcc ataactctgt gactcttgtt acaaaggcct tatattttgc  29760
tctttgaggg tggttttggt ttgatgcctg ttggttgcca tcttttaact agggatgttt  29820
tatcaaaatg cccagccaaa gtgtccaaac aaattatacc ttaaagtttg aaaatgtctg  29880
gcacttctaa ttcaatgcct gttgtgccag gcactgggct gctgaggaac tgagtcccgt  29940
ccctgcaggc tagctagaga acacacacac acacacacac acacacacac acagagtggt  30000
cttacaagtc agttttatat tctacctata tgcaataaag gtattattat gttgaggtgc  30060
cttgatataa aaatttttct taaaggagag gatgcctaaa acaggcatta cctgaaacct  30120
cctctctcca gcattggttg tcttctgtca tgactcaggg ttttcactga gaatgggatg  30180
gaaatgtggt ctaaagatag ggccaatgtt gggactggat cccctctggg aagtcagacc  30240
aggctagggc aggtccttga agccatcagg aaaagcctct ggagccagaa acaaaacaaa  30300
aaaaaaatgg tgttaactaa actcagtctc aaatcctgaa taggactcaa gtcaagcaaa  30360
ataattaaag gagttagcaa agggcaagtc agagagaccg agcaacacca atgtcttccg  30420
ggagccctgt ggcgagtgac agagcctgga ctctggagta gaactcatct tgtgtcttct  30480
tctgccactc gttagctggg tgaccttgag ccaagcccct taacctcttg gaccctatgt  30540
tcttatctct aagtaggggc tggtaatatc ttcccctttg aggaatgccc tctaaggggt  30600
gttgtgaaga ttcggtaagg tggcaggggt aggactcctg gccagaaaca ggcacataat  30660
aaatgctaag tctctccttc tctccacctg ctggatgctg tagatactaa ggatttcgat  30720
gtgaatgaga caaaacccct gccttccagg agcctttgag aatcagagaa ctagacccat  30780
ttccagaaca aggggatgca gggtctggat aaagttttgg ggatcaatag agcagagggc  30840
tcccagagga tcccataggg ttgactccta actcaagggc atgagacaac ccccaggaag  30900
ggcaccctgg aaggggtccg gctgtccctg atttacttgt gggcactggg ggaatgcccg  30960
gagccatcca gccctcaggg ctctgtgtga ttctgggttc ctcccataaa agataatcag  31020
attctttcac gttaatgtct ttctccacct cattgcacat catgcagcta ttcattgact  31080
cagcaagtat cagctttgca tgcgaccttg gcctacccac tttagctttt agtaatagct  31140
cccttcttga ataatacaac cagtggggaa acagaaccta actcttacct ctgggaggct  31200
tatttgcttt gagaacatat gtcctgcagt tttgttcata tggcagtgaa gtttcgtgca  31260
cacactctag agccaggcag cctgggttca aagcgcagct ctgccaggtc ctaactgcat  31320
gaatttgggc aagtcgctca acctctccat gcctgagttt cctcatctgt aagattggag  31380
caatggtaat acctgctttt tagggttgag aagagaatta aatgaattaa gatgggtaaa  31440
gtgcttagag tggagctttg caagtagtaa gtgctatgta agtgttcgat ttaaaatgaa  31500
agacccttaa atacattctt tgttcatttc acaagccctt catttcacaa ccttacattt  31560
cacaaccaag ctctgtctcc cctggaatcc agccataact ctgctcacaa gtgtgagaca  31620
ggccccagca gagctgcacg aagaggagag aaggcagccc cccagactcc caacccccctg  31680
tccaagatgg caaaaccaga acacagcctc tgtaccaccc cagcaggtat tcagaatctg  31740
caatctccaa agcccacttc aattgtaaat gtagagccac gtgcgcttta agtcacctgt  31800
```

```
cactctggag gctcttttgc tcagttcctc accattagca gggatgacag ggagtgcagg  31860
agtgcggtcg actcccagat attggagagc gctgggctag ctgcccattc tcccggcctc  31920
cactcctctt tgctgtccag ccatcacttg ctctttgaag gcaaacaaaa cagaaaacag  31980
tgccaaaagt atgggaagaa agccagcttc tcccctgggg tgcctgtgat gccatgccca  32040
ccctccctga ccacgcagcc cctgtggacc ctcagggccc caagccccca tttccatcac  32100
atgcgtacac ccatgtgtgt ccatagccgc ccatctcagt caataaggct gctcctgccc  32160
acttggaata gtggtgacaa ccaggagtgg cttatgggaa ctatcccaat ggcctgacag  32220
catgtccgct gcaaaccgct gaggtaggac actgccctca tgtctagctg atcagcaaga  32280
ggcgcagttg ctttcttagg taacattgct gctgtgtcct ggccattgct ggggggtggc  32340
acttaatcta caccagattt ttccctcctg tatcttccaa gctgcttgga tcttggtgct  32400
gaattaggtt ggactttgtc ttgtggggaa gggaggacta tagaccctca acgtaagcaa  32460
tggtcagact attctaagaa aactcgccga attaaagcat gaggtaaatt tagttctgac  32520
ttctgtccac cccactgcca ctgtcccctt ttatcccatg atcccttgct tttcttttcc  32580
tcctctctcc ctatctcttg tgtttgacgc atgataggaa ttcagaaata tatgtttgtg  32640
gatttgttta ttcacgtagc aaaccatttc ttgagtgcct accatgggcc aggtagaatg  32700
ggcggccccg ggctgcagtg gtttcttcag cccctctcca gggtttacac tgtgcaagac  32760
ggtttgtgat gggtcctccc atcgaggacc acactcttct ttctctgtgc cccttggtcc  32820
tcagtctctg accccacttc aaaggcagca ttcactcagg gaagctccca tacaatgcta  32880
gtcagagtaa aagtttggac aaattgccag gaagcagctt gtcagtatgc ataaacagcc  32940
tttaaaatat tactactctt tgacccagaa tttcacttct aggaatctgt cctaaggaag  33000
tagtcacatg caaaagattt atgtaccaag atgttcatca aagtgttgtt ttataacagg  33060
aagtctcaga agctggataa atatccaacc tctggaaatg gttagataga atagtatgta  33120
gccattagaa aattatgtct atggggttta aaatgtcatg ggaaaacact tctgacataa  33180
aagagcatga gaactgtata tttagcataa tcttaactat gttttagaat gcacaggaaa  33240
aaaatgtaca aacatattca tagtgatgtc tctggtggta ggattatgat cagtaagtac  33300
ttctgtctct tcatattttc ctgtatttga taatacatgc atatgttgtt tttaaaataa  33360
gaaaaatttt aagtttaaaa ttggagctga aaagtgtttt taggtcaggc gaggtggctc  33420
acacctgtaa tagcaccact ttgggaggct gaggcagtca gatcacttga gcccaggagt  33480
tcgagaccag cctggccaac atggtgaaac cccatctcta ctaaaaataa aaaaattagc  33540
catgtgtggt ggcacacatc tgtaatccca gctacttggg aggctgaggc atgagaattg  33600
cttgaaccca ggaggtggag gttgcagtga gccaagatcg tgccactgca ctctagtctg  33660
ggcaacagag taagactcta tgtcaaagaa aaaaaaaaaa gaaaagcctt tttaaacagt  33720
agcagacata actatataat ccttactaag ctgtcggtca aatttttatt tatatattta  33780
ttttattcat ttattatttt tagacagggt ctcactctgt tgcccaggct ggagtacagt  33840
ggcgtgatca tggctctctt caaacttgac ctcccgggct caagtgatcc tcccatctta  33900
gcctcccaag tagatgggac cacaggtgca taccaccaca cctggctaat ttttttttatt  33960
ttttattttt agagatggtg tttactatgt tgcccaggct agtctcaaac tcctgggctc  34020
aagctatcct cccacctcgg cctcccgaag tgctggggtt accagcatga gccactgtac  34080
ccagccctca aatttttaaa aatctataag agacattatt ggacaattag agaaattcac  34140
```

```
atatggactt ataatagtat cagagtgtgt ggtgtgatgg ttctggaggg aatggacttt  34200
ttctttggag acaggctttt ctatgcccac ccttttatct tgctaactta tcatcatcca  34260
ggttccagca gaaacattac ttcccccagg aaatttctta agggtgcagt atcatgatgt  34320
ctgcagcaaa ttctcaaata gctcaggaaa aaagtacgtg tgtggtatga gtgtgtgtat  34380
gtatgtgtgt atatatatac acatatatac acatatatat acatatatgt gtatatatat  34440
acatatatgt gtatatatat acacacacat acacatatat atacacacac acatacatac  34500
atgtattttt atataattat atatgcagag agtgcaaatg ttgccaagtt aaagattggt  34560
gagtctaggt gaagggaata tggtatttat tgtattattt gtgcaacttt tcttaagttt  34620
gaaaattttc aaaacaaaaa attggaggaa gaaggcatgc cagtctaccc caagccctcc  34680
attggaatgc tgaaaatcta aacaatgtga tttggcaatt tcatttcttt tctgttgtgg  34740
gccagtagtc cttagatgtt ggggaagggg gtagtcgctg aggtgtggtt gacttaggat  34800
ggaagaagca gaagtcaaga ctcccagggt caaagtggtt tgctctgctg acccaagtgt  34860
gggaggccca gagtcagcgt ttcaggtgtg ctaattcagc atggttctat tcacggccaa  34920
agtccaccct gggcacctct ctggcagcaa tcttgggtga ctctactaag gccaggcctc  34980
catgacccta tgtctggatc ccatatctcc acctctccca ctgtctcagg aacggtgctt  35040
agctttttct tttccctctc ctgtcttctt tgccagcatg tagaaagttt aaataattcc  35100
cctctttaca acaaaacaaa acataccccc ttcagtcaac caccctagct ctcttctcct  35160
tttcccagcc agattttttt aaaagcatcc taggccaggc gcggtgactc acgcctgtaa  35220
ttccagcact ttgggaggcc aaggtgggtg gatcacaagg tcaggagatc gagaccatcc  35280
tggctaacat ggtgaaaccc catctctact aaaaatacaa aaaagtagcc gggagtggtg  35340
gcaggtgcct gtagtcccag ctactcggga ggctgaggca ggagaatggc gtgaacctgg  35400
taggcggagg ttgcagtgag ccgagatggc gccactgcac tccagcctgg gtgacagagt  35460
gagactccgt ctcaggaaaa aaaaaaaaaa aaaaaaaaaa agcatcctca gcactttggc  35520
aactccatct cctcccaaca tgtccctgtt actggaatcc agccaggact cagccccgat  35580
ctttctactc taaccagttg tctcagttaa caaggacagg tttatgctgc agtgacaaac  35640
aagatcccaa attcttgtgg cttcacacat ctggcaccac ctcatcttcc agccttagga  35700
gtcatctttt agttccttga aaactcttta cagttttctg ttggggcctt gtcatatact  35760
attcccctgg aatgttcttt cctatcccct ccctttcacc ttgctaactt gtgcccatcc  35820
ttcaggtctc agcagaaaca tcacttcctt ggggaagttt tctccaacac ccacactaca  35880
caggtgtccc atctacactc ctatgacttt gtggtacttg tctcacttca ttttccactg  35940
ccttccccac aaggcacctg cacaagggca aggaccgtac cactgtacct atgtcactca  36000
ttgctgtggt cacctgcact ctggctgcct accttaacta cacattagaa tcacctgagg  36060
agcttttaaa gccacaatgc aagactccac cctaggccaa ttggatccaa atccctgggg  36120
tagggccaga catcagtgga gttatatata catatatata ttttgtttgt ttgtttgttt  36180
gtttttgag acagagtttt gctctgtcac ccaggctgga gtgcagtggc gcgatcttgg  36240
ctcactgcaa gctccgcctc tcgggttcac accattctcc tgcctcagcc tcctgagtgg  36300
ctggaactac aagtgctcgc caccacgccc agctaatttt tttgtgtttt tagtagagat  36360
ggggtttcac cgtgttagcc aggatggtct cgatctcctg acctcatgat ctgcctgcct  36420
catcagcctc ccagagtgct gggattacag gcatgagcca ctgcacccgg ccatcagtgg  36480
atatattttt aaagcactgc agagaattct gttgcatcag cttgagaacc actgatctgc  36540
```

```
cttgtgcttc acatttaaaa cttttttttta atgaataaat aaaccccaaa aaattaatct  36600
ccctaagcct ccctagaaga taggatggta aggatatttt cctaggtaaa aatatgttaa  36660
tttcatattt catgaaattt catgtttcat ttcaatcaag ctctgtcata caccttacat  36720
ggggcaagcc cagtgcctgg gcagggtgta attatactca ttacacaggc aaggaaaagt  36780
cacattaggt gatggagcac aaataggcag ttaatggttt cagggctagt taggatatgt  36840
ttgtctttca attgcaagta atagaagccc aaagaaattg gttatttata taatataatt  36900
gattggttcc caaatttgaa aaattcagga atagacccag cttaggtaca gctggatcca  36960
gtcactcaaa caatgtcaca aagaaccctt tgacaggaat gtatcctgtg ttgactctac  37020
tttgctctga gtagtctttc cccaggtgat gataaaaatg gtcatcatcg ccaggcttgt  37080
gtcctgttta gtaggaatat acaagaagag ctcagtaaat gctggcccca ccactaagca  37140
aaaacaaaac ttttgttgtt gttattgttg ttttaaataa cagcttagac ctttcttctt  37200
tccttgttat tctctttcat ctgtaatcca gttttctact tctgaagtat agaatgttct  37260
gatgatttat tcttcattac ccacaacttg cacatgttta tttaaaaatg ccaggattgc  37320
ctggccgttg tgtgctgtta acctttgttt gctgttagtg gatccctgaa gttcaggctc  37380
ccaggggagc agataatggg tatccagttc ctgcaatatc caccctctgg caagccaagt  37440
tccttcctgg gtaaggtttt gcctacctgc attcctaggg aagtttctgg gcctgaccac  37500
caagccagct ctgagaaggg gtgcataagc cccaccatgc tttggctctg tccctataga  37560
atattttatg ttgttactga aaactaaagg aagatgggtg cggtggctca tgcctgtaat  37620
cccagcactt tgggaggcca agacagattg atcactcgat gccaggagtt caagaccagc  37680
ctggccaaca tggtgaaacc ttgtctctac aaaaacaaaa caaaacaaaa attagccggg  37740
tatggtggca tgcacctgtg gtaccagcta ctcaagaggc tgaggcacaa gaatctcttg  37800
aacctgggag gtagaggttg cagtgagccg agatcgcact actgcattcc agcctgggtg  37860
acagagcaag attctgtctc caaaaaaaaa aaaaaaaaga aaaggaaagc taaaggagag  37920
agactaaaat gatatcaggt tcctggagaa caaacagaca tgattttgct tcatggcagg  37980
acagccggaa gaagtgggat tatatcctca cattacaaat aagaaaactg agactcagaa  38040
tggttaagtc acttgtccca ggccacacag ccagtaaatt acagaaacag aatttgaacc  38100
caaatcttcc agctccaaag cttgtgttct tttcactacc tcctgcttaa ttttttaatt  38160
tctaagatta gacccttcat ctatccatga cacctgcctg tcatcccctg aaaaaaggtg  38220
aacgccgttc agaaattttt ctagcctgag ctcactccca gttcacttat ttttgctttg  38280
tcatggctgc ccagtcccca cttgtagacc aggaataggt catggctgcg gggactacac  38340
gctgtcgctg ctgcaagggc cggcctctgt ttccggggct gagtgggggc cagacctgcc  38400
aggagcacca tcttctgtgg gtcctgcctg gatgtcacat cccggcccca agaagtcact  38460
gcaaaccttc gtattattga gcttcacatc ctagaatttg ctgtcactgt ggctgctgca  38520
tgaagttgtc ctgagagaaa cgggcattgt cattaacagg gaaattgatg gtctggggga  38580
aaagtcatcc tcattctctt gcagatctat gggtgattga gactggctga tgttgaaggg  38640
gtttctcagc catcgtgtgc catgttatgg aacagtggtg tagccagcca tttgacaccc  38700
agcgctgacc tttgtttaac aacctcacct atatatgaca aaatgattgt cagaaataat  38760
cgtgtaatga aatgactgta ataatggcca gaaaagaaac gcagatagta aaatgtttct  38820
cttgttgaac tctgtacata taattgcacc aggatttttt tcaaataaaa agtaaatatt  38880
```

```
atactacaaa aaagggaaaa agcacaagca tttattaaat agctttctat atctttctga  38940
gttttgatcc tttgattgca gactgatgta atattttatg taaatcattg cttggttact  39000
aagtgaactt taagaaaagt gagacgtctg cagaagttgc ccataattta gcagctactg  39060
tattgtacca ttgatgtacg gctttatttt cttgattaat tatttaaaca atataattca  39120
caattttaaa ataataaatt tccacttaaa atggtattta aactcagcaa aatatatcat  39180
ctatgagtaa aatttgtatt taccaagcaa aaatattaca gtttgtggtt cacatgctgt  39240
ctcactgttt taaattttaa atacaaaaac tccaagtagg ctgggtgtgg tggctcacac  39300
ctgtaatccc agtactttgg gaggctgagg caggcatatc gcttgagttc aggagttcaa  39360
gatttgcctg ggcaacatag tgagatcctg tctctactga aaacaattag ctgggtgtgg  39420
tggcacatgc ctgcggtccc agctactcag gaggctgaga taggaggatc acttgaaccc  39480
tgggggacag aggttgcagt gaggcaagat tgcaccactg cactccagcc tgggtgacag  39540
attgagaccc tgtctcaaaa aaagaaaaaa aaaaaagaaa cacaaaaact ccaggtggtc  39600
gcacagaatg acaggactga agtaacttag ctccaatttc tgtcttcata atcactgtcc  39660
taccattgtc tgtgcttaga atctacttgc ttaatgcagg aacatgtgtt ctcacagaga  39720
tggaaaatgc aaatggcgcc agaagcaagc tggaaattct gaaccattaa gaatttactc  39780
tctgccaggc acggtggctc acgcctgtaa tcccaggact ttgggaggct gaggcaggca  39840
gatcatctga ggtcaggagt tcaagaccag cctggccaac atggtgaaac ttcatctcta  39900
caaaaataca aaaattagcc aggcatgatg gtgggtgcct gtaatcccag ctactcggga  39960
ggctgaggca ggagaatcgc ttgcacctga gaggtggagg ttgcagtgag ccgagatcta  40020
tctgcaccat tgcacttcag cctgggagac agagtaagac tccatctcaa aaaaaaaaaa  40080
aaaaaaaaag aacttactct caaaataaat acgtgtggct gactccacat atggtagggc  40140
caactgtata actagaagtt ctccaaataa cttctgtgga gaaaaaaaag tttattaaag  40200
gttaactttt ttaaagtgct aactagaacc ttactaacac tgagatcgca ccaattgttt  40260
ataacttaga cagggccggg tgcagtggct catgcctata atcccaacac tttgggaggc  40320
cgaggcaggt ggatcacttg atgtcaggag ttcgagacca gcctaaccaa catgatgaaa  40380
ccccatctct actaaaaata caaaaattag ccaggcacgg tggtacacgc ctgtaatccc  40440
agctactggg gagggtgagg caggagaatc tcttgaaccc aggaggcgga gattgcagtg  40500
ggccaagatc gcaccattgc actctagccc cagcaacaag agtgaaactc tgtttcaaac  40560
aaacaaacaa aaaaaaaaac ctcttggacc aggaaaatat tttttaaggg aggagtattt  40620
tatcactggc attgtttagg attgcaggca catgatgcta atgaaaagca gactaactat  40680
tagttggttt tattactgtt tttgaactct ctctctccct tttttttttt tttgagacag  40740
agtctctctc tctgtcaccc aggctggaat gcagtgactg cagtctcagc tcactacatc  40800
ctctgcctcc tcagttcaag tgattctcgt gcctcagcct cccgagtagc tgggattaca  40860
gggcaccaca ccaggctaag tttttgtatt tttagtagag gcagggtttc accatgttgc  40920
ccaggctggt ctcaaactcc tggcctcaag cgatctgccc atcttgacct cccaaagtgt  40980
tgggattaca ggcgtgagcc accgtgccta gccctgtttt tgaactctct agagacagtc  41040
cagcccctta ttacttgtcc tgaggcagct gctcccttca cctggccccc cgcattgtgt  41100
tccggaccct tgtcctggtg gtgctaaaga atatctctgt cgatcctttg gggactgggg  41160
aaactgaggc ccagtgccac gcgatgccat ttgttcaggg aagattaggt catctgctag  41220
gtccccagtc acttgacctt cttcccagac aggaagaagc tgctctgggt ctctcagtgc  41280
```

```
tccacgtgtc tttgcacatt gaaatgtttt ctgatttttt tttttttttt tttgctgtta  41340
catttacttt taaaaaataa caagcaataa aatgttacat ttgagaaggt tgaaatgaga  41400
attgatttga gttaaattct agcagatttt tcttagaaga atgatatcat catctccagc  41460
tacctgcaat tgatctactc tgaattaaga aagagacttc catttgttgt ttatattttg  41520
cactcttgat gtgtttcttt aaattatggt catgggccag gtgtaggagc tcacacctgt  41580
aatcccagca ccttgggact ctgaggaggg aggatcactg gaggccagga gttcaagacc  41640
tcgtctgtac agtaaatttt aaaaattagc caggcatggt agcattcacc tgtagtctta  41700
gctacttggg aggctgagat gggaggattg cttgagccag aactttgagg ctacagtgag  41760
ttattttcac gccactgccc tctagcctgg ctgacagagc aagacctgcc tcaaaaaaat  41820
aagtaaaaaa taaattaaat ttcaatcatt agcagtcatt aggatattta aatacagtat  41880
gttgaatcaa agttacgcat gtgtgtattt ttttttccag agagttgttt atcatgtggg  41940
ttttaattta actttaaaaa aatgttggct ggacagttgc ccaaatggta tcatcagcca  42000
tttggttgag aacgtatgtc ctgcgggctc ctctgtcact ggagttttgc tagctgacag  42060
ccactggcta gttagagact gcagtcagca cagatgcagg cgtggacttg cgcacgtaac  42120
catgtcaatg caaagccatc acttcttaaa aattctgaac cctgctgtct gagatggtgg  42180
tgcagcggat agaactctgc tctaagaggc agtagctaat tccatgtctt ctttgccctt  42240
gactagctga gtgactttgc acatggggct tgcctctctg ttgccttgtc tgcaaagtgg  42300
aatcatcttt tccttgctag acagaaggtg gaccctggac ctatggcctt tttgagtttc  42360
ccccccgctt cttagaagga cctctgatcc tactgagttt aatacccacg ggttaataat  42420
tgggaaaagc aaaggaagcg cttctgttta ggtaattata tgcatgtttt tgtctttttc  42480
tggctggaaa gatatccaag ccactgggaa ggtccgtggc tacccagggt agccctctct  42540
ggggagggct gctatatcca agagcccctc atgagaattt gaaaatcgac catggtaggg  42600
cctgctgact tttgacagct aatggtgtgc tgagaattgt ccctccaaag atgcctttcc  42660
attccctcgg gagagtctgg gcagccccta ctgggggctg ggatgctggc tcttccctca  42720
gcctccaccc caactgctct cttccctcct cccctcccca gcccccctaat ttctctcaca  42780
aggctttgtt ctgcagcaac ctttcctaat gcagtcctgg cctcttcgca gcttcattac  42840
ataaccttcc gtggactcct ggtccaagga tcaccccaga aagccagtca gaggtaggca  42900
cgcagctggg gtccatttac ttaccttccc cacccccctcg gaactcagag gtggtgcagg  42960
aatttggact ccaagaatta acagctccac caccatcacc agagccaaaa ctcaggatgc  43020
atgtgcttca tctgctgctt atttccagct gagagccagt ggtgccatgg ttccttaggg  43080
agccggtccc ctgatgccgg ctcctggccc caaatctctc tgatccgggc tcttccagaa  43140
tgtcttgtct ccaccatcgc ctttgaccaa tggtgtccct ttgcctggta atgtcccctt  43200
tgcctgatga tggccctgtc actcctctct ttagcacaga ggaggctgtt tcatcccttc  43260
aagcctgccc tcccttcaag tcttagctca agttcacctt ctccgcagag ccttctccaa  43320
tcttcttgac tacgtctcct ctcagctcca gcaacctctg tctctggcac tgattcctta  43380
cttagctaag agaatcacag acacttgggg ctcaggacaa tctgctttct ctcttcttac  43440
ccatggcctt ggactgtgtg tacctctttg tctccactcc caaacccaac ccccagaggg  43500
cagagagcat gttgtctgtc cctttgctca gcatgaagcc atgcgtgtgg tagatcggca  43560
gagttccata acttgtgttg accgaggggt cactttgctc tgaaattacc cctgtgtcct  43620
```

```
tcagtatttg cacagatagc ttcctggcca gaccgaatat atccaagggc atggcccacc  43680
tctgctcctg tttccaggtc cctggtgggg gttagttcat gccttcctca taatctgccc  43740
actggcctgg tcctcaaggt cttcccaact gctcagccag agttgagaaa atgggtcgct  43800
ccatcctgtt tgtgtcgttc tctccttcct ggcccactct cctgcccaca ggtatccagg  43860
ggctgcctgt agcattagag gacatacatg cacatgcgtg ggcatgggac actcacgtag  43920
cctccaagca cagcatcaat aatgcattct gtgctttata gcatggaaag ctgctctaaa  43980
ctttattaca cagtggacat gtctgaagca gctcccaaat ccacccctga gtgtgttgga  44040
attggcaagc ctatcacttg ggagtctagt ttttttgttc gttaataata gatgcttcct  44100
gtggccccag cttggcaatt ttgatttaaa gtgatcttaa ctgaagagac taatggacgg  44160
gtctgaattt gtgcctttta agcacaaagt attgctctta attaactgga ttctatcctt  44220
tgagcaggca gaggccttcc cccaagggcg tcattaacga tccacatctg gacatcttcc  44280
aaagccttct tctgtttcag gccaaccgca ggtgtgttcc tgaacaccca ggaggctatg  44340
agagccacat atgcctccca aatacacaca gtgtgcatgc ccagggacat agagcagtgt  44400
gcaaagtccc attccatctc tctccacctg ggagaggatg gctcttctgt ctgattcatg  44460
gctcaaagtg gtaaaggagc tccccactcc ccgtcccacg cctactcaga gtctgcaaat  44520
atgtatgcga tatgagagct cgtcagttag ctgtcttcag tgtggcgcac atttgaggag  44580
tctgactccc ctccagcaca ggccaatgtg cactgctctc ctatctttgt acccccactg  44640
ttgcactgtg cagaggttgg agccatagaa gtaccagagc tgtgaaagga gaggccccct  44700
ctcacctctg ccctggtctc catccccact ttctctagga agctagtagg tgctgacagg  44760
ggagagaagg gaggggaggg gtccagaaac agtggctcat gcctgcaatc ctagcacttt  44820
gggaggctga ggcaggagga tcatttgagg tcaggagttt gagaccagcc tgggcaatgt  44880
agcaagaccc tatctctaca aaaagaaaaa atgtaattag ctgggtgtgg tggtgggcac  44940
ctgtagtcct agctacttgg gaggatgagg tgggaggatt gcttgagccc aagagtttga  45000
ggttacagta agctgtgatt gcaccactgc actccagcct gggcaacaga gctgagaccc  45060
tatctcaaaa aaagaaaaaa aaaaagaaag gagagagaga gaaagaaaag aaaagaaaaa  45120
aaaaaaagaa gggaagggaa agcccagaag agtgtgggga gaggaggcgg ccgtcattct  45180
ggggccctca gtgtgcacaa ccagataaca catgctctgt gggcttttgt accattttgc  45240
ttgagcataa agaaaggaag gctgccccta aatagaaagc actctggagg caaacaaatc  45300
tgactccaat cctggccctg ccactttccc agctgaggac ttagacaagc accctagcct  45360
cttggacatt ctcagagcca tctgctgcaa gtgggtgctg ccatacccac cttactgggc  45420
aggcttgggg gaccaagggt ggtaaatggc tcagtctttc atgatgcggc cacacagcag  45480
gtgcgccatc caggtccatt tctttccttc ctttccccca aatcaagttg tcattaaagt  45540
actagtccac attaatgaaa tcaactgtat taattttcta tttgctgcta taataaatca  45600
tcagaaattt agtggcttaa accaacacaa atgtattacc ttacagttct ggaggccaga  45660
agccctccat aggtgtcact gggctgaaat caaggttttg gcaaggttgc ggtcctttct  45720
ggagggtcca ggggagaatc cattttcttc ctttttccag cttctaaagg tttcatgcat  45780
tccttggctc atgatcttct atagctatag tcagaaaaat tttccatcaa tcatcttcaa  45840
agccagcaat ggcaggatga gtcctcacat caccttgctc tgacaccagt tctctgcctc  45900
cctcttccac atgtcaggac cctcatgatt actttgggct cactctgata atctgggatg  45960
atctctctat tttagagtca gctgactggg aaccttaatt ccatctacaa ccccaattcc  46020
```

```
tctttgccat gtacagtgac atattcacag gttctgggga ttaggacgag cctgtctctg  46080
aaaggctact ttacatgaaa attcattttt ttaattaaga tttttttttc ctcttgagac  46140
aaggtctcac tctatggttc aggctggagt gcagtggtat gatcacagct cactgcagcc  46200
tcgacgtctc tgggctcagg tgatcctccc acctcagctt ccctagtagc tggaactaca  46260
ggggtgagcc cccatgccca gctaattttt tttttttttt ttttttgaga cagagtctca  46320
ctcagtcacc caggctggtg tgcagtggtg caatctcagc tcacagcaac ctccgcctcc  46380
tgggttcaag tgattcttgt gcctcagcct cccaaggagc tgggactaca ggtgtgcacc  46440
accacgcccg actaattttt gtatttttag taaagatggg gtttcaccat gttggccagg  46500
ctggtctcaa actcctgatc tcaagtgatc caccaacctc agcctctcaa agtgctggga  46560
ttacaggtgt aagccaacat gcccggcccc agctaatttt taaatatttt ttttgtagag  46620
atggggtttt accattttgt ctaggctggt cttgaactcc tgggctcaag caaacctccc  46680
accttggtct cccaaagtgc tgggattaca gcatgagcca ctgcactcgg ccttaagaga  46740
agatttaata attaatactt tacaacaaga tctggaagag gtgggatgag taactaaatg  46800
aggatacaag taacccgggt catatttgct aataccettg gtcacattga acttgatatc  46860
ttatcagatt ttcctaatca gctcctttag cagcagtgtt gcagcatctt atctcatttt  46920
gtttttttgtt tttttgccta gcacatgcct gtaaatcact ggattgaggt gtttagatgt  46980
ttgttgtcct ttggatgctt cttataaatc catatttcat ggctccctgg aaagtgctat  47040
gcaaatgata agctgcaagg atggaaagga aattgcagtg ctcctgaatt gtaaatgggc  47100
ttttacgagg aggtttctaa ttactcgctc tttctcttga actgaggagt tgaagtgtag  47160
gtggcagatc cataacagat aatcatgtgt gtgatgtgac ttcagcctga gcgtcgagga  47220
ccaagtcaca gagcaggaac agccactctc cagtgtcctt ggggctacgt ctgaggagaa  47280
cctgggattt catatatgac ctgcactggc tggggggctc tcttgacgta acgtgttccc  47340
tctgagcatg ttacagattc tgacattctt atgttccttc tgtggagaga catgtactta  47400
gtgacctaac tcactttagc atatttttgc tcatcgtttg tgtagcttaa aggaatcaga  47460
taattacccc ctccccacta ctttcggaag cacaaatgca atgccctaga attgtactgg  47520
ggactcaaaa agaaaagaga gtagtaaaat ctattaaagg ggacaaagac agcctatata  47580
ctacaagctt tctattttta tggcagagaa tgccattttc taagtaaaca gagaactgca  47640
tttgacctgc aatatcaaat gcatggattt gatgctttgg aaagcaactg ttttctgcgt  47700
taatctgggt gtcttccgtg aaatgtcctc ctgcctttgg cttaaacact agctttgtct  47760
acagccattc catcctgaac ctgcccaatc ttgtctgaat cctggtttca ccactgacaa  47820
gctgtgtgtc cttgggcaag ttacttcacc tgtctgtgct tcagagtcct catctgtgag  47880
ttggggaatc tggacagaat ctaccccata gggcgtagtg aggatgtgtt gaattatccc  47940
aagtggctac acagagtaag cactcaaatg atgtcatcgt tgtcatgatt gctgttacca  48000
gagcctagag ttcattctga tactcgagtc tgtggcccat ccagcccagg taaggaatag  48060
ttggaggagt tgggcatgtt cagcttgaag aggagacgac aggggatatg ggatagttga  48120
atctgtgaag ggccccctgg gatgaagaac tggcatgttc tgtgtggctc cagggcactg  48180
agcaggaccc atttgccaaa gtctcaggga cacagtttct agctatagac agaaaaattt  48240
tctgtcactc agaggatgaa aatagaatga gccccccttaa gaggtaatga gctccctgtc  48300
attggaagga ttccagaaga gctaggtaac cactttaggt gctatcaagg ggcttttttc  48360
```

```
tttaaagtcc tttccaaaag cttctgagat tgcataaaca ataggaagcc atcttggtgc  48420
tttaacacaa actctcccca gtgatgaggg ttgagccaaa gccagattgg caagcagaga  48480
ggagacttgt gtacaaggag ttcctcgagt caattgcttt ttccttgttc tagccagcca  48540
gagggctcct gttggaaaac aggagaccgg agaggctgag gcctgaccaa accagcttct  48600
gcaggccagc tgggaggcca caactcctac ctacgggaaa actgaagggc atctctattt  48660
ttagattagc aaaagaaaat aaatttaagt ttgagtctcc tttgcaactt ttaaaagaca  48720
tctttattga gatgatcatt cacattctat aaaattcccc cactttgagt tacaattcag  48780
tggttttagt cttccttgat gattttgatg gtcttttctt aaggctcttg gaagacccag  48840
aagcctctca gacacaggtg ggtgtggagg gcgtagcaca gaggcagact tctcatttcc  48900
tgggtctccc ctttaatgac tctcagagac ccctccttcc ccctgcccct ggcttctacc  48960
ccaggggtgt agagttttgc cattttccaa gcagaacttc atttcctctt ctgtgtctac  49020
actctttgtg cttctttctt gccagctttt tctcctttgc ccgcccttcc ttccttcctt  49080
ccctccctcc ctccttccct ccttccctct ttccctcctt ccccccttcc acccttcccc  49140
ccttcccccc ttccctcctt ccttccttcc ctccttcctt ccttccttcc tgccttcctt  49200
ccttcctgcc ttccttcctt cctgccttcc ttccttcctt ccttccttcc ttccttcctt  49260
cctggtatgt gactaatttc tgtttcagga cataaatgtt gtccaggctg ttctttggtc  49320
tttctgttgg ataatggaca tttggcattg agagaggctg ctttttctga aatcatgttc  49380
ttggggccca gaacctaggt gtgtgcttct gactttgttt tcttcctgat ccaaattctg  49440
atatgtccat ttaaattgat ctagacccac agggcactgt gggacagatc ctcagtggaa  49500
catgactctg taacgagagc attttgtttt gtcaaaatga gaacatatta ttgcctttca  49560
tctgattgta aacataatac atgtttataa aacagtataa tgagacaaaa atgtagacac  49620
taataaggga aaatctccct aattgtattt ctcttcacag agaaagcccc tgttgggcat  49680
atatactcta gtttgtttat ttgtttgact acacatatat gtattctttt cttatgtata  49740
aaaattctga acatgcacat ttctgcaact actgttttca cttgatgatg catggacctc  49800
tctagagtgt acgtttcttc ttccttacaa agcagttggc ttcgcccagg gtacaccagg  49860
acacggtttt ggctctgtcc ccagggtgtc acgggaccag gggatgatct cacagggtct  49920
gccatctgcc ctgcctggcc ggaggctgca tcgagagggc caaggggcac cacgtgtcgt  49980
gggtactgtc aaacaagagc cttcagagcc ttccacagtc tttcttttgc ttcccagcat  50040
tgcttccccg ctggtggact ctgaatctag aactagctcc aggcgcctct ccaaattcag  50100
acgggagctg gggcactatt ataatgcaaa tctaggcaaa gccctcccaa taccaggatc  50160
cagaatgggg tggggccctt tgccctgaaa agctgtttag tttgaaaata caaacaggag  50220
acagaaaagt ttggctaaat taatggataa agttttaacg atggtaacca tagtagggtt  50280
catcgacagc cagcgatggt tctgaacact tgacatgtat taactcacct aatccccaca  50340
ttttacagac aatgcaaagg aggctctggg aggttgagtg acttgcccca aagtcgcaca  50400
gctcctaagt gaaggattcg gagtggactc caggcagcct ggtctgactc cctgcactgc  50460
gctgtgctta tctctggccc caatgccgcc atgcagaagt gtctgggggc actttgtctc  50520
tgtcagacag aattcggaga tgtgtatgct tgccctggta tggcacttct ctttttttga  50580
gacagaatct cactctgtca ccctggctgg agtgcagtgg catgatctca gctcactgca  50640
acctccgcct cccaggttca agcaattctt gtgcctcagc ctcccaagta gctgggatta  50700
tagatgtgca ccatcgtgcc tagctaaatt tttgtacttt tagtaaagat gttgttttgc  50760
```

```
tgtgttggcc aagctgatct cgaacttttg gcctcaagtg atctgcctac ctcagcctcc  50820
caaagtgctg ggattacagg catgagccac catgcctggc agtgtggcac ttcttacgtg  50880
tgttcagcgg acactgttta tcttctgtcc ctccaagacg gtgctgagct caggtcgttc  50940
attactggca gacaactgct gatttccaac agaattgcca tcctcttctc ccctgcgact  51000
ttcagagtgt gacctcagac tcaaaaatta gaagtgaaaa catcttaaaa actatcacct  51060
tttcttccta atcctcctct cccctccctg tcttccttgt tgtccccatc taatgaacta  51120
tcatggcaaa aagagcccat ttctggtcat tttctgtggc ctttcaaact cccacctacc  51180
ccactgctcc tgggtgcatt acccgaaagc tgagacttca gtgcagaaag tgccaggccc  51240
tctgtccccc cagatcgcct tccttgtctt ccctgtgctt gcctgtcaca ttgtgtgggt  51300
tccagcgctg gaaggaatga ggaacagatt ctctggttct ccttttgaag tttaccttcg  51360
ctccaccact tctgagacct tcccggaagt tgccccttgt ttctctcctc tccagggctg  51420
ccccagagct gcctctcacc tcttcctgct gtcaccccac caccatcagg gcagaagttg  51480
ggacaaagcc tctcctactg gctcctgctt ttctccctta ggtccagcct cctcttctcc  51540
atcttcagga gtctccttct ccactcacac gtcatgactt cagcacctcg catcagtcca  51600
gaatatgact gcttgttcaa gtgccacctt tctcatgcat ttttttctag tgacaatcac  51660
agccaccctg tggggcagga gtgtcatcat ccccatgttt caaatgaaga attgcagttc  51720
agagagggca agtgactggc ccagcctcaa cagctagcca gtggacccca ccagggcttc  51780
tgactccagt ccgggttccc tttccaccca aatccatgga gggagctgag ccgagaacag  51840
gtgtccttca ggaagacgtg aagccaaagc ctccacctcc aaactcaggg gcccagggag  51900
tccaggcacc catccactca caaggctgga tatggtgcat tccaggagag gggttggggg  51960
cgagtggcct ctctgtgtac ccgtggggat agatgcgcaa gtggcatcgc cacatcgtga  52020
gtcctggctt catgggtgag ctccaggtcc aacgagaagc caagcagggg gcccttcaag  52080
ctcagctttg ggcccgggtc ggggtacagg gtagagcggg cctccccagc ccctgccatg  52140
aggccaaggc agtgcatcgt tcgcagcgta cattcagaaa ccaaagccta ggagctggtt  52200
atcattccgg tttacagctg atggaagagc aggtgcttcc gagaacccac agtgctcttt  52260
ggccagtgac ccaagggtgc ctctgagagg cctcgcagca cccggaggtg ctgctgaggc  52320
aacgccctga ctgtaagaag gaccattcat cctcagagag tggccgtgat gctgctgcga  52380
cagtcccacc atccctcccg actctcactc ccaacagact tcccactgta aagctgaact  52440
ctccagcaaa tcacctctcg ccagactctc tcctcactct ctctgggtcc actagaggtt  52500
cctcagcctc tctttgcctt ggttttccca gctgtaaaat ggagcaaaga gggcctatgt  52560
acccacaaag gtgtggttgg agcgactcct cctacattag ggcctcgagt ggggcttcat  52620
gattggttgg tggaggtctc caaacccacc cagtgccacc gaaggctgag actgcagatg  52680
caatgccaca ggtgtccttc ctcagcctgg gcagctgaac atcatgtgta aaacggggat  52740
aataagataa taacagcccc ttgcacctat gtggctgtga ggattaaaca agataaatgt  52800
gtaacagtgc ctggctatag aaatatttac tcttgttatt aagggaagaa tatgtgtggc  52860
taaaaaggga tcgaagatgt aaaagccaat ccctccccct ctagcatatt taagggtaat  52920
gttgagttgg tttgtggacc atttgctgcc tgttagagct ggaaggtagg gaccccctct  52980
caacagcgat gctacaaatt atacccattg gaggtcaacc aaaagacaaa gcttattggc  53040
tggacatggt ggctcacacc tgtaatccta gcactttggg aggccaaggc aggcggatca  53100
```

```
cttgagatca ggagttcgag accagcctgg ccaacatggt gaaaccccat ccctactaaa  53160
aatacaaaaa ttagctgggc gtggtggtgc acacctgtaa tcccagctac tcaggaggct  53220
gaggcaggag aatcactaga acccaggagg tgaaggttgc agtgagccga gatcgcacca  53280
ctgtactcaa accgaggcaa cagagggaga cgcaatctca aaaaaaagaa aaaaagacaa  53340
agcttgttaa taccagcata ttgttaaggg aataaagtag gctgcagaac aactggtgta  53400
atatggtgcc atgtagggaa aattacatgt gtgcatagga gaggggtctg caaggttgtg  53460
ccctaagatg ttagagtggt tcctttgctt ttctctttta taattttgta tttgactttt  53520
aaataaggac cataaatcac ttttataaaa tacattctct ccagccccta ctactccttt  53580
aaagaataag agtggtttgc ccaagaaaga cagttttttt tgctctggtt ttcttgattc  53640
tgacatcaga ggaaactcct tctcatccac ttggggctct gggttcaggg gattcatttc  53700
aggcagatta aagtggtgac caggggcatt cgtggacaca gggagggaca ggagcaccat  53760
cagtttgtct cacacaacca ctgtcatcct cactgaaggc tgttgcctga tcaaaaacag  53820
tattgggcca ggcacggtgg ctcacacctg taataccacc actttgggag gctgaggtga  53880
gtggatcact tgaggtcagg agttcgagat caacctggcc aacatggtga aaccttgtct  53940
ctactaaaag ttcaaaaatt agccaggcgt ggtgggtgcc tgtagtccca gctacttggg  54000
aggctgaggc aggagaattg cttgaacccg agaggtagag gttgcagtga gccgagatgg  54060
caccaccaca ctccagcctg ggcgaccgag ggggactctg tcttaaaaaa aaaaaaaaaa  54120
aaaaaaaata tatatatata tatatgtcaa aaatggggta gtttttagat ctatagtagt  54180
tctaaaaaca aaggccatcc aagcatgaca gatttacaag cactattggc tattccagta  54240
gttacaatgg aggagagaag cttttagtta aaacaaacaa acaacacaac aaacccagaa  54300
accttaggtc aaaaccaaaa ttgtcctctc agacacaatc tgggaatttt ctcatgacag  54360
tgggcattag ccaactgaca tcagcagcaa ccatccgtgt gcacacagtg gcaccacctc  54420
ctcccaaaaa gcagccttca tctatgccct catacaatcg ttgattattc tctttggatt  54480
gaggcccgga attatttaag tttcttcttg ccagcatgag tctttccttt ctgtatgctc  54540
cttatcttct ctctttaatt tggcagttct gcttgaaatc tgggtctttc attagtagta  54600
gttcaatttg gttccagaac attctgtggt gtgatgcaat gtgaccagag ctcacacttc  54660
agagctcttc aagggccagt cttactgagc acctcccagt ggctgcctgt gtgctgggcg  54720
ccacttgtgg tgggcaggag agaggagggg acacaaaagg agacacagct ccttcttaga  54780
agctcaaagt tggggaccag ctgccacaga agagtatgtt tagcatctga gacaccaaga  54840
tccagcgtca caagggtgtt tattaagcct cctcatctct ttctttttct tttttttttt  54900
ttttttcctc aggcagtctt actctgtcac ccaggctgga gtgcagtggc atgatctcgg  54960
ctcactgcat gcaaccacca cctcccgggt ttaagcaatt ctcctgcctc agcctcccca  55020
gtagctggga ttacaggtgc ccaccaccac acccagctaa tttttgtgtt tttagtagag  55080
acagggtttc accatgttgg tcaggctggt ctcgaactcc tgacctcaga tgattcaccc  55140
acctcggcct cccagtgtgc tgggattaca ggtgtgagcc accgcgcctg gccttgctgt  55200
tgattcatct atagtatgtt tgacttgatg acctccagtt accttagaca gaggttctca  55260
tctaagctcc aactttccat ttcctttgtc ctcgtctttc cccttaaccc ctccacattt  55320
ctctcaaaat caccccactt ctaaaaaata ctgtttattt ttcttttaaa tttcaaatta  55380
tctatactca ttgaaataaa tcaaaatagc atggaataag cgaaaaaaat ggatcccacc  55440
cttccccact cccattccct agggctaacc atagttaacc atttaatgac taggtttttt  55500
```

```
tgttgttgtt atttttttatt tatttatttt gagacagagt cttactctgt cacccaggct  55560
ggagtgcagt ggtgtgatct cggctcactg caacctctgc ctcccaggtt caagcattct  55620
cctgcctctg cctcctgagt agctgggatt acaggtgcct gccaccacac ctggctaatt  55680
tttgtacttt tggtagagac agggtttctc aatgttagcc aggctggtct cgaactcctg  55740
gcctcaagtg atctgcccac cttggccttc caaaatactg ggattaaggt atgagccacc  55800
gcacccagcc ctcctgggct cttttccttt agttgcactc gctccccgct cctggagtag  55860
agggatttcc gagagactgt gggctccagc cttcacctag gcccaggact aggatgcctg  55920
ccctaacatt tatctttata ccttaaagca aaacagctgg accataagca ttcaagaaca  55980
aactgtgaat aaggagaaag ttctcccagg aaacaagagc tttagttatg ttgggccagc  56040
ccttatattc cttagctgtt accagtcact gcttgattta atctcggcta tcacttggcc  56100
tgacaggtct gctgctggtg ccaggatgtc tgggttttga agcctggctc cattacatac  56160
ttcctgtgtg accttgggca acttactcaa cctgtctgtt cctcagtttc cccagctgta  56220
ttatgtcagc ataatagttt gttgtgtgaa ttaaatgagg taataactgg aaatgcttca  56280
aacatggttc ctatcatgag aaatcctgct ttccgcctaa atgtgctgga aaattcctgg  56340
tggtgcagaa caggagacca gagcaaagga aagacagggt gcagaagcca aaaattacct  56400
tggagaacaa agcgcatgtt aaggttattt ttggattcta ggtttatctc tgcttggtct  56460
tcagttacct acaagagatc catttagggg atttttgttt gtttttaacg atagctttat  56520
tgagatataa ttcatatgcc ataaaagtca ctcttttaaa atgtttccgg tatattcaca  56580
aggctgtgca gccttccctg tccttgattc cagtctgagt ttttaactga agggataagg  56640
aggaccacgc tttccccaga ccagaaccgc gggccagggg gcgattccgc tgagtcaccg  56700
cgggcgcctg gtgcgcggcg gcggagcccg ggaccttcct tggctgcccc ctagcgaggg  56760
ccgcagcgca gcctgagaca cccgccgggg ccgctccacg gccgtcggat ttagactgga  56820
agctcggtcc aggtccccag cttgatgcgc ccgcggtgta ggagaccagc ccgactcgag  56880
cttcccctga gcccctggac tcttgactcc agcagggcct gggtaatgaa cgtcagctcc  56940
cctttcccaa aggggttgct ctgttgggaa ggcacccgtt tgatacagta gcatagagat  57000
gggttttagc atcaaaatat cagaattcaa gccttgctct ctgcttacta gctgtgtgac  57060
cctaaaaagg tttctgaacg tctctgagct tcagtttcct catcattcct tctcacgggg  57120
tggttgtgag cattacagag atcctctctg tgaagcccct gtgagtggct catcctgagg  57180
gctgaaataa acatgttatt aataatccaa aactggcaag ggatgttgac tggtccccct  57240
cccttgccca aggagctttc tagaacctga gttatcatta ccaaactgta ctgccttgag  57300
taagaaagtt agaaggaatg ggaaggatgg tggcaggtgg aggaaggcgg attggtcatc  57360
acctccttgc agcaagaaac agccccagat cgtgggaaac ctacagacct gctagacaga  57420
ctaggagcaa aagctggggc tttaagaatc cccagggagg ttctcctgag agagtagcca  57480
gttggatttt gtaagcagag atttgtttgg ggaggaggtg acaacgtagg gagcagaggg  57540
gcaaagctgt cgggaatcct gccttgaggg cagggatgtg tgttgggggg agttgggtca  57600
ctggggctcg gtggccttgg gcaagtttct acctctcagg tcctttaccc acctagggtc  57660
gccatcctgc ccacctcaca ggttacagtg agcctggatg cactgtcatg ggcaggtgcc  57720
caggaaaatg gcagacatgt tccaaacagc acgcagcatt ccccagtgat gcccagggtc  57780
accttggagg tgggcgagat gcctggggtt tctcgtccac cccacaacac ctcaggggac  57840
```

```
agccaaagct gtcccttcag gtaagctgca cagaagatgt gaactctgct gcaaagactc  57900
tattctttgg gagcaaaagg gacccagggt ctcacctgca catccctgtc cctgagggcc  57960
taggggttct tggaggcccc agccttggca aaatgaggaa gaaggtgaag gttgtctggg  58020
cccctgccag gctccttcct cggccacgca ctccccttcc tgcacacaca cccttctccc  58080
tccaccccat ctccattgtt gtcagaaaag tcacaataaa aaggtccata ttgtctagtt  58140
cccatacttt taatttttaa aattttattt atttatttat ttatgtattt tttgagacag  58200
agtcttaacc caggctggag ttcagtggca tgatctaggc tcactgcaac ctctccctcc  58260
tgggttcaag tgattctcat gcctcagcct cccgagtagc tgagattaca gatatgtgcc  58320
actatgccca gctaattttt gtatttttag tagagacggg gtttcaccat gttggccagg  58380
ctggtctcga actcctggcc tcaagtgatc tgcctgcctg agcctccgga agtgctggga  58440
tttcaggtgt gagccaccgc actcggctcc acacttttca cttattaaaa gactgtggtg  58500
tccatcaatg gatgaatgaa taaaccaatg tggactatcc ctcccattac ccaaggaatg  58560
aagcacggag ccgtgccaag atctggattc acagtgaaag aagccagtca ccaaaagcca  58620
cgtgctgtgt gacttccctt atacgaaata tccagaagag atacatccat ggtgacagaa  58680
agtagatgag cagctgggga ctggcgaagg ggagaagggg gagcagctgt ctatgaggtc  58740
cagcctttct tctgggtttg gtgagaatgt tttggaacta gatagaggtg atagttgtac  58800
aacattgtga atgtactaaa tgccactgaa tcattcattt taaatcgttc tttacgttgc  58860
atgaatttta agtcaatcaa aaacagttgt ttgaaaagag aaaagcctat gggtagcggc  58920
agcagtgatt ggatttatga ttcgattcca tggctcatcc ctcccctgcc tcacccccctc  58980
gccctccgac gtcttcttct tttactctga actgttatct ttgttctcat ctctctctct  59040
ctctctcaac cctgcagaca cttttccctt tctttgtctg cccccaccct ccagatttcc  59100
gtgtctccag tgtctcccta cgaggcatga attgagactg ggagggtgtg attctgaaga  59160
aggcaccaac agtgactcag ctagcccctt cccccacccc gccccccggg cctcaattta  59220
gctaaaaaac cacagggacg gactcaggag gcaatacctt tccaagggtc cctaaaaaat  59280
gtcccatttt agtgtccagg tttcactcaa ctttagtgcc tcccctaaaa tgtgttcctt  59340
acctcccacc ccactgcatc taagtcactg cctgagaaaa caggattgag gaaaggagaa  59400
aggaagagag agagagagga ggagagagag agagagggag gaaggctgat ggatttagaa  59460
aagaagaaaa caagtggtct gaggaaaaca gccttggtgt gtttattttc ctgtctgtgt  59520
atcgcttctc ggccttttgg ctaagatcaa gtgtattttc ctgtctgtgt gtctcgctta  59580
gattacaggg atctgtgggt gatgacacgt ctggtccagg ctgcgtagtc acctcaaggg  59640
catgcttatt gatgtgtttt tcaattcact atctttgcat gggagtccca ggccaagagg  59700
cacagctgcg ccatttgtct gttggtttag atatccttta tccagttctt ccagagaaat  59760
catcctgccc ttctggagga ggtgggcagc aggggtcaga gatgggaggg aaaggaagga  59820
gccaggtcct tggctaggat gccagggtcc cctgcctctc acctggcctg ggctggaggc  59880
ctcctgctgt cctgtcactg atcactaccc cgccccagcc tcctgagtta gaagacacag  59940
gctaaagtag agtatttctt cattgaaaaa cccatacaaa ataaaggttc ataaaaaata  60000
aaaatttaga ctgggtgctg tggctcacac ctgtgatccc agcactttgg gaggccaagg  60060
caggtggatc gcttgagccc tggggttcat gaccagcctg ggcaacatag tgaaacccca  60120
tctctacaaa aaatacaaaa aattagccag gcatggtggt gcatacctgt ggtcccagct  60180
tctcagccta tggacccaca tagaatacaa tgtcagcata agaagggagc cctggggtca  60240
```

```
ccaaatggtt tgggcggcaa agaacctgaa ggttgagaga agtggcttgg ttacccagct  60300
gttggatgtg agacctggcc actgcttctt ccatacccta gacctgcacc ctgacatctc  60360
aagtaaaaag ttgggggatg ttttatggtc caggatgaag gaagggcagt gaggggcagc  60420
ggagcatcac tttgcatttc tgtctgcctc ttactggctg tgtgacctgg ggcaggtaac  60480
ttcccagact cctgggaatc ataacaccta tgatgatgat gatgatgatg atgatgatga  60540
tgatgacacc tacctcaagg attgccctga agggtcacag agatgcctgc aaggcacctg  60600
catggagcaa gcgccccttc tctggcaggt gctgggtgag cactacctgc tgccaggccc  60660
tggggctatg gcactgcgtg accctgcaag tcctacctgg cgaagctgtc gttcttgtgc  60720
tcagtcagtg ttggttgtaa gactgagaag agtcacttca ttttgctctc cagggacatc  60780
tttctgggtc ctattttctg cctatgtcaa gtagcgcctc aaggatgctc ctgaaaatgg  60840
gcttgtcttt cttaacatgg caggtaggtc ccaaagcatt agcatggggc agctgaccta  60900
gcccagccaa tgcagtgcag tgactcttgc aaccgagtct aatcagaagg tccatgaacc  60960
tacgagcatt tcctgtccca ggatcagggt ggaggctgag cctccctgct tagagattct  61020
tcccatgcat tccacttttt tccccaaaag aaaatattga cccttgagag gcacacagtt  61080
tatttatttt gcatagtaaa tagtagcctg tattttaagg atgagttgat ttctgcatca  61140
gcccctgtag gtcatcagcc ttctattggt gcatctgact ctctctagcc ctgcagggat  61200
ggtggagggg gaggggaagg agggatcttt attggaaacc aggacagtga gactcattgc  61260
cctgtcatct gctctgtggt gctgaatgag gcagcccaac agagaaatac cctgagcgag  61320
catccccagc ctccaaaaca gtggcgcatt gccctgagtc ctgggaatga cctttgattc  61380
tcctgctcct gacttggaac ccatggaaac ctctagaagc agctgaggaa aacccaacat  61440
gaaaagcaga actccacact gagaatatag gaggtgatcg gaacatacaa tgattcttgc  61500
taagaccgat tcacagtttt tctttttttt cgatcgaaga aatactggag aagcctaaag  61560
aaggagtcta aaaactctgg cacgtgggcc aaaactgtcc ttgagctaag aatgattttc  61620
acatttttaa gtggttgaaa aatgaaataa aataagatga tgttttgtga cacatgaaag  61680
ctatgggaaa ttcaaattct aatatctata aatagtgttt tatcagaaca cagtcatgct  61740
catttattta tgctcgatgg ctgctttccc gctacaatta cgttgagcag ttacaacaga  61800
gaccacgtgg cccacaaagc cttacaatat ttactatctg gccctttcca gaaaaaaatg  61860
tgccgactct tgaccttaac ctcagcaatt tgggaggccg aggcaggcgg atcgcttgag  61920
ctctggagtt catgaccagc ctgggcaaca tagtaagact ccatctctac aaaaaataca  61980
aaacattagc caggcatggt ggtgcacacc tgtggtccta gccactcggg agactgaggt  62040
gggaggatcg cctgagccca ggaagtcgag gctgcagtga gctgtgatgg caccactgca  62100
cctcagcctg ggcgacagag caagaccttg tctccaaata aataaataat gcaaagtaaa  62160
ataaataaaa ccatataaaa aggaatcaat ttaaaattat aatgaaagct ggccgggcat  62220
ggtggctcac gcctgtaatc ccagcacttt gggaggctga ggtgggtgga tcacgaggcc  62280
aggagatcga gaccatcttg gctaacacgg tgaaaccccg tctctactaa aaatacaaaa  62340
aaaaaattag ccgggcacag tggcgggcgc ctgtagtccc agctactcgg gaggctgagg  62400
caggagaatg tcttgaaccc gggaggtgga gcttgcagtg agccgagatc gtgccacttg  62460
cagtccagcc tgggcgaaag agcgagactc cgtctcaaaa acaaaaacaa aaacaaaaac  62520
aaaaaaaaat tataatgaaa gccaaggggc atagtagaac aaattttcta gagctcatta  62580
```

```
agtcaaatga gtcaccagtt agtaaaacgc agtcacgggg aagagagggc aggattcttt  62640
gaagcagcgg ctctcctaaa aacaacccac ccttgtccag ctgccttccc tcctgagggt  62700
gttccctttg actgtgtgac ccccatcccc tatttcccaa ccgtccaagc ccacctctag  62760
cataatacga gcttttaatc cctctccctg accccaaccc gattttgaag cccagtctag  62820
tattttctca aatacacttc ttggctccat tccttccttt ccatcacctc tgccttttca  62880
ctgcatgctt ggaccactgc agtcagctcc ctatgaacag ttgctctcta cccatccaat  62940
cggccccgcc tgctgctgcc aaattcaccg agggcacctc tgtggtgctg cctgtggaca  63000
aagtccaagc cagccacctc acccacctac aggtgagtgg ggagcagcca gcgtgtccag  63060
tggtttaccc catcgccaca gacttggtga tgtgtcgatg tgcagagaag ggtgttggc   63120
agccacaaca caagcaaccc cgccccatgt gagatctaag atgggcgtgc tgggagccac  63180
ctctgagaat ccaacagaag gcagagggga gaacggctca cacggcacaa acactccttc  63240
cttttttttt tttcttttc ctttttgaaa ggagtctcac tctattgccc aggcaggagt  63300
gcagtggtgc aatctcagct cactgcaacc tccgcctcct aggttcaagc gattctccag  63360
cctcagcttc ccaagtagct gggattacag gtacactcca ccatgcccgg ctaatttttg  63420
tgtttttagt agagacgggg tttccctatg ttggccaggc tggtcttgag ctcctgacct  63480
caggtgatct gcctgccttg gcctcccaaa gtgctgggat tacaggtgtg agccatgggg  63540
cctagcctcc ttccatttaa atgtatgcct aatttgccca ttgagaacgg ctgagacgca  63600
ttttaagtgg ccagggtcta cttagagtta gtgctcatga ccaggcccag gtcaagcctg  63660
gctggccaga tggtgccttt gacctgctct gtctctgtgc aaaggaatga gctgaaggat  63720
gggggtgcag tgtgtgggca gtgggctggg gctggcagga ctcagtgact aagggaagag  63780
aactttcctc actaccagcc tgtcttttca gggcaccgcg gggggctttg ggacttggtg  63840
atgaacacag cacagagagc tgtccagcat gcgggtccct ggcttctcac acttcccagg  63900
ctccttcaga ggctctctcc aaagggagct gctctctcta gaacccatga atttggaata  63960
taggcaacca ctgcattggg gaccactgac ctcaaacata gagaccagag caaatggggc  64020
tcatcacgtg aaactcatct ggaactctag caggttcttt tatatatata tatatatata  64080
tatatttttt attattatac tttaagttct agggtacatg tgcacaacat gcaggtttgt  64140
tacatatgta tacatgtgcc atgttggtgt gctgcaccca ttaattcatc atttacatta  64200
ggtatatctc ctaatgctat ccctccccac tccccccacc ccacaacagg ccccagtgtg  64260
tgatgttccc cttcctgtgt ccaagtgttc tcattgttca attcccacct acgagtgaga  64320
acatgctgtg tttggttttt ttgtccttgc gatagtttgc tgagaatgat ggtttccagc  64380
ttcatccatg tccctacaaa ggacatgaac tcatcatttt ttatggctgc atagtattcc  64440
atggtgtata tgtgccacat tttcttaatc cagtctatca ttgttggaca tttgggttgg  64500
ttccaagtct ttgctattgt gaatagtgcc gcaataaaca tacgtgtgca tgtgtcttta  64560
taacagcatg atttatattc ctttggttat atacccagta atgagatggc tgggtcaaat  64620
ggtatttcta gttctagatc cctgaggaat cgccacactg tcttccacaa tggttgaact  64680
agtttacagt cctaccaaca gtgtaaaagt gttcctattt ctccacatcc tctccagcag  64740
ctgttgtttc ctgacttttt aatgatcgcc attctaactg gtgtgagatg ttatctcatg  64800
gtggttttga tttgcatttc tctgatggcc agtgatgatg agcatttttt cacatgtctg  64860
ttggcgaact ctagcagctt cttttcacaa gttcatggag agaggtttcc cactgaggga  64920
atcacatctg tctgatcaaa agaggcttgg gaaatggctc tcctgttcat tccctgaaaa  64980
```

cctctgatgg aaccactgcc actgtggcag ccccagcact ggcaccccag ccatgattgg 65040
tgccccagcc acatctctgc tgtgagcccc agagccctgg ttaattaatc atccacgtgt 65100
tgatggggag aggcccattc acaaaagcga cataaagccc agggagacgt ggccgtggca 65160
agaagggtgt gggactacat tccgccccca actgagagat tcagaaacca gaaaaaaatg 65220
gaaaaacata ctgtgctctt gggtgggaaa actaaatatc atgaagggag caatttttat 65280
agttttggcc tataatacaa ttccagccga aatcccagtg gaactttgag aatttgcagg 65340
aaaaaaaaaa atgtctaaag tacatctgga agacaaactt acaagaaggt caaataattt 65400
tgaaaaagaa aatgatatct aagcccacct agagaataag acttgagatc caaagctaaa 65460
tcaggaggct ctagcaaaat tgacagataa gcaggacaga gtgcatggtg cattcacctg 65520
gggaagaggg cagattggtc tacaaatagg cctgggtcca ctgactttag ctgttatatt 65580
tggggagaaa cttttcaacc tcactccatc ttaaacctaa aaatattcca gatgaattaa 65640
taaatataaa aaattagacc actaaaaatg tagaagaaaa tggatgatct ttctatacca 65700
tagagcaatg gaataaatca caaaggaaaa cagatttgac tatataaaac ttaaaccctg 65760
cccatcaaaa accatcagaa accaaaataa aaggcaacca actggagaag atagttgcca 65820
caaatatgat caagggttaa tgttattcat aaattaagag cccacacaag tcattagaat 65880
aagcactgag acctgaacag acaagcaaaa agaatgagag tgggtcggcg cggcggctca 65940
tgcctgtaat cccagcactt tggaaggctg aagcaggcgg atcacttgat cccaggagtt 66000
ccaacaccag cctgagcaac atggtgaaac cctgcctcta caaaagtcat aaatattagc 66060
cgggtgtgat ggcacacgcc tgtagtccca gctactcagg aggctgaggt gggtggatca 66120
cttgagcccg ggaggtagag tctgcagtga gccaagatca caccgctgca ctccagctgg 66180
agcaacagag tgagaccctg acttaaaaga aaaaaaaaaa aaaagaggag aaaaatgctg 66240
atctcactag taattaaaac atcaggccag gcgcagtggc tcacaccttt aatcccagca 66300
ctctgggagg ctgaggcagg cagatcactt gagatcagga gttctagacc agcttggcca 66360
acatggtgaa atcccgtctc tacaaaaaat acaaaaattc gccaagcgtg gtggcacatg 66420
cctgtgatcc cagctactcg ggaggctgag acaggagaat tgcttgaaca cgggaggcag 66480
aggttgcagt aagctgagat cgtaccattc cagtccagcc tgggctacag agcgagactc 66540
tgtcccagaa aaaattaaaa catcacatat ttaaacaact ctaggatatc atttaaaaaa 66600
acattaatag actgtttttt agagcacttt taggttcaca gtgaaactga gtggaaggta 66660
cagagacttc ccgtatgttc cctgccctcc acgtacagcc tcccccactg ccaacgtcct 66720
gcaccagagt ggtacacttg ttacaaccaa tgaatcctca ttaacatatc attatcaccc 66780
aagttcatag tttacattag taaaacatca tctttcatct ataagcacaa aaattttttg 66840
gcatttattt aggtgtatga ttaactcagt gttgacaaga ctcacacttc atacccactt 66900
gcactgcatc tgagaagcaa ttggtgtcta cagccgctac accctcaaca agcccgatct 66960
tgtttgaaaa gcaattggtg atgcttctca aaattctatg gacaaagtca gccgggcatg 67020
gtggctcatg cctgtaatcc ctaaactttg ggaggccgag gcaggcagat cacctgaggt 67080
ctggtgaaac cctgtctcta ctaaaaatgc aaaaattacc caggcatggt ggctggggcc 67140
tgtaatccca gctactcggg aggctgaggc aggagaatcg cttgaagcaa ggaggcggag 67200
gtttcagtga gccaagattg caccactgca ctccagcctg ggtgacaaga gtgaaactcc 67260
atctaaaaaa aaaaaattat ggacaaagtt tttcaaaaag atatttaatg caactttatt 67320

```
tgtaatattg gaacatctga ggccatttca gtgctaacta ttaggggatg gttaggaaaa  67380
tatggtacat atgtggaaag gaacatttgg tagttagtgc ccctgatgtt tacaaaggct  67440
tttagtgacc aacaaatgct catgctataa tcttatgtga aaaaagcaag tagcataatt  67500
gcaactatat ttttaatgca tagaataaaa ggctagaagg aaatatcaca gatccttgac  67560
atacattccc aaacctttgt aaatccgcgg attcatgaaa acagacacat ttgcacaagt  67620
gcctgatctt ttctgttata cattcattag aagtcaagcc ctggtgccac aaagtatctg  67680
ccttttcaaa tgtgatcaga atgttctctt ttgcttcaag gccatttttc acgaagcagt  67740
ggcatttttg cctcttcatc agagtcaccg tgtgccctgg aggactgaga acagcagagc  67800
cgttttagga tgggacaggg cagccaggag gattgggctc actccctact gagtgcctca  67860
ctcccgtaca gcccccatag aggaagaggg gttcaaattt attcctcagc cagatggcat  67920
gtgccgcctg tcctggaatt tcacatcact tatgatggac caaaattcca aaagctgaat  67980
ccatgattgt caaagtctgg tatggcagga tgtcaacagt aatcgtttct gggcagaggg  68040
atgatttctc cttcccatct tgctttgtat aaatacattt tctataataa ggttgtatta  68100
cttttctcat caagaaatag caaagtactg ttttactcaa aatatgaata gagccaggca  68160
tggtggcagc ttatgcctgt aatcccaaca ctttgagagg cggatatggg aggatcactt  68220
tagcccagga gtttgagacc agcctgggca acatagtgag acccccgtcc ccactccccc  68280
aaagaaaacc cacaaagcat ttatcctgga ttattcacag gggccaaaaa aaaaaaaaaa  68340
ttcaggcctc ctatagccat gagctacgaa tatgaaaata tgcaaatgtg taagaaaagc  68400
cagcacatcc gatttttact tttactttca cacctctgtc caccatgttc caagagaaga  68460
aacttggtca ttgaaaggaa tagatcaaat ccaaagaaca aaaccactgt gctcattaaa  68520
cttcttagtg ttcacaaagc tttagctgca ggttgaatgg ggcaacccga attggctggc  68580
tcacctgggc tgcagggagc agagatcgcg acactgcact ccagcctggg caacaaagcg  68640
agactctatc tcaaaaaaaa aaaagttcat aaattcaaag ttatgaatta tttttaaaat  68700
aataataatt tacaataaag atgaggacaa agtgtgagta aatggtggtt tctatccagc  68760
tctgttgagc tgaagtggca tctccctgct ggggcttttg gggaagaagg gtgtgtgttg  68820
ctcttcagat cccaagcctc atgcccctac tgggccctgt ggggtgcttc tcagcccacc  68880
aggagagcca ccgttggaac acacacgtgg gggacctggt gggtgccggt gtggtgaatg  68940
ggggccacag cctgactcca ggaagccagc aaactcggag ctggaggagt caggacaccc  69000
ccgatgagtc aagagttggt tttgctgcca gttgacatct gattgaacca tctcttcact  69060
tctccgtgcc tcactttcct taccagacag gctctgctga tgctgtccct ctcctgttca  69120
gtcgtgccct caccgttaaa gagaaagagc aaactgctgg gcagcagcat tgattttttt  69180
aatgaagtgg aaagagagct gggaataaca agtcgggccc acctcacctg cctcacctgg  69240
tgggtttatt tgttttgttt tttttttttt gttttgagac agagtttcac cctgtcaccc  69300
aggctggagt gcagtggtgt aatctcagct cactgcaacc tccacctgcc aggttcaatt  69360
gattctcctg cctcagcctc cccagtagct gggattacag gcacctgcca catgcctggc  69420
taattattgt atttttagta gagatggggt tttaccatgt tggccaggct ggtctcgatc  69480
tcctgacctc aggtgatcca cccacctcgg cctcccaaag tgctgagatc acaggcgtga  69540
gccaccatgc ctggccgtca cctggtggtg ttgaatatga actgctgcgg tgttggtaaa  69600
ttaagcaagc agatagatgt aaataacgct tgggcaggaa tatggagcac gggatgagga  69660
tgggcggcca actgttagag agggtagcag ggaggctgag atctgcctgc catgaactgg  69720
```

```
gaggagaggc tcctctctct cttcaccccc actctgcccc ccaacactcc tcagaactta  69780
tcctctcctc ttctttcccc aggtgaactt tgaaccagga tggctgagcc ccgccaggag  69840
ttcgaagtga tggaagatca cgctgggacg tacgggttgg gggacaggaa agatcagggg  69900
ggctacacca tgcaccaaga ccaagagggt gacacggacg ctggcctgaa aggttagtgg  69960
acagccatgc acagcaggcc cagatcactg caagccaagg ggtggcggga acagtttgca  70020
tccagaattg caaagaaatt ttaaatacat tattgtctta gactgtcagt aaagtaaagc  70080
ctcattaatt tgagtgggcc aagataactc aagcagtgag ataatggcca gacacggtgg  70140
ctcacgcctg taatcccagc actttggaag gcccaggcag gaggatccct tgaggccagg  70200
aatttgagac cggcctgggc aacatagcaa gaccccgtct ctaaaataat ttaaaaatta  70260
gccaggtgtt gtggtgcatg tctatagtcc tagctactca ggatgctgag gcagaaggat  70320
cacttgagcc caggagttca aggttgcagt aagctgtgat tataaaactg cactccagcc  70380
tgagcaacag agcaagaccc tgtcaaaaaa aaaagaaaag aaaaaagaaa gaaagaaatt  70440
taccttgagt tacccacatg agtgaatgta gggacagaga ttttagggcc ttaacaatct  70500
ctcaaataca gggtactttt tgaggcatta gccacacctg ttagcttata aatcagtggt  70560
attgattagc atgtaaaata tgtgacttta aacattgctt tttatctctt acttagatca  70620
ggcctgagtg gcctctcttt agcaagagtt ggttagccct gggattctta ctgtagccac  70680
attaataaac aacatcgact tctaaacatt ctataatacc atcttttggc caaattgact  70740
tcgcctcttc ctctctcttt ccaaatgaaa tgtgtttcat ttcactgtca gaccacatgg  70800
ttggggaccc cacagagcac acagccctcc ctctgccttc ccatgctggc ccttcaccca  70860
ctgctggagt gccaggttgg tccaagggtt ggaccaagtt gtctgaggtt gtctcaaggt  70920
tggtcgaggc tgtctccgcg ctgggttgtg ctacaaggag cccttctttc catgggtgtg  70980
gctggcagtg agtgctcaca gcaacagccc acagtgcagc ccgagggcag gatggactca  71040
gtccctgcct ccatacccat ttctaaggag gcaaaatggc aaacactcta cttttctctt  71100
ttaatgctaa aaataagaaa acaccttgca gcccagggta tgggtagtgc atggaagccg  71160
tggagttgtg aggtgggaag tgacctctgc tggatatgtc tattcaggaa gattgctgga  71220
gtgggtgggg tctctgggag gtcccctgag tgtgggaagc tgggaccacc agctttctcg  71280
cacagggagt ggccatccca gcttggagag gttccaggac tggttgggag gcacgtttca  71340
gatttctatc tgttgaatca gcgaagatat tggattatga ggaatttggg aattaggaaa  71400
gtgggtgcag gtgggttggg ggtaggtgaa ggaagacatg ggcgtattgg gggagcaggg  71460
gctgctcaga ggtgttccag aagctctggg tgaggaggtg agagggaccg gggaatgcag  71520
ctcggcccag cctccctgcc tgaggtcagc catcacgtgg tgatggcaag atggaaatgt  71580
gctttctgac tgctccagcc agtgctgcca gattcagctc cccagggagg gcacctgaga  71640
ggctccaagc caggagatct gttttctcct ttgttttgtt ttttttgtt ttgttttgtt  71700
ttattatact ttaagttcta gggtacatgt gcacaacgtg caggtttgtt acatatgtat  71760
acatgtgcca tgttggtgtg ctgcacccat caacttgtca tttacattag gtatatctcc  71820
taatgctatc cctcccccct ccccccaccc cctgttttct cctttgaatc cttcttagag  71880
gccgggtgcg gtggctcacg cctgtaatcc cagcactttg ggaggctgcg gcaggaggat  71940
tgcttgagcc caggagttcc agaccagcct gggcaacata gtgagacctc gtctctacag  72000
ataataattt taaaaattat ccgggcatag tggcatgcac ctatagtccc agctactcaa  72060
```

```
gaggcagagg caggaggatc acttgagccc aggaggcgga ggttgccgtg agccaagatc  72120
ccaccactgc actccagcct gggcgacaga gacccccatg tcaaataata ataataataa  72180
ataaatcctt ctcagtccct tcctcactgt gtccccctcc actgaatttt tccacctcct  72240
ctcccacttc ccccactccc gctttccctc tccttctctc cccactccat ctttttcttt  72300
ctctgctgtt tctcgtccct ccctcctctc catcccacaa cactgcctac cctgtccctg  72360
ccccaccctg gtgctcagga tgtgtgaagt gaggggtggt agcccccaag acctcaaccc  72420
cgaaggttag cctgttgaaa ccactttctc ccagctgccc ccctggcagt tggtgctgct  72480
gggggaaact gggattgggg gccagatttt gcctcttttc ctgacaaaga gagatgaaga  72540
gttctctcac caggtgcctg ggactggggt gtgggtgtcc cagcctatcc cagcgcatct  72600
gttctgcatc atgattaata gtgctgcttt cagccgggcg cggtggctca cacctgtaat  72660
cccagcactt tgggaggcta aggtgggcag atcacaaggt caggagttcg agaccagcct  72720
ggccaacatg gtgaaacctc gtctctacta aaaatacaaa aattaaccag gtgtggtggt  72780
gggtgcctgt agtcccagct acttgggagg ctgaggcagg agaatcactt gaatctggga  72840
agcagaggtt gcagtgagcc aagatcgtgc cactgcactc cagcctgggt gacagagcga  72900
gactccgtcc taaaaaaaaa ggagttttgc tctgtcgccc aggctggagt gtagtggcgc  72960
catctcggct caccgcaacc tgcgcctccc gggtgcaagc gattctcctg cctcagcctc  73020
ccaagtagct aggattacag gcgcctacca ccacgcccgg ccagttcttg tatttttaga  73080
agagacgggg tttcaccctg ttggccaggc tcgtctggga ctcctgacct caggtaatcc  73140
gcccacctca gcctcccaaa gtgctgggat tgcaggcatg agccaccgtg cccagtcaac  73200
tccttctcaa aaaaaaaaaa atagtgctgc tttctctttc aagtgtcctg atttgggtga  73260
tagtaaatgc cactctactt ataagggatc tacctcagaa tgctaattgg gacatttttg  73320
tagcactcta ctgttggcag caggtgatgc tcacaacagc ccgtgagggt ggatgacgtc  73380
cgcttcacag atgacaaagg agcctcatgc tcagaccgtg ggctgccaga gcaggtccat  73440
ggctgcagcc ccacatggac catatttccc ccttgtcact ctttccacca agctcccttg  73500
gaacttcagt tattaagctc tcttgggtgg aatccaagtt agaatcacaa catgtgcctc  73560
atatggattg tgccagtgaa aaatgacatt ctatttagag gcagggcagc ctggcttaga  73620
gtcagtttaa aatatgtatt atgctgcaac aaatgtacca tgatcctgta agatgttcac  73680
aacaagggaa ctggatgtgg ggtatactgt ctgtactaac ttcacaagtt ttctgtaaat  73740
ctaaaactgt tccaaaataa caagttcgtt taaaattaac tccaggagac caggtacggt  73800
agctaatgcc tataatccca gcacttcgga aggctgaggc aggtggattg cttgagccca  73860
ggagtttgag acaagcctgg gcaacatggt gaaatcctgt ctctaaaaaa aatcacaaaa  73920
attagccagg tgtggtggcg cattcctgta gtcccagcta cttgcggggc tgaggtggga  73980
gaatcatctg agcccaggag tttgaggctg cagtgagctg tgattgtacc actgcactcc  74040
aacctgggca acagagcaag accctgtctc aaaaaacaaa aatgaaataa agtccaggaa  74100
agaagtaggt tttaccactc ttattttctg aagagaaaac taaatttaat gtgtaaagtg  74160
aggacaagtt caccaagtta gtgtttgagt tgcctaaaat atgtttgcta aaactattca  74220
aagctttcac ataaaacatg atcagaagtt ctatgccaaa acatatgtgt gtgtatatat  74280
atatgcacta tatatactgt atataaaaat gcaaaatcta aattgccaac cttttagaaa  74340
ttgctctgaa aggaaagcat ttcaagataa tttgcttacc caaagaatat actttccaag  74400
aaagcaagta atacttaagg tgttcataat cctcatcaaa ttaattcttg ctactgaaag  74460
```

```
cttacaagga gctgttttga tgtcgggtgt gacaggtttg acttggcaga aggtgtcact  74520
ttactaacaa cattttaaat aagtgacaga agacaagaaa ctacacgtta aatgccagaa  74580
caaagagtgt ctaagtggat gctaagagtt gaaatatggc tggatacctg cccaagagag  74640
ctgaaaagta gatgaaagtt ggttacctat aaactagtgc accctaatga attaaaaggt  74700
gttgatgagt taacttgtta tgccttccag ataagacatg caaatggggc ttcttcctcc  74760
ttcactactt ccaagggatt taacaaggag accaatgcaa atgataagga ctgtagggct  74820
caagctgggg acagattggg gaaaggggga ccatcatgcc catatagatg tccctgtgcc  74880
ctggcagtca aggctgctga aaaataacaa aacccagaag tctgcgtgat gctgcctctc  74940
catttgtcca aagccttctt gcggcagttt gcaggctttt gcaaaagctc caggaccaag  75000
gagctatgtt catgctggaa gcttgttcag gattagctgt tctttgtggg atgggtgcag  75060
ccagggccag gtgtccaggg acagtgtttt aacaaagggc atgaggtgtc tgatctcaca  75120
gtggaactcc acttgccttt ttttcatctt ctcattctgc ttcatgcaca gaaccagccc  75180
catcctgaaa ctgactctaa attactcccg ccccaggtgg agtgcctttc tcggagttca  75240
acagagcctt cctgtcgccc aagggacaac tccactgaat gcccaagcca cacccaaaac  75300
ctaacaagta aaaaccaaat tctgtgctcc cccatcctgg gccattcctg gtttctctac  75360
tgctgttggt gataccacca tcagcttgtc catcatgacc ctggccagtt cctcccacaa  75420
ccctccacag cacccaggga cctcacctcc attccatccg acacagatct cctcaccaca  75480
aaccttggtt ttgcaacagc agccatgaga cctttacacc ctccgccctt catcctgtcc  75540
cccactgagg ccccagagcc attccttaaa gcagcgcgcc acaaactata acccacaagc  75600
caattctggt acccagcctg ttttgcacag ccagtgaact gacaatgatc ttttcataca  75660
gccagaaaaa caaaacaaaa caaaaaaacaa caaaaaaaaa ccccaccatt ctgagcatgt  75720
gacttccatg ttcaagatgt ctcatgttca gaaaggcccc tggaaaagga ggaaggggag  75780
ctgggcacaa agggagaccc tctcagctga gctcctccca tccagacatt ttcctggact  75840
tcctatccaa tgacttccct tagcttctta tcagccaccc ctgtctgccc aggaggctgg  75900
aagatgtggc cttttaactg ggcacagctc tgtcctctat catatcaggg ctctgttccc  75960
aaggagggta gagagaatgg acaccaggtg gaccctcagc agtctgtgcc acagagggag  76020
tgtttgcaat ttccagacta aaagtcccca tgtgcttgac ggggtatgtg actacaacgt  76080
gatgcttgac ttttcctcat atgaccagag ccactttgtc catctggtac aatgtcagct  76140
atctgctagg ggccctccag gattcccagt caattccata tctgcatcac caccattggc  76200
actaaataaa ataaaatact caagttcctg ctggtgagca tgagcagtgc tacactgggc  76260
ccttcaacca aggtgacatg ataatgactg aaaataatca ctgccactta ttggggacgt  76320
ctcatctgcc aggcatggta caaagtgctt taaataagca ttcaacaatt tcatgctgac  76380
agaagccctg tgagccagtg gagctactac tatgcccatt atacagggga gaaaactgag  76440
gcagagagag gttaggtaat tcgctcagcc tcacacaacc aataggtggt ggagccagga  76500
tttgggcccc atctgcctga ctctctagag gctctatctt ccagtcttcc agagttgagt  76560
ctaagccatg aataggacaa ttagacagca gaggaaaccc attcagccac catgtgcatg  76620
aagagtaagg aatttctgtc atacagaggg gagtgaattc actgagctga gagctgagga  76680
accattgatc tgatggctga gacaccactg ggaagactgg agaggctttt ctgggcatgc  76740
agtgccaggc acaggaggag ctgagggaag atgactaaga ggtactggca aagaattcag  76800
```

```
aaattctgat ggaagcttta catgttacca tcacatccat ccatctatcc acccatccat  76860
ccacccatat cttcctccct ccacccaatc atgcatacat ccagtcatct atacaccacc  76920
cacccaccca tccatccatc catccatccc ttcatccatc ccatcatcca tccaattata  76980
catacatcca atcatatatc tgtacataat ccattcttcc ctcggttcat ccatccatcc  77040
attcatccat ccatccaccc atcccttcct tcatccttcc tatcatccat ccaatcatat  77100
atctgtacat aatccattct tccctcggtt catccatcca tccattcatc catccatcca  77160
cccatccctt ccttcatcct tcctatcatc catccaatca tacatatatc caatcataca  77220
tctgcacatc accagctcat ccatctatcc atttatccat ccatccttcc ttccatccat  77280
cattcatcca tcatacatac atctaaccat acatctctac atcattcatt cttccatcga  77340
ttcatccaat tatccatcat tccttcctcc atccatccca ttatccattt gatcatacat  77400
atatcatcta tacatcatcc attcatccat ccatccatcc atccacccat atcttcatcc  77460
aatcaatcat acatacatcg aatcatctac acatcaccca tccatccatc catccattca  77520
tctatccacc catccatcca tccatccatc cattcatcta tccacccatc catccatcca  77580
tccatccatc catccatgta accatccagt catatatcca attacacatc catccagtta  77640
tacattcata catgcatcta atcattcaat tatacataca cacatccata taattctaca  77700
tccaattata cctccatcca attacacatt catacaccca cctaataaat tattaattca  77760
tatatccatc catataatta tacatcaatt atacatccat ctaatcattc agtaattcac  77820
ccaccatcca gtcatctatc caataataca ttcatccaat catccatcca tccatccacc  77880
cattcatcca tccatccgtc cgtccaccca tcatggtatg agccatgatt taccacgatg  77940
gtcccctgtg gacagcccag gtggggcaga actgaaggga agcccagggc tgcccccata  78000
aacatttgcc tcctttacat ggatgagaac tagatccaca tgtataaatc ctcatgattt  78060
gaaggtgctt ttaccaacat tcactcatgg gattctccca ggagctctag gaggaggcag  78120
gtagagttga ggtcatctca cgcattttac agatgaggaa acggaggccc tgagaggcag  78180
gtccaaggcc acctgaccag aaagaagtgg aactgggact tgaacccagc catcttgccc  78240
cttggtccca tgctctctag cctgtaactc ctgcttcctg gtggggcatc tccaggagga  78300
ccctatcggc tggccatggg cctgccctgg agtcttttgc tctgtgtggc catccttcct  78360
ccctcaggag agtgtgtgct cccagagcac aggctgtatc ttctgagcat tttgtccctt  78420
cccagtacct agcactcagc tctgtataca ttgggctctc aagaattctc aaccttccag  78480
agtgtaaggc cttgacctgc tcagccctgg atactgcatg atgcattgat aagcccataa  78540
aataaccagg gcagattgac tcccagtggc caaagtgcca cagggaaggg acaattcagc  78600
ccttctagga ggaggaggag gtagttttct catttctatt aaggcaacaa aagctgcctt  78660
actaaggaca ttcttggtgg agggcgtgac tgtcaaccac tgtgatcatt tgggcctctc  78720
ttgcccaggc ttcccattct gaaaggacag ttttattgta ggtacacatg gctgccattt  78780
caaatgtaac tcacagcttg tccatcagtc cttggaggtc tttctatgaa aggagcttgg  78840
tggcgtccaa acaccaccca atgtccactt agaagtaagc accgtgtctg ccctgagctg  78900
actccttttc caaggaaggg gttggatcgc tgagtgtttt tccaggtgtc tacttgttgt  78960
taattaatag caatgacaaa gcagaaggtt catgcgtagc tcggctttct ggtatttgct  79020
gcccgttgac caatggaaga taaacctttg cctcaggtgg caccactagc tggttaagag  79080
gcactttgtc ctttcaccca ggagcaaacg cacatcacct gtgtcctcat ctgatggccc  79140
tggtgtgggg cacagtcgtg ttggcaggga gggaggtggg gttggtcccc tttgtgggtt  79200
```

```
tgttgcgagg ccgtgttcca gctgtttcca cagggagcga ttttcagctc cacaggacac  79260
tgctccccag ttcctcctga gaacaaaagg gggcgctggg gagaggccac cgttctgagg  79320
gctcactgta tgtgttccag aatctcccct gcagaccccc actgaggacg gatctgagga  79380
accgggctct gaaacctctg atgctaagag cactccaaca gcggaaggtg ggcccccctt  79440
cagacgcccc ctccatgcct ccagcctgtg cttagccgtg ctttgagcct ccctcctggc  79500
tgcatctgct gctccccctg gctgagagat gtgctcactc cttcggtgct ttgcaggaca  79560
gcgtggtggg agctgagcct tgcgtcgatg ccttgcttgc tggtgctgag tgtgggcacc  79620
ttcatcccgt gtgtgctctg gaggcagcca cccttggaca gtcccgcgca cagctccaca  79680
aagccccgct ccatacgatt gtcctcccac accccccttca aaagccccct cctctctctt  79740
tcttcagggg ccagtaggtc ccagagcagc catttggctg agggaagggg caggtcagtg  79800
gacatctgat cttggtttag tatccttcat tttgggggct ctgggtgtgg cctgggcctc  79860
tggactttgg ccacggtgtt tgttccagcc cttctcctaa cctgtccttt ccagacactc  79920
ggcatctagg ttattagcac ctcgcatact ttctgacatg ctcctcagtc ctgattttga  79980
ccatcttctc ttgcttccca tctgtgtcag tcaagactgc atttggctgt aagaaacaga  80040
aaccccaact aactgtggca tttacatgaa gaggtttact tttctcacat aatcagatgt  80100
ctagacttgg ccagcacctc aagggtcatt gatgctctcc tgtctttatt ttctgtcatc  80160
tttagtggtt ggattgttgc ctcatggtta caaagtggct gctgcacttc caggcatcac  80220
atctgccttt gaagcaggaa caagttgcaa agtaaagtgg ccaaaagggc cctgaaacta  80280
aatgtgtccc cttaggaaag caggagtttt cttgcaagtg gcaatcttct gcttatgtct  80340
cattggccag agctgggtct tacggccacc ccttgctgcg agcaaggctg ggacattgag  80400
cattttgccg tccaacctct ttagcagaat aaaccaaggg ggaagaacgt taatagtggc  80460
ttttgagtca ctagttggca gtatctgccc ctctatcttt ccatcctccc catggagttt  80520
caaggttcct ttctcagtac ttcttcaggc tctgcacgtt catttggatc ttgtgtcttg  80580
gggtgaaaaa ctggcccaag tgtctcccca agcatccacc tttggattaa tttggaaaat  80640
ggctgtcaag tgcccgcctc ttgcttggta taatgctaca gctttagagg acgcagcagg  80700
catgggcctt gccgctgagg ttcttagcct catgagaata tccagatcag attctcttgg  80760
ctccttctta gagccagtga tgcaagacac ttcctgctca tcttgtcggg acggttttac  80820
aagttgcctg ccatcctgag aaagtctaca aaacgatgcc agacctcatg ccagcttccc  80880
aagccttgac tctcagtgct ccctcaacag gattctggaa gaatctccca aacaagtcgc  80940
aatcccctct ggaccctgtg caggcatgag actcaagagc attggctccc acccctggtg  81000
gagggaacac tgctggggct gggatcttgc ctggttgctc cgcctgcacc caagacaacc  81060
ataattaaaa tgtccttcat tgaacttgga aagccttcaa agctgacaac tccttatgtg  81120
tacccggaaa ggcctgggag tgtgccaggg cattgctcgg gagggacgct gatttggaag  81180
catttacctg atgagagact gacagcagct cctggtagcc gagctttccc tcctgcctct  81240
gctgtgaagg tggacccatc caacagtcaa atgcctgact ctggacagga gcggacctat  81300
ttattgccat gcaagggact ctgcactttt gaattgtggg tcatgggctt ggatttaggg  81360
gttagagctg ggagaagtct tggaagtcac ctagagatga cactgccatt ttgcagatga  81420
ggaaaccgtc caatcaaaat ggaccaagga cttgcccaaa gcctcacagc aaaaccatag  81480
gcccccgcac taaccccaga gtccctgtgc tgtcttaaga atcaaatagt tgtaagcaat  81540
```

```
catctggttt tcagtatttc ttcttttaaa atgcctgggg ccatgcccag cagtctgttt  81600
cactgcagcg tttacacagg gctgccgggc tttcctggtg gatgagctgg gcggttcatg  81660
agccagaacc actcagcagc atgtcagtgt gcttcctggg gagctggtag caggggctcc  81720
gggccctact tcagggctgc tttctggcat atggctgatc ccctcctcac tcctcctccc  81780
tgcattgctc ctgcgcaaga agcaaaggtg aggggctggg tatggctcgt cctggcccct  81840
ctaaggtgga tctcggtggt ttctagatgt gacagcaccc ttagtggatg agggagctcc  81900
cggcaagcag gctgccgcgc agccccacac ggagatccca gaaggaacca caggtgaggg  81960
taagccccag agacccccag gcagtcaagg ccctgctggg tgccccagct gacctgtgac  82020
agaagtgagg gagctttgcg tgtttatcct cctgtggggc aggaacatgg gtggattctg  82080
gctcctggga atcttgggtt gtgagtagct cgatgccttg gtgctcagtt acctccctgg  82140
ctgcctgcca gcctctcaga gcatttaggg ccttctggac ttctagatgc tcctcatctt  82200
gcctcagtca gcgcgtcagt tccagagact tctctgcagg gttttctggg gcaggtggtg  82260
gcagacccgt gccttcttga cacctgaggt cagtccaccc tcctgctcag actgcccagc  82320
acagggtcac ctcccaaggg gtggacccca agatcacctg agcgcacaga gggtgcagat  82380
gactggacca caccttttgg tgatcttaat gaggtggtcc cagaggagct cagacatgca  82440
atctagcatc cagttctggg actctgtctc cttttcaaac gtattcatgt agaacaggca  82500
tgacgagaat gccttgtcaa catgggtgat ggggaatcaa tcagacaggg cgccgggctc  82560
aaggctgcag tcacccaaga gtggctcagc ccaccaggcc ctaggaaacg cctgcacagc  82620
ctggagctcc tggagtcatt tccttcatgt cttcttcact gcacttacgt aaagatgcca  82680
gccattggtt tggtgatttg gagggtgccc agttgcccaa caagaaatgc agaagaggcc  82740
tagccaggat ttcaccagca gtggagagta gagaagatgt ggccagaaaa gagtttcctt  82800
tccctcctaa agatggtact ccctgcagct actggggaag cctgcagcat tctctagggc  82860
tctgtgtgtt gagagcagcc ccaccctggc cccttctgag tgcatttctg ctttgtgact  82920
tgatccgtga agtcccctga gatgggcaga ggggatgtcc tcgaagctgg ggcagagcct  82980
catccttgaa cgtgaaggac gtttgaagac tgtggcatga tcacaggatg agatcacagg  83040
gaacttgagt ttctctcctc ctctcccttc acagttattt cactgaggga aatccctccc  83100
ctgcccagaa tgaaaactct agccaactct tgacttttcc atcactccaa agtagttgaa  83160
agtacattag tctccacagt ggcaaaacag tgtgcaaaag ctaaataatt agaacagcca  83220
gtcccatgtg acagtcaaag cttctaactc cattcaaagt tgcagccatt cccctcgagg  83280
gctggcaggg aggggagggg taagagaaac aggaaggttc ttactgagtt ggtcctggtg  83340
tgagctgcgt cacactccct gcagaggttt caaggagact ctctctctct ctgtctccat  83400
ggggacctta tttgaattct tctactctta ccccagcctg ccatctccag ctatcctccc  83460
ctgaagagcc cttctgctgc gctggattct ggtggccatg tcatctcctc ggccccgtgg  83520
gagtctgaag atctggctgc agcctcacct ctgaggtcct gctagttgcc acctcttaaa  83580
catgatctga ggctcccatg cactctgacc tgtgcccaca tggggcccac gggaaacacg  83640
ctggcaagca aactgtgggt gtgcagacgg ttctcagggc tgcagcacct gtcctttgct  83700
ctgcccccaa agcaaggcca gcccatcttc catcctctag tgttccttgg tggggccctg  83760
accacagtcc accaggtccc taaccagagg ggacacacac caggtgtcct caatgtattg  83820
ccttgaaaca gttgtgctgg gactgtgatg gggggtggcc atgtagccac ccccaccacc  83880
cccaagccac tctctccaag gaaatcctcc taaagatccc tttacatcct ccatgtggtg  83940
```

```
gggaggttct agagttgggt gcatgtgtct tcagctactg acaatgcaga ccttagttgg  84000
cacctcgctc tggcctatcc tgtttgctgt tcttggcgct ccagtgaaac tccccatggg  84060
ccatccagtt ggggtgcagt gtggccaccc ccttgcaggt tcctgccttg ctggagagca  84120
cagggccctc ctggctcttg taaaacactc cccatggtac agagaggcca gcagtgatgt  84180
gaggcccaac ctccctccat ggtgttccca agcagctccc tttctggggt caaggggtgg  84240
caaagacagt gcagcgtcca atttctgact caagccgggc ctggctatcg cagctctgca  84300
ctgtgtgtga cagcaaggca actcacccag tgccgtggca gtgaccgtgt ccgaggaagc  84360
ctcctcacac cctctgtctc aaggactctg gcatttagct ggacttgctg tagctctgag  84420
cctttctgcc attgccatca ccttgtcaga aactcaggcc gaatctgcac tcagagttgt  84480
gcccaggcag ttgagccaac acttgctcag cgatattgtc acatgacaag gcactgtcac  84540
cactgggcgt cgtgggtagc gcagtgtcgg ctggatggac ccggagggtg tctgtgtcat  84600
gctagtgcta gtgatgggag ccccgtgagc ccattgcccg ccctcccatg ccctcagcag  84660
ctgcctgggg acagccaatg gcctgggtgt ttctgaggct accacatggc ttccaggaaa  84720
ctcgagaacc tttctctccc ttgcctacac tcttcacaca ggcctgtgct ggccagcggt  84780
ggggatccgg cattcctatc ttaggtgcag aaagtgactg actcattgca ggcctgggag  84840
ataagactga tggcccagcc agcaagatgt atggatttct cagaggcagt ggcctctgtc  84900
attgtcctca ggaaatgctg gtgattctgg tggcctgagg tcaatgcatg tcaacgtggc  84960
caacttgcct tataaacttt ttttctggac aattgcgtgc actgtcctgt aacagtgtcc  85020
tgttgtttat gatgcagaaa taggtgtttt taaagcctat tgattttggt actattaatg  85080
tggtcaggaa ctttctcagt ctttcttgtt tggggtgagc tgtggcttcc taaacaggaa  85140
cccaagacac ccccaaaagc tgctcaccag cactgccagc ctccctctta ccaagtagca  85200
cccgttcagg acattctgcg aaaggcattt gcccagaagt tgggaggaag gaaatgtaac  85260
attttggggc acctaccata tgccaggcac caggctaaac gtgttcacac aaattctctt  85320
actaaccctc accatccttc tacaagacaa actagtatct tcatcttggg gttcaagatg  85380
aggaaatgga ggctcagaga ggttgaatga atgccggtgc ctggatatga accccatctg  85440
cctgactccg caacccaggc aaagtctttc cttgaacttc ccagcagcca ctgcttagac  85500
acagcctcca caaccatggc tcagcagcaa attgcttctc tgacctcact cagcctgtgt  85560
gtccttgttg agtgaggcat tcaggaccct ggtcccaaag tggagaaagt ctttcctact  85620
aggtcatagc tacacctgca tgtgggtgct gtgcctttg tttagtgaac ttttatcacc  85680
agcatcctca gcaatgacat ttgcagagaa gccagagctg aggcaccttg gtattcttgg  85740
gatgtgactt tcctgaatgt ttaagggaaa atgcccgaag gtacagagag cttggtttct  85800
agtaaacaat aactgtcttg cttttacccc ccttcatttg ctgacacata caccagctga  85860
agaagcaggc attggagaca cccccagcct ggaagacgaa gctgctggtc acgtgaccca  85920
aggtcagtga actggaattg cctgccatga cttggggggtt ggggggaggg acatggggtg  85980
ggctctgccc tgaaaagatc atttggacct gagctctaat tcacaagtcc aggagatttt  86040
agggagttgg ttcttatcaa aggttggcta ctcagatata gaaagagccc tagtggtttt  86100
tttctaatac catttctggg taattcctaa ggcatttagt gttctgaaag atgctagcct  86160
tgtccagcct gggagttgag aatgaatgtc taacagaaac tctaggccgg gcgtggtggc  86220
tcacgcctct aatcccagca ctatgggaga cccaggtggg cagatcacct gaggtcagga  86280
```

```
gtttgagacc agcctggcca acatgtgaaa tcctgtctca ctacaaataa aaaaattagc  86340
cgggtgtggt ggtaggtgcc tataatccca gctactcagg aggctgaggc aggacaatcg  86400
ctcgaaccca ggaggtggac gttgcagtga gccgagatcg catcattgca ctccagcctg  86460
ggcaacaaaa gcaaaactcc gtctcaaaaa aaaaaaagaa actcaaatat gtgtgacagg  86520
cgattctcac tgcaggctgc cctgtggctg atccaggagc aaggccttaa ccatgtcatc  86580
cccaagcgat tgcttgtaaa ctttcttctg tgcagccttc aacccttatt atgattttct  86640
tctcaggaac caaactgctg tattcaagaa aggcagcttt gtgtaatcat ttatcataaa  86700
tatcttaaga aaaatcctag agattcctaa ttttaggaaa tgggagacct atggtactga  86760
tataatgtgg gctgggcttg ttttctgtca tttgctagat aaatgaactt gagagcctac  86820
tgtaaaatgt ggaagcttct agattgcaga agggctggaa agacactgtt cttttctccc  86880
gagtgatggg atctgtccag tatttagagc tgcctctgag gccatctgat tctaggagac  86940
tctgcctcgt tgaggatatt ttgaggccta actacacatt cctgccccca gagaggtcac  87000
agcctatagc aggctgatgt ttctcatgtc acatggcaca gaaaggcaca ttttcgttct  87060
caggctaaca aagagcttca aaaactatta gaagggacag tggctataag agaagaacct  87120
cagtcaatgt gtgaaattaa ctaggaacct ggctcctgtt tcttttaggt catgtttttc  87180
agcttaggta aaactagagg ctttgataaa gcatgacctc tagaaatcat tgcttttcat  87240
aaatggaagt gggtttgagt tttttctact gattgttagt gcaggtgatg tctacatgcc  87300
cccagaacat attccatgca acaaaaaaag cccaggtcac cgtctttgct gggaacttga  87360
cttttgtgct cactgaattt taagctttct gacagcagcc tggaatcatg gagggataaa  87420
gtacctatta gtaagatgga aaaaggtgtt tcaggttgga gctgcagtct gttgagagta  87480
agctatggga aggcctgtat acgaggggtg gacttttctt ctgtaagtgt ccagagacca  87540
ggcctcctga agagggcatg gggggcttaac ttacctggac tactgtgttt acaatactca  87600
tttatcttga actcctccta acccctgaga attgctacat ttagtatttg ctgagtactt  87660
cctagcatcc tagggaatca atagaacatt ctcccaacca ggctgggtgc ggtggctcat  87720
gtctgtaatc ccagcacttt gggaggccaa ggtaggcaga tcccttgagg ccaggagtgc  87780
aagactagcc tggctgacat ggtgaaaccc cgtctttact aaaaatacaa aagttagcca  87840
ggcatggtgg tacacacctg taatcccagc tacatgggag gagtaggagg caggagaatt  87900
gcttgaacct gggaggtgga ggttgctgtg agccgagatc atgccactgc actccagcct  87960
gggcgacaga gtgagtgaga ctctgtttaa aaaaaaaaaa aaaaaagaac attctcctaa  88020
cctggcttct tcctccaggg gtgtaattaa tcatgtcagt ttcctcattg atacacacac  88080
acacacacta caatcctgta tccattactt ttcaaggtac atttactatt tacgtttggg  88140
gtccttgtct ctttttttaat agtgtttctt aaagtcttgt attatatcag agtacagtaa  88200
catcccagtc aagagcactc tagtaagctc taggaggaaa gcgacttccg gaaggcagtg  88260
gagacctgtc ctgttggggc agcatagggg cagcccctgc ctctggtcag ttctggcgct  88320
caggctcagg gttgcctctg ggctgttctt cccagagact gacaaagggc tcccataagg  88380
cacctgcaga gcctgtgaga agctgaagtc aatgttttcc tgacaccagt tgatctgtgc  88440
aggatccatt gatttaacca cctgctgtgt ggcatgcact gtggtcgatg ccaggaacag  88500
gaattggagg ggcccatgag catggccagt atcacaggct ggaggtgctg ctgcgctctg  88560
accgggcctc ttggggatga gcccatgtca accaccttgc ctccgatggg gtcgggccca  88620
caggttacct ttgtgtgtcc atgaccacac cttcctcccc gacctcatcc aaatctcttt  88680
```

```
cttttccaag cccctgaatc cttcagggct gcaggttttg tttaaagcag agctggtgag  88740
ttgcataggt tgttgcgttg ggactagatg gggtgttcaa agagttggga gttaaaaaac  88800
ataaagggta tttattagga gaaccaagga gtgtaattct cctgttctta atatgcggcc  88860
aggttaatga atgtcacgtg aatgaaccag aaaaaaatga agtgtgccct tgatcagctg  88920
ggttggtgtg cagcaagctg tgtgaccagg ggacagcagt ggtcctgagg gccgtcactg  88980
tctgccgtgc agagcccttc ctcccacggg ggcctacctc acctgtgcca agggcttgtc  89040
tgtggtcagt gacctggata gatctgaatg gggcttcttt ttcgaggagt cttatggcag  89100
gtctctcagt aaagactcca ttcttgatga tcacacattt tggattttcc aaatctgtca  89160
gagaatgggc ttgaggcggg gtttgtgggc actagtttca ctggtttcat ttaccaaaaa  89220
ggggagcaga agtcaagtat ggtggctcat ccctgtaatc ccagaggcaa gagaattgct  89280
tgagcccagg agttcgagac cagcctgagc aacataagga gaccccgtct ccacaaaaat  89340
gaaaaataac attttagtca gacgtggtgg catgcatctg tggtcccagc tgcttgggag  89400
ggtgagatgg gagggttgtt tgagccctgg agttaaagtt gcaatgagct gtgattgcac  89460
cactgcactc tagcctgggt gacagaacga gaccctgtct caaaaaaaaa aaaaaagaaa  89520
gaaaaaaagg aaaaaaaaaa ctcatgcctg taatcccagc actttgggga ccggggtggg  89580
cagatcacga ggtcaggaga tcaagactat cctagccaac atggtgaaac cccgtttcta  89640
ctaaaaatac aaaaattagc caggtgtggt ggcacgtgcc tgtaatccca gttactcggg  89700
aggctgaggc aggagaatcg cttgaaccag ggagtcagag gttgcagtga gctgagatcg  89760
tgccactgta ctccagcctg ggcgacagag tgagactctg tctcaaacca aaaaaaaggg  89820
gtgggggcg ggggcaggag aacagtgaga ggtagggaga ggaaagggga ttctcgctac  89880
acccaaacca gataccatct agaggctaga atctttggga ggctcaaatt ccctagaaag  89940
caggagaagc ttctgtagcc ctcccgcttt cccagtagat taagcccagg gcggctccag  90000
atgtgtgaca tgctctgtgc ccaaccagag cccatcatag gcagaggaat aacacccaca  90060
ccagaagggc cctcggaggt caccacgtcc aagaaccctc tttacagatg aggaaactga  90120
ggcccagaga ggggagagcc acctagcgag ctggtggcgg ctagaccagg agagctgtca  90180
ttccaagcaa gcaaaggcaa cgagacgagc ccagagctgt gctcccatct ctttgttagg  90240
gggcctggga tgccctctca gtgtcatttt gtccaggatg atgctccctc tcttaagcga  90300
ttaatgcgcc cttgctaacc ttttgctatc gctgcctctt caaaccagag gagttgagag  90360
ttccgggccg gcagaggaag gcgcctgaaa ggcccctggc caatgagatt agcgcccacg  90420
tccagcctgg accctgcgga gaggcctctg gggtctctgg gccgtgcctc ggggagaaag  90480
agccagaagc tcccgtcccg ctgaccgcga gccttcctca gcaccgtccc gtttgcccag  90540
cgcctcctcc aacaggaggc cctcaggagc cctccctgga gtggggacaa aaaggcgggg  90600
actgggccga gaagggtccg gcctttccga agcccgccac cactgcgtat ctccacacag  90660
agcctgaaag tggtaaggtg gtccaggaag gcttcctccg agagccaggc cccccaggtc  90720
tgagccacca gctcatgtcc ggcatgcctg gggctcccct cctgcctgag ggccccagag  90780
aggccacacg ccaaccttcg gggacaggac ctgaggacac agagggcggc cgccacgccc  90840
ctgagctgct caagcaccag cttctaggag acctgcacca ggaggggccg ccgctgaagg  90900
gggcaggggg caaagagagg ccggggagca aggaggaggt ggatgaagac cgcgacgtcg  90960
atgagtcctc cccccaagac tcccctccct ccaaggcctc cccagcccaa gatgggcggc  91020
```

```
ctccccagac agccgccaga gaagccacca gcatcccagg cttcccagcg gagggtgcca  91080
tccccctccc tgtggatttc ctctccaaag tttccacaga gatcccagcc tcagagcccg  91140
acgggcccag tgtagggcgg gccaaagggc aggatgcccc cctggagttc acgtttcacg  91200
tggaaatcac acccaacgtg cagaaggagc aggcgcactc ggaggagcat ttgggaaggg  91260
ctgcatttcc aggggcccct ggagaggggc cagaggcccg gggcccctct ttgggagagg  91320
acacaaaaga ggctgacctt ccagagccct ctgaaaagca gcctgctgct gctccgcggg  91380
ggaagcccgt cagccgggtc cctcaactca aaggtctgtg tcttgagctt cttcgctcct  91440
tccctgggga cctcccaggc ctcccaggct gcgggcactg ccactgagct tccaggcctc  91500
ccgactcctg ctgcttctga cgttcctagg acgccactaa atcgacacct gggtgcagct  91560
gctccactcc ctcggcctcc tcccgtgctc aggctgtggc cgcacgcgcc cctcacgctt  91620
gcccgccact ctgcatgtca ccagcacccc cgctccgtgc tccccacctt gtttgactct  91680
ctggccactt gatttgtcca caacggccca tcagcccaca ggaggtttgg tgggtgcctt  91740
ccaccgacag gatgacgggt gccctcatgg tgtctagaac tctccaaccc tcccatgtag  91800
gcataagcag ccccactttg cagatgagga aacggaggct cagagaagta cagtaacttg  91860
ccgaaggcca atgagtagta agtgacagag ccaggtttgg gatccaggta ggttgtctct  91920
gaaagacacg cctgtcctgc atcccacaac gcctcccagg aggtgctgga gtgtggacgc  91980
ctaacacaga gatgtgcagg gcacacacag caggtgacac acacagcatc cagaggtggc  92040
ccagagctca tgctgtgcct ttggcccagt gccctgcccc cacccactct gccttgtggc  92100
aggaagacaa ggagcagaca caagatctcc ctggtccaca tgccaccacc tccctctgca  92160
gaggacaagg ggatcctcat gctggcattg gagggggttg agcagggccc accttgagcc  92220
ctcaggagca cgaccacagc agccctgcag ggagggattg gtgggaggag agtcccaagt  92280
atcagggaga ggagagttgg tgtcccacag gagacctcag agccacaagg cgagcttgtt  92340
cataaatttg ggacccttag catttcacag ttatttgcag agcccagaaa tggatgttac  92400
tgaagctcac agttgcaagc atctgttaaa tttttattag attttacttt tagggaaaac  92460
tttgaaatgc tataaagaag cctgtgttta aaagttaaga cagaggctgg gggcgatggc  92520
tcacgcctgt aatctcagca ctttgggagg ccaaggcagg tggatcattt gaggttagga  92580
gttcgagacc agcctggcca acatggtgag accctgtctc tactaaaatt acaaaaaatt  92640
agctgggcgt ggtggcgggc acctgtagtc ccagctactg gggaggctga agcaggataa  92700
gtgcttgaac ccaggaggcg gaggttacag tgagccaaga tcacaccact gtaccctaag  92760
cctgggcgac agagtgagac tctgtctcaa aaaataaaat aaaataaagt taagagagaa  92820
aaaaatatat cctatatcct ttgttaaatt ccaaaacagt aggggacaaa taactgactt  92880
gacaggttac tacaatattt cctgaaatga tgttttcttg aatactggcc tactagaggt  92940
tcataggtgt gtttggatta aaaaagagtt ccatggccca gtgactgggg gaaaaaaata  93000
aaagactaaa gtaagttaaa caggcttttc tgctgcagga cttgtcagag cctttaatgt  93060
actaatggcc attgtgaccc tctgagaagg tcacagagtg ggtttcccaa acttacttga  93120
ttctacctgc taacatttcc tggaggaagt ttgggaaatg ccgatttagc agattctttt  93180
gttgtgccgt ggatggtgct ggttgatgtg ggcaaaacaa agaacacgtg agtcagatcc  93240
gcctggggct cttactaaag tgcaggttcc caggtgccac tttaggctta cagacccagt  93300
tgtggggtaa gcctgggagt cttttagcag gtgattctgc cacatagtat agttggaaaa  93360
cctctgggca tactcattgc tggtccctct agaaatccag gtgacaatag ccaatgagaa  93420
```

```
gctccaagag acccagttgt ccatggggta gagggaatgt gatattgaaa ccaaagaaga  93480
aaatctatga tcagttttca gcagtgactg tcaagagaag gagaagggtg agttagcgct  93540
gatgctggct gacaggtcag cgggttggtt tcaccaagga gtgtgatgaa ggctgatgtt  93600
gtctgtggga atgtatgatg gtaactggtt tgtagctaat ttggggaagc agtgagaatt  93660
cgtgcccttt gaagaccagt aagtggcaag aaacccacca ggcctggctc agggctgggc  93720
tgggcttggc tcgtctcaga gcagctgggg ctggtggcca aagccaccat tagtgagggg  93780
caggccctgg gggtacaacc agcaactagg ggacaaagac aaccctgcca gcctctccta  93840
ttctggaggc gtgtgaccag aaatggagat gggttggtca gcataagatg gccaggaagg  93900
tggaaatcag gactgctggc aatctagcca catgggcagg ggagccgggt ggttccaggc  93960
agtttccaag gccaagaggg tgagcaggca cctcacaggg aatcagggcc aagcctggct  94020
gcagtgtgga gacaatgcac ccaccccat ccttggatct tgcaggaggc tgggtcctca  94080
ctgagctacc aacatccatg gccctgaggc ttttaaaaca cccatccatg gagtggggct  94140
ggtcccagtg gggtgaggct gaccctggca gaaacagggc aggagcctgt gggttaggga  94200
gactgcacct tccttagata gcctccatgc catcatgtcc ccgtgacagt ttctgctgcg  94260
tcccctctgc atggtcccac cctcggccag cctgctgccc cctcttgcca ggttgcgcta  94320
atcagtgacc ccagtgtgct gtgttgatac taacaatgcg aggcctagca gattcaaggg  94380
aaaagagaac caactgggtt tccaccagac ccaactaaac aaacatggac ctatcccaga  94440
gaaatccagc ttcaccacag ctggctttct gtgaacagtg aaaatggagt gtgacaagca  94500
ttcttatttt atattttatc agctcgcatg gtcagtaaaa gcaaagacgg gactggaagc  94560
gatgacaaaa aagccaaggt aagctgacga tgccacggag ctctgcagct ggtcaagttt  94620
acagagaagc tgtgctttat gtctgattca ttctcatata taatgtgggg agtatttgtc  94680
actaaagtac agctgtcatt taaagtgctt tgtattttgg ggcaggcttt taaaaagtcc  94740
agcatttatt agttttgata cttaccccag ggaagagcag ttggcaggtt catgaagtca  94800
tgctcctaat tccagctttc ttagtgtact ttcagtgaga ccctgacagt aaatgaaggt  94860
gtgtttgaaa accaaaccca ggacagtaaa tgaaggtgtg tttgaaaacc agccctagga  94920
cagtaaatga agccatcttc tcactgcata aactgcaccc agatctttgc ccatccttct  94980
cagtatttca cttcacccat tgtttactgt ctcaatgact ggggaaatgt ctggggaaat  95040
gctcccgtaa ttgcacagtg gcgtttttcc tggaaaatcc caccatggct ctagataaga  95100
cctatttttc ttaaaggtat ctaaaatttc cagcataaat tctgtctgaa acacctgaat  95160
tttaatcagt actggagccc ggagggcatc tccagttgcc acatagctct gagcattcag  95220
tggtgtgttg agggctgctc ccggaagtgc ctgcagagtc agggctcccc agcctcatct  95280
agtgaggcag tggaagggcc tgtggggatt tggagagctg gcctgggtct ctgaagtgat  95340
agtgacagct gcttgtcaat cacggtgcac atttagtgcc gggggcaggg ggcagggaat  95400
accagcctca tgcatgcatg cattcatttg ttccttcctt cattcattca ttcagtacac  95460
atgggtacaa catccctgcc ctggagttgc ccagagtcta gggaggggaa agatctatta  95520
ccctgggcct cggccagctg gggagtgctg ctggtggaga ggggccgtgt gcagcgaggg  95580
aaggaggagt cgtcaatacc cccaccccag ctttgctttc ttgtcatcag ccccagggcc  95640
ccagcctgtg tccctcctct cccattgcta cttcatctcc tgggtcctcc ttaccaagcc  95700
tgaccacaca gagggccttg gccgcttcca tggggaattg gaaagcaata agatagcatc  95760
```

ccctagaagc ccagtgaagt ctgggacagg acccttctct gagctctgac ttgctcttgg 95820
aaacacttcg aggcttagcc tccccacttt gtttcccaag agtgtgacct gttcccctcc 95880
aaacaccccc ttctcctcca gggccatgcc cacccgtcaa aatcccccac gggcaggacg 95940
aactgtgggt gtcagtcacc atctatcctg catcctggtt ccagggcccc ccccagcccc 96000
gcctccatag ggacaggcgt gcagacaccc gtccctggct gcttcctctt gtggaatggg 96060
ttcaaaagta agcagtgttg tttacactga caaactgaaa aaaaaagaaa aagagataac 96120
attggaggct tggcacagtg gctcatgcct gtaatcccag cactttggga ggctaaggtg 96180
ggaggatgtc cccagcccaa gagttctaga ccagcctggg caacatagca agaccccatc 96240
tcaaaaaaaa aatttaattg gccaggcaga ggtgggagga tcacttgaac ccaaagggtg 96300
gaggctgcag tgagccgtga tggcaccact gcactccagc cagggcaaca gagggagacc 96360
ctgtctctaa aacaaacaaa caaacaaaca aacaaaagag ttaacattgg ccagattagg 96420
attcaccaga tagtgttaat attagtttga tttgagactt taatcagaaa gcacatgtgt 96480
ggtgggggtg ggtgtaacct aagtcaggta gaatctttcc aacttggggg gggcacactc 96540
ctgattgtag ccatatgagt ctgtcagtgt ggtggaagag accatgggtt aatgggcagg 96600
taaaaaagca ccttgcctgg aattgagtag aaagtaaggc ccttcagacc ccgtgacaca 96660
cttggggaca ttttcttgag taacatccta agattcatgt accttgatga tctccatcaa 96720
cttactcatg tgaagcacct ttaaaccagt cgtctccaaa ttcaggggca cagtaacatc 96780
caacaggctg gagaaagaac gtactagaac ttccattcct ttttcatgtc ctcttctaaa 96840
agctttgtca gggccaggcg cggtggctca cgcctgtaat cccagcactt tgggaggccg 96900
agacgggtgg atcacgaggt caggagatcg agaccatcct ggctaacaca gtgaaacccc 96960
atctctacta aaaatacaaa aaaacgagcc gggcgtggtg gtgggcgcct gtagtcccag 97020
ctactcggga ggctgaggca ggagaatggc gtgaacccag gaggcagagc ttgcagtgag 97080
ccgagattgc accactgcag tccagcctgg gcgacagagc gagactccgt ctcaaaaaag 97140
aaaaagaaaa agaaaaagaa ctgtgattgg ggaggacggt cactttcctg ttcttactga 97200
tcagaaggga tattaagggt acctgattca aacagcctgg agatcactgc tttcaaccat 97260
tacctgcctt atttattttt agttactgtc ctttttttcag tttgtttccc tcctccatgt 97320
gctgactttt attttgattt tatttatgtt tatgtttaag acatccacac gttcctctgc 97380
taaaaccttg aaaaataggc cttgccttag ccccaaacac cccactcctg gtagctcaga 97440
ccctctgatc caaccctcca gccctgctgt gtgcccagag ccaccttcct ctcctaaaca 97500
cgtctcttct gtcacttccc gaactggcag ttctggagca aaggagatga aactcaaggt 97560
aaggaaacca cctttgaaaa gaaccaggct gctctgctgt ggtttgcaaa tgtggggttt 97620
gtttatttgt tttttagcct caaagacctt tcttcaaatg agttctggca tagaagcacc 97680
gtgtaaaata gttagaattc tgggcaaagg ggaaaagaga gctgggggcc atccctctca 97740
gcaccccaca ggctctcata gcagcagctc ctaagacacc tggtgggacc ttggtttcga 97800
aatcgctact ctaaggctgg gcacggtggc tcacacctgt aatcccagct ctttaggagg 97860
ccgaggaggg tggatcacct gagatcagga gttcgagacc agcctggcta acatggcaaa 97920
accctgtctc tactaaaaat acaaaaatta gccgggcgtg gtgttatgcg tggtggtaat 97980
cgcagctact cgggaggctg aggcacaagg attgcttgaa ccccagaggc agaggttgta 98040
gttagctcca gcttgggcga cagagcaaga ccctgtcgca aaaattgttt aaaaaacaaa 98100
cccaaaattg ctactctcat tgggttcctt tgcccattcc tgattttggc aagagaaatg 98160

```
cttccagatt gccctgatct gggtaggaca gcatcacgcc atagcaacac tgccccgtga  98220
gctcactgcc ccctcaacta gcttgtggtc cttggttaat gtcagtttct tttttgagtt  98280
tgtgttatgt ctaagggtca tctgctgggt aacggaaccc agggactgcc ctagtcccta  98340
gactgtgcca tgcccgactc tgccagcttt gtcagtgatg ctggtgctcg cctcctcggg  98400
tgctcgcctg gtctgagcac acccaaggag ttcttgaggc cttagggttg tttgcgagag  98460
aatgaaagaa cacgacctag ctctctttag catccttggt caggttcaac actgccccca  98520
ggggcctctg gtggagccaa ccaccatcag ccaaataaat ccataattag agtcagaaaa  98580
tggatgtctg catatgtgta gtgcactaat gtcctgccga tgattgacat ggagtggaga  98640
gtgacctgat cattgctgtg agctctgctg gccttggcac aactcatgct gataactaat  98700
gcacacagtt cctctgggag gaaatgtcct cagggaactt ggagtttggg tggggatgtg  98760
ggtttgtgtg cccagcaagc ccttgtggtt gtagcagaca ctagtggcat ctaggaggca  98820
aagggtcacc ccagtcttag ccacgttttg agtcaaggtg gcggagtggg gctggtgttg  98880
actcttggtg gcagtaactt ttcccaatgg tgaaaaaccc ctctatcatg tttcatttac  98940
agggggctga tggtaaaacg aagatcgcca caccgcgggg agcagcccct ccaggccaga  99000
agggccaggc caacgccacc aggattccag caaaaacccc gcccgctcca aagacaccac  99060
ccagctctgg taagaagaac gttctcttga atcttagagg aagctgaagc tctcagaggt  99120
acagccttca ttttaggagg ccttaggcca ctgagaatga ataacccctg gcagctggtc  99180
agcagcttgc agtttactaa gcactggagt cttcattgcc ttctcagtcc ttttgatttc  99240
tgaggcaaat gttgaatccc tacctttttt tttttttttc ttttgagaca gagtttcgct  99300
tttgttatcc aggccggagt gcagtggtgt gatctcagct cactgcatcc tccacctccc  99360
aggttcaagc gattctccta cctcagcctc cctagtagct gggattacag gcacctgcca  99420
ctatgcccgg ctaatttttt gtatttttag tagagacagg gtttcaccat gttggccagg  99480
ctggtctcga acgcctgacc tcaggtgatc cacctgcctc ggcctcccaa agtgctggga  99540
ttacaggcat gagccaccac tcccagcctg aatcctcact ttttatcaat gaagaaattg  99600
aggctgattc tgcagcatga taaaaaaaaa tacagaaaaa ggaaaaaaaa gaaagaaatc  99660
gagcctctga gagtttgctt gactgagtct aaccagctca ttttaaaccc gaggaaaatg  99720
cagtcacatg actactaagt ggcagctctc ggagcctctc tggccccaag tccagggttc  99780
catagaggca gccccagcat ggcatgtttt cagtccccaa atgagactct ggagacaaat  99840
gtctctggag acagagcagc agcctggata agtcacaatg ggtgacgtca ctcagggctc  99900
aacccctggg cagcttaact tgctagggac gttaggagtc tgctgcaaaa cctgagggtc  99960
ttagctgagc agtcacaggc tgggcccgtt gccctgggct cctgtgagta aaacccagtc 100020
aattttgagt acccagtaag gcatccattg agttattttg cagccaggag tgctattaag 100080
aacagtcgcg gctgggcgtg gtggctcatg cctgtaatcc cagcactttg ggaggccaag 100140
gtgggcggat cacctgaggt caggagttcg agaccagctt ggccaacatg gcaaaacccc 100200
gtctctaata aaaatacaaa ataattagct gggcgtggtg gcgggcgcct gtaatcccag 100260
cttctcagga gggtgaggaa ggagaatcac ttgaacccag gaggcagagg ttgcagtgag 100320
ctgagatcgc accattgcac tccagcctgg atgacaaaag tgagattcct tctcaaaaaa 100380
aaaaaaaaaa aaacagtcgt cctctttggg gattagggac agcctgcctg cctgcccgag 100440
cacttctctc ttccattgcc ccagtgaagt attccaggcc cctgggttta gactctgcac 100500
```

catgtagggg tgtctgacct gcacttgctc cttggtggca cgggcagcct atggcacttg 100560
ctgcgggctg tgaccaaagc ctggcctgga tcttggatct tggtgactct gcttctccct 100620
ggcctgaggg agctgcccag agcctgccca ccacctgctg cgtgtctttg cggtggcatt 100680
tctcgcacac atgccgtgcg gtggcacccc caaggatggc cattcactaa ggcccattgt 100740
ttttgtcttt tcgcttcgtg ttttctggcc tggtgttttt ctcatataca tgtgatccag 100800
ggataattcc cagaattttg acaggatttt aagtagcgtt tggatcctgc tgtttttttt 100860
tcacttaaca tcgggccagt tgactcacac tctgtttttt gttgttgttt ttttgagacg 100920
gagtctcact gtgtcaccca ggctgaagtg cagtggcaca atcttggcat actgcaacct 100980
ctgcttccca aattcaagca gttttcctgc ctcagcctcc tgagtagctg ggactacagg 101040
cacaggccac cacgccctgc taatttttgt atttttagta aagacagggt ttcaccattt 101100
tggccagcct agtctcgaac tcctgacctc aagtgatccg cccacctcgg cctcccaaag 101160
tgctgggatt acaggggact cacactttgt aacaacctga aacaacgtga tgcatttccc 101220
tttgggtctt acctgctctt cggtggctgc ctgcaggtgg agagaccctc cccttgggc 101280 ccctcgacct tgtttcagaa tggggcccct gctgggccag ctgtgggtgc ctgccacgtg 101340
aaggactcat taaggccctg tttaagcctg atgataataa ggctttcgtg gatttttctc 101400
tttaagcgac taagcaagtc cagagaagac cacccccctgc agggcccaga tctgagagag 101460
gtactcggga gcctacttcg ctgggagcag cctccctttg cgtgtgtggc cattcactgg 101520
cttgtgtttc tagagccggg aggacccttt tctgcaatgc agggttcaca cagggttcgc 101580
agcctgaaga tggagcagtc cgaattctct tccctgtgca gtttgcgcag ctgtgtttgt 101640
ctgatgggct ttctaatcct gtgtgctctc cttgacttca gggacaatgg cattacaggc 101700
atgagccacc atgcctggct gtctccctat gtttcagatg aagacatagg cttaaggagg 101760
tcaggtgact tgcccacgac cactctgtaa ataagaggca tgaaaagtat ttggagccac 101820
caccaccaag cccactggtc accctgggtc tctgaagtca gggaggcagg aggatgggag 101880
gtctgaggag gcagagaggc tgagcctgga ggccctggag gccgaggccc catctgttgt 101940
ttccttatgt ggaaaataag aggcttcatt tgtcctattg ccacagagcg tactacttca 102000
ggaacatcca agacatggaa atccgcaggg cacggtggct cacgtctata atcccggcac 102060
tttgggaggt tgaggtggga gaatcgcttg aggccagaag ttcaagacca gcctgagcaa 102120
catagtcaga ccccgtctct ataaaaaaca ttatttttaa aaaagacatg gaagtcaaat 102180
tctaaaaact ggtgctggct gggtgcggtg gctcatgcct ataatcccag cactttggga 102240
ggccgaggcg ggtggatcac ctgaggtcag gagttcaaga ccagcctggc caacatggta 102300
aaacctctac taaagaaatc tttactgaaa atacaaaaat ccagtctcta ctaaaataag 102360
tctctactaa aaatacaaaa attagccagg cgtggtgctg cacacctgta atatcagcta 102420
ctcgggaggc tgaggcagga gactcgcttg atcccatgca gcggaggttg cagtgagccg 102480
agatcacgcc attgcactcc agcctgggca tcagaataag actccgtctc aaaaaaaaaa 102540
ccacaaaaaa acaaaacaac aacaaaagaa aactagtgct tattcgtcac tggccaagct 102600
gcccattggc tacatgggtg cttcaaagag ctgcccttct ccaggtctgg ccagcaggta 102660
tgtgttacag caaatgcctg gggcagcggc aggggcattg ctgcgggaag cttctggact 102720
tgcaggaaag ctaagttctc agactgcagg ggagctaagc acacctcggc acagggtgag 102780
gcctgcggtt ctcagacttc agtctttgtg gagcttgaga aaaatgaggc tttgcaggtc 102840 ccaccctag agattctgct ctatccactc ttgaagggga tcgagaaatt tgcattttgc 102900
aactcccact ttcctccttg aaagctccgg agattctgac gcagggttcc gtgggccaca 102960
ctttggaaaa tacagaccca tgagatagaa taccagactg ttgaagtgta acgggggcct 103020
gggaagtgca gtaacagaag caagtttgag ggtaaaggac acccagagga gggagggaca 103080
gcatctgcat ggagaggaga agagaccccc cagcagcttc cagggtgttg gaagggtgcg 103140
ctagtaactg ctatgcatgg caggtgggga actgtacgtc agggcacagc agcatgaagc 103200
ggtatggctc gtgtggacag ctagggacag gcaggcgtgg agcaggcatc ctgttctgaa 103260
ggccaaatcc cacagaggag ccagggtgct ggcaggagcc ctgaactagc cgaacagctg 103320
aacagctgaa cattcaccct gtggggaaag ggtcagaagc gtccaggctt gagggcacag 103380
ctgggtctcg tcactgcatc acccttattt aggataaagg ccctgaagaa ttgtattaga 103440
ggttggcaaa gcatatctac cacctcctgg agccacgctg gccgcaggga ttataattat 103500
ttccattttc aaattaaggc ctctgagctc agagagggga agttacttgt ctgaggccac 103560
acagcttgtt ggagcccatc tcttgaccca aagactgtgg agccgagttg gccacctctc 103620
tgggagcggg tattggatgg tggttgatgg ttttccattg ctttcctggg aaaggggtgt 103680
ctctgtccct aagcaaaaag gcagggagga agagatgctt ccccagggca gccgtctgct 103740
gtagctgcgc ttccaacctg gcttccacct gcctaaccca gtggtgagcc tgggaatgga 103800
cccacgggac aggcagcccc cagggccttt tctgacccca cccactcgag tcctggcttc 103860
actcccttcc ttccttccca ggtgaacctc caaaatcagg ggatcgcagc ggctacagca 103920
gccccggctc cccaggcact cccggcagcc gctcccgcac cccgtccctt ccaaccccac 103980
ccacccggga gcccaagaag gtggcagtgg tccgtactcc acccaagtcg ccgtcttccg 104040
ccaagagccg cctgcagaca gcccccgtgc ccatgccaga cctgaagaat gtcaagtcca 104100
agatcggctc cactgagaac ctgaagcacc agccgggagg cgggaaggtg agagtggctg 104160
gctgcgcgtg gaggtgtggg gggctgcgcc tggaggggta gggctgtgcc tggaagggta 104220
gggctgcgcc tggaggtgcg cggttgagcg tggagtcgtg ggactgtgca tggaggtgtg 104280
gggctccccg cacctgagca cccccgcata acaccccagt cccctctgga ccctcttcaa 104340
ggaagttcag ttctttattg ggctctccac tacactgtga gtgccctcct caggcgagag 104400
aacgttctgg ctcttctctt gccccttcag cccctgttaa tcggacagag atggcagggc 104460
tgtgtctcca cggccggagg ctctcatagt cagggcaccc acagcggttc cccacctgcc 104520
ttctgggcag aatacactgc cacccatagg tcagcatctc cactcgtggg ccatctgctt 104580
aggttgggtt cctctggatt ctggggagat tgggggttct gttttgatca gctgattctt 104640
ctgggagcaa gtgggtgctc gcgagctctc cagcttccta aaggtggaga agcacagact 104700
tcgggggcct ggcctggatc cctttcccca ttcctgtccc tgtgcccctc gtctgggtgc 104760
gttagggctg acatacaaag caccacagtg aaagaacagc agtatgcctc ctcactagcc 104820
aggtgtgggc gggtgggttt cttccaaggc ctctctgtgg ccgtgggtag ccacctctgt 104880
cctgcaccgc tgcagtcttc cctctgtgtg tgctcctggt agctctgcgc atgctcatct 104940
tcttataaga acaccatggc agctgggcgt agtggctcac gcctataatc ccagcacttt 105000
gggaggctga ggcaggcaga tcacgaggtc aggagttcga gaccaacctg accaacaggg 105060
tgaaacctcg tctctactaa aaatacaaaa atacctgggc gtggtggtgg tgcgcgccta 105120
taatcccagc tactcaggag gctgaggcag gagaatcgct tgaacccagg aggcagaggt 105180
tgcagtgagc cgagatagtg ccactgcact ccagtttgag caacagagcg agactctgtc 105240

```
tcaaaacaaa ataaaacaaa ccaaaaaaac ccaccatggc ttagggccca gcctgatgac 105300
ctcatttttc acttagtcac ctctctaaag gccctgtctc caaatagagt cacattctaa 105360
ggtacggggg tgttggggag gggggttagg gcttcaacat gtgaatttgc ggggaccaca 105420
attcagccca ggaccccgct cccgccaccc agcactgggg agctggggaa gggtgaagag 105480
gaggctgggg gtgagaagga ccacagctca ctctgaggct gcagatgtgc tgggccttct 105540
gggcactggg cctcggggag ctagggggct ttctggaacc ctgggcctgc gtgtcagctt 105600
gcctccccca cgcaggcgct ctccacacca ttgaagttct tatcacttgg gtctgagcct 105660
ggggcatttg gacggagggt ggccaccagt gcacatgggc accttgcctc aaaccctgcc 105720
acctcccccc acccaggatc ccccctgccc ccgaacaagc ttgtgagtgc agtgtcacat 105780
cccatcggga tggaaatgga cggtcgggtt aaaagggacg catgtgtaga ccctgcctct 105840
gtgcatcagg cctcttttga gagtccctgc gtgccaggcg gtgcacagag gtggagaaga 105900
ctcggctgtg ccccagagca cctcctctca tcgaggaaag gacagacagt ggctcccctg 105960
tggctgtggg gacaagggca gagctccctg gaacacagga gggagggaag gaagagaaca 106020
tctcagaatc tccctcctga tggcaaacga tccgggttaa attaaggtcc ggccttttcc 106080
tgctcaggca tgtggagctt gtagtggaag aggctctctg gaccctcatc caccacagtg 106140
gcctggttag agaccttggg gaaataactc acaggtgacc cagggcctct gtcctgtacc 106200
gcagctgagg gaaactgtcc tgcgcttcca ctggggacaa tgcgctccct cgtctccaga 106260
ctttccagtc ctcattcggt tctcgaaagt cgcctccaga agccccatct tgggaccacc 106320
gtgactttca ttctccaggg tgcctggcct tggtgctgcc caagacccca gaggggccct 106380
cactggcctt tcctgccttt tctcccattg cccacccatg cacccccatc ctgctccagc 106440
acccagactg ccatccagga tctcctcaag tcacataaca agcagcaccc acaaggtgct 106500
cccttccccc tagcctgaat ctgctgctcc ccgtctgggg ttccccgccc atgcacctct 106560
gggggcccct gggttctgcc ataccctgcc ctgtgtccca tggtggggaa tgtccttctc 106620
tccttatctc ttcccttccc ttaaatccaa gttcagttgc catctcctcc aggaagtctt 106680
cctggattcc cctctctctt cttaaagccc ctgtaaactc tgaccacact gagcatgtgt 106740
ctgctgctcc ctagtctggg ccatgagtga gggtggaggc caagtctcat gcatttttgc 106800
agcccccaca agactgtgca ggtggccggc cctcattgaa tgcggggtta atttaactca 106860
gcctctgtgt gagtggatga ttcaggttgc cagagacaga accctcagct tagcatggga 106920
agtagcttcc ctgttgaccc tgagttcatc tgaggttggc ttggaaggtg tgggcaccat 106980
ttggcccagt tcttacagct ctgaagagag cagcaggaat ggggctgagc agggaagaca 107040
actttccatt gaaggcccct ttcagggcca gaactgtccc tcccaccctg cagctgccct 107100
gcctctgccc atgaggggtg agagtcaggc gacctcatgc caagtgtaga aaggggcaga 107160
cgggagcccc aggttatgac gtcaccatgc tgggtggagg cagcacgtcc aaatctacta 107220
aagggttaaa ggagaaaggg tgacttgact tttcttgaga tattttgggg gacgaagtgt 107280
ggaaaagtgg cagaggacac agtcacagcc tcccttaaat gccaggaaag cctagaaaaa 107340
ttgtctgaaa ctaaacctca gccataacaa agaccaacac atgaatctcc aggaaaaaag 107400
aaaaagaaaa atgtcataca gggtccatgc acaagagcct ttaaaatgac ccgctgaagg 107460
gtgtcaggcc tcctcctcct ggactggcct gaaggctcca cgagcttttg ctgagacctt 107520
tgggtccctg tggcctcatg tagtacccag tatgcagtaa gtgctcaata aatgtttggc 107580
tacaaaagag gcaaagctgg cggagtctga agaatccctc aaccgtgccg gaacagatgc 107640
```

taacaccaaa gggaaaagag caggagccaa gtcacgtttg ggaacctgca gaggctgaaa 107700
actgccgcag attgctgcaa atcattgggg gaaaaacgga aaacgtctgt tttccccttt 107760
gtgcttttct ctgttttctt ctttgtgctt ttctctgttt tcaggatttg ctacagtgaa 107820
catagattgc tttggggccc caaatggaat tattttgaaa ggaaaatgca gataatcagg 107880
tggccgcact ggagcaccag ctgggtaggg gtagagattg caggcaagga ggaggagctg 107940
ggtggggtgc caggcaggaa gagcccgtag gccccgccga tcttgtggga gtcgtgggtg 108000
gcagtgttcc ctccagactg taaaagggag cacctggcgg gaagagggaa ttcttttaaa 108060
catcattcca gtgcccgagc ctcctggacc tgttgtcatc ttgaggtggg cctcccctgg 108120
gtgactctag tgtgcagcct ggctgagact cagtggccct gggttcttac tgctgacacc 108180
taccctcaac ctcaaccact gcggcctcct gtgcaccctg atccagtggc tcattttcca 108240
ctttcagtcc cagctctatc cctatttgca gtttccaagt gcctggtcct cagtcagctc 108300
agacccagcc aggccagccc ctggttccca catccccttt gccaagctca tccccgccct 108360
gtttggcctg cgggagtggg agtgtgtcca gacacagaga caaaggacca gcttttaaaa 108420
cattttgttg gggccaggtg tggtggctca cacctaatcc caacacctgg ggaggccaag 108480
gcagaaggat cacttgagtc caggagttca agaccagcct gggcaacata gggagaccct 108540
gtctctacaa ttttttttt aattagctgg gcctgttggc actctcctgt agttccagct 108600
actctagagg ctgaggtggg aggactgctt gagcctggga ggtcagggct gcaatgagcc 108660
atgttcacac cactgaacgc cagcctgggc gagaccctgt atcaaaaaag taaagtaaaa 108720
tgaatcctgt acgttatatt aaggtgcccc aaattgtact tagaaggatt tcatagtttt 108780
aaatactttt gttatttaaa aaattaaatg actgcagcat ataaattagg ttcttaatgg 108840
aggggaaaaa gagtacaaga aaagaaataa gaatctagaa acaaagataa gagcagaaat 108900
aaaccagaaa acacaacctt gcactcctaa cttaaaaaaa aaaatgaaga aaacacaacc 108960
agtaaaacaa catataacag cattaagagc tggctcctgg ctgggcgcgg tggcgcatgc 109020
ctgtaatccc aacactttgg gaggccgatg ctggaggatc acttgagacc aggagttcaa 109080
ggttgcagtg agctatgatc ataccactac accctagcct gggcaacaca gtgagactga 109140
gactctatta aaaaaaaaat gctggttcct tccttatttc attcctttat tcattcattc 109200
agacaacatt tatggggcac ttctgagcac caggctctgt gctaagagct tttgccccca 109260
gggtccaggc caggggacag gggcaggtga gcagagaaac agggccagtc acagcagcag 109320
gaggaatgta ggatggagag cttggccagg caaggacatg caggggggagc agcctgcaca 109380 agtcagcaag ccagagaaga caggcagacc cttgtttggg acctgttcag tggcctttga 109440
aaggacagcc cccacccgga gtgctgggtg caggagctga aggaggatag tggaacactg 109500
caacgtggag ctcttcagag caaaagcaaa ataaacaact ggaggcagct ggggcagcag 109560
agggtgtgtg ttcagcacta aggggtgtga agcttgagcg ctaggagagt tcacactggc 109620
agaagagagg ttggggcagc tgcaagcctc tggacatcgc ccgacaggac agagggtggt 109680
ggacggtggc cctgaagaga ggctcagttc agctggcagt ggccgtggga gtgctgaagc 109740
aggcaggctg tcggcatctg ctggggacgg ttaagcaggg gtgagggccc agcctcagca 109800
gcccttcttg gggggtcgct gggaaacata gaggagaact gaagaagcag ggagtcccag 109860
ggtccatgca gggcgagaga gaagttgctc atgtggggcc caggctgcag gatcaggaga 109920
actggggacc ctgtgactgc cagcggggag aagggggtgt gcaggatcat gcccagggaa 109980
gggcccaggg gcccaagcat ggggggggcct ggttggctct gagaagatgg agctaaagtc 110040
actttctcgg aggatgtcca ggccaatagt tgggatgtga agacgtgaag cagcacagag 110100
cctggaagcc caggatggac agaaacctac ctgagcagtg gggctttgaa agccttgggg 110160
cggggggtgc aatattcaag atggccacaa gatggcaata gaatgctgta actttcttgg 110220
ttctgggccg cagcctgggt ggctgcttcc ttccctgtgt gtattgattt gtttctcttt 110280
tttgagacag agtcttgctg ggttgcccag gctggagtgc agtggtgcga tcatagctca 110340
ctgcagcctt gaagtcctga gctcaagaga tccttccacc tcagcctcct gagtagttgg 110400
gaccacaggc ttgcaccaca gtgcccaact aatttcttat attttttgta gagatggggt 110460
ttcactgtgt cgcccaggat ggtcttgaac tcctgggctc aagtgatcct cctgcctcag 110520
cctcgcaaat tgctgggatt acaggtgtga gccaccatgc ccgaccttct ctttttaagg 110580
gcgtgtgtgt gtgtgtgtgt gtgtgggcgc actctcgtct tcaccttccc ccagccttgc 110640
tctgtctcta cccagtcacc tctgcccatc tctccgatct gtttctctct ccttttaccc 110700
ctctttcctc cctcctcata caccactgac cattatagag aactgagtat tctaaaaata 110760
cattttattt atttattttg agacagagtc tcactctgtc acccaggctg gagtgcagtg 110820
gtgcaatctc ggctcactgc aacctccgcc tcccaggttg aagcaactct cctgcctcag 110880
cctccctagt agctgggatt acaagcacac accaccatgc ctagcaaatt tttatatttt 110940
tagtagagga ggagtgtcac catgtttgcc aagctggtct caaactcctg gcctcaggtg 111000
atctgcctac cttggtctcc caaagtgctg ggattacagg tgtgagccac cacgcctgcc 111060
cttaaaaata cattatattt aatagcaaag ccccagttgt cactttaaaa agcatctatg 111120
tagaacattt atgtggaata aatacagtga atttgtacgt ggaatcgttt gcctctcctc 111180
aatcagggcc agggatgcag gtgagcttgg gctgagatgt cagaccccac agtaagtggg 111240
gggcagagcc aggctgggac cctcctctag gacagctctg taactctgag accctccagg 111300
catcttttcc tgtacctcag tgcttctgaa aaatctgtgt gaatcaaatc attttaaagg 111360
agcttgggtt catcactgtt taaaggacag tgtaaataat tctgaaggtg actctaccct 111420
gttatttgat ctcttctttg gccagctgac ttaacaggac atagacaggt tttcctgtgt 111480
cagttcctaa gctgatcacc ttggacttga agaggaggct tgtgtgggca tccagtgccc 111540
accccgggtt aaactcccag cagagtattg cactgggctt gctgagcctg gtgaggcaaa 111600
gcacagcaca gcgagcacca ggcagtgctg gagacaggcc aagtctgggc cagcctggga 111660
gccaactgtg aggcacggac ggggctgtgg ggctgtgggg ctgcaggctt ggggccaggg 111720
agggagggct gggctctttg gaacagcctt gagagaactg aacccaaaca aaaccagatc 111780
aaggtctagt gagagcttag ggctgctttg ggtgctccag gaaattgatt aaaccaagtg 111840
gacacacacc cccagcccca cctcaccaca gcctctcctt cagggtcaaa ctctgaccac 111900
agacatttct cccctgacta ggagttccct ggatcaaaat tgggagcttg caacacatcg 111960
ttctctccct tgatggtttt tgtcagtgtc tatccagagc tgaagtgtaa tatatatgtt 112020
actgtagctg agaaattaaa tttcaggatt ctgatttcat aatgacaacc attcctcttt 112080
tctctccctt ctgtaaatct aagattctat aaacggtgtt gacttaatgt gacaattggc 112140
agtagttcag gtctgctttg taaataccct tgtgtctatt gtaaaatctc acaaaggctt 112200
gttgcctttt ttgtggggtt agaacaagaa aaagccacat ggaaaaaaaa tttctttttt 112260 gttttttttgt ttgcttgttt ttttgagaca gagtttcact ctgtcgccca ggctggagtg 112320
cagtggtgcg atctccgccc actgcaagct ccacctcccg ggttcatgct attctcctgt 112380

```
ctcagcctcc caagtagctg ggactgcagg tgcccgccac cacacctggc taattttttt 112440
gtatttttag tagagacggg gtttcaccgt gttagccagg atggtctcaa tctcctgacc 112500
tcgtcatctg cctgcctcgg cctcccaaag tgctgagatt acaggcgtga gccaccgtgc 112560
ccggccagaa aaaaacattt ctaagtatgt ggcagatact gaattattgc ttaatgtcct 112620
ttgattcatt tgtttaattt ctttaatgga ttagtacaga aaacaaagtt ctcttccttg 112680
aaaaactggt aagttttctt tgtcagataa ggagagttaa ataacccatg acatttccct 112740
ttttgcctcg gcttccagga agctcaaagt taaatgtaat gatcactctt gtaattatca 112800
gtgttgatgc ccttcccttc ttctaatgtt actctttaca ttttcctgct ttattattgt 112860
gtgtgttttc taattctaag ctgttcccac tcctttctga aagcaggcaa atcttctaag 112920
ccttatccac tgaaaagtta tgaataaaaa atgatcgtca agcctacagg tgctgaggct 112980
actccagagg ctgaggccag aggaccactt gagcccagga atttgagacc tgggctgggc 113040
agcatagcaa gactctatct ccattaaaac tatttttttt tatttaaaaa ataatccgca 113100
aagaaggagt ttatgtggga ttccttaaaa tcggagggtg gcatgaattg attcaaagac 113160
ttgtgcagag ggcgacagtg actccttgag aagcagtgtg agaaagcctg tcccacctcc 113220
ttccgcagct ccagcctggg ctgaggcact gtcacagtgt ctccttgctg gcaggagaga 113280
atttcaacat tcaccaaaaa gtagtattgt ttttattagg tttatgaggc tgtagccttg 113340
aggacagccc aggacaactt tgttgtcaca tagatagcct gtggctacaa actctgagat 113400
ctagattctt ctgcggctgc ttctgacctg agaaagttgc ggaacctcag cgagcctcac 113460
atggcctcct tgtccttaac gtggggacgg tgggcaagaa aggtgatgtg gcactagaga 113520
tttatccatc tctaaaggag gagtggattg tacattgaaa caccagagaa ggaattacaa 113580
aggaagaatt tgagtatcta aaaatgtagg tcaggcgctc ctgtgttgat tgcagggcta 113640
ttcacaatag ccaagatttg gaagcaaccc aagtgtccat caacagacaa atggataaag 113700
aaaatgtggt gcatatacac aatggaatac tattcagcca tgaaaaagaa tgagaatctg 113760
tcatttgaaa caacatggat ggaactggag gacattatgt taagtgaaat aagccagaca 113820
gaaggacaga cttcacatgt tctcacacat ttgtgggagc taaaaattaa actcatggag 113880
atagagagta gaaggatggt taccagaggc tgaggagggt ggaggggagc agggagaaag 113940
tagggatggt taatgggtac aaaaacgtag ttagcatgca tagatctagt attggatagc 114000
acagcagggt gacgacagcc aacagtaatt tatagtacat ttaaaaacaa ctaaaagagt 114060
gtaactggac tggctaacat ggtgaaaccc cgtctctact aaaaatacaa aaattagctg 114120
ggcacggtgg ctcacgcctg taatcccagc actttgggag gccgaggcgg gccgatcacg 114180
aggtcaggag atcgagacca tcctagctaa catggtgaaa ccccgtctct actacaaata 114240
caaaaaaaag aaaaaattag ccgggcatgg tggtgggcgc ctgtagtccc agctactcgg 114300
gaggctgagg caggagaatg gcgtgaaccc gggaggcgga gcttgcagtg agccgagatc 114360
gcgccactgc actccagcct gggcgacaag gcaagattct atctcaaaaa aataaaaata 114420
aaataaaata aaataataaa ataaaataaa ataaaataaa ataaaataaa taaaataaaa 114480
tgtataattg gaatgtttat aacacaagaa atgataaatg cttgaggtga tagatacccc 114540
attcaccgtg atgtgattat tgcacaatgt atgtctgtat ctaaatatct catgtacccc 114600
acaagtatat acacctacta tgtacccata taaatttaaa attaaaaaat tataaaacaa 114660
aaataaataa gtaaattaaa atgtaggctg gacaccgtgg ttcacgcctg taatcccagt 114720
```

gctttgtgag gctgaggtga gagaatcact tgagcccagg agtttgagac cggcctgggt 114780
gacatagcga gaccccatca tcacaaagaa tttttaaaaa ttagctgggc gtggtagcac 114840
ataccggtag ttccagctac ttgggagacc gaggcaggag gattgcttga gcccaggagt 114900
ttaaggctgc agtgagctac gatggcgcca ctgcattcca gcctgggtga cagagtgaga 114960
gcttgtctct attttaaaaa taataaaaag aataaataaa aataaattaa aatgtaaata 115020
tgtgcatgtt agaaaaaata cacccatcag caaaaagggg gtaaaggagc gatttcagtc 115080
ataattggag agatgcagaa taagccagca atgcagtttc ttttattttg gtcaaaaaaa 115140
ataagcaaaa caatgttgta aacacccagt gctggcagca atgtggtgag gctggctctc 115200
tcaccagggc tcacagggaa aactcatgca acccttttag aaagccatgt ggagagttgt 115260
accgagaggt tttagaatat ttataacttt gacccagaaa ttctattcta ggactctgtg 115320
ttatgaaaat aacccatcat atggaaaaag ctcctttcag aaagaggttc atgggaggct 115380
gtttgtattt tttttttctt tgcatcaaat ccagctcctg caggactgtt tgtattattg 115440
aagtacaaag tggaatcaat acaaatgttg gatagcaggg gaacaatatt cacaaaatgg 115500
aatgggacat agtattaaac atagtgcttc tgatgaccgt agaccataga caatgcttag 115560
gatatgatat cacttctttt gttgtttttt gtattttgag acgaagtctc attctgtcac 115620
ccaggctgga gttcagtggc gccatctcag ctcactgcaa cctccatctc ccgggttcaa 115680
gctattctcc ttcctcaacc tcccgagtag ctgggttgcg caccaccatg cctggctaac 115740
ttttgtattt ttagtacaga cggggtttca ccacgttggc caggctgctc ttgaactcct 115800
gacgtcaggt gatccaccag ccttgacctc ccaaagtgct aggattacag gagccactgt 115860
acccagccta ggatatgata tcacttctta gagcaagata caaaattgca tgtgcacaat 115920
aattctacca agtataggta tacaggggta gttatatata aatgagactt caaggaaata 115980
caacaaaatg caatcgtgat tgtgttaggg tggtaagaaa acggtttttg ctttgatgag 116040
ctctgttttt taaaatcgtt atattttcta ataaaaatac atagtctttt gaaggaacat 116100
aaaagattat gaagaaatga gttagatatt gattcctatt gaagattcag acaagtaaaa 116160
ttaaggggaa aaaaaacggg atgaaccaga agtcaggctg gagttccaac cccagatccg 116220
acagcccagg ctgatggggc ctccagggca gtggtttcca cccagcattc tcaaaagagc 116280
cactgaggtc tcagtgccat tttcaagatt tcggaagcgg cctgggcacg gctggtcctt 116340
cactgggatc accacttggc aattatttac acctgagacg aatgaaaacc agagtgctga 116400
gattacaggc atggtggctt acgcttgtaa tcggctttgg gaagccgagg tgggctgatt 116460
gcttgagccc aggagtttca aactatcctg gacaacatag catgacctcg tctctacaaa 116520
aaatacaaaa aatttgccag gtgtggtggc atgtgcctgt ggtcccagct acttgggagg 116580
ctgaagtagg agaatcccct gagccctggg aagtcgaggc tgcactgagc cgtgatggtg 116640
tcactgcact ccagcctggg tgacaaagtg agaccctatc tcacaaagaa aaaaaacaaa 116700
acaaaaaacc caaagcacac tgtttccact gtttccagag ttcctgagag gaaaggtcac 116760
cgggtgagga agacgttctc actgatctgg cagagaaaat gtccagtttt tccaactccc 116820
taaaccatgg ttttctattt catagttctt aggcaaattg gtaaaaatca tttctcatca 116880
aaacgctgat attttcacac ctccctggtg tctgcagaaa gaaccttcca gaaatgcagt 116940
cgtgggagac ccatccaggc cacccctgct tatggaagag ctgagaaaaa gccccacggg 117000
agcatttgct cagcttccgt tacgcaccta gtggcattgt gggtgggaga gggctggtgg 117060
gtggatggaa ggagaaggca cagccccccc ttgcagggac agagccctcg tacagaaggg 117120

```
acaccccaca tttgtcttcc ccacaaagcg gcctgtgtcc tgcctacggg gtcagggctt 117180
ctcaaacctg gctgtgtgtc agaatcacca ggggaacttt tcaaaactag agagactgaa 117240
gccagactcc tagattctaa ttctaggtca gggctagggg ctgagattgt aaaaatccac 117300
aggtgattct gatgcccggc aggcttgaga acagccgcag ggagttctct gggaatgtgc 117360
cggtgggtct agccaggtgt gagtggagat gccggggaac ttcctattac tcactcgtca 117420
gtgtggccga acacattttt cacttgacct caggctggtg aacgctcccc tctggggttc 117480
aggcctcacg atgccatcct tttgtgaagt gaggacctgc aatcccagct tcgtaaagcc 117540
cgctggaaat cactcacact tctgggatgc cttcagagca gccctctatc ccttcagctc 117600
ccctgggatg tgactcgacc tcccgtcact ccccagactg cctctgccaa gtccgaaagt 117660
ggaggcatcc ttgcgagcaa gtaggcgggt ccagggtggc gcatgtcact catcgaaagt 117720
ggaggcgtcc ttgcgagcaa gcaggcgggt ccagggtggc gtgtcactca tccttttttc 117780
tggctaccaa aggtgcagat aattaataag aagctggatc ttagcaacgt ccagtccaag 117840
tgtggctcaa aggataatat caaacacgtc ccgggaggcg gcagtgtgag taccttcaca 117900
cgtcccatgc gccgtgctgt ggcttgaatt attaggaagt ggtgtgagtg cgtacacttg 117960
cgagacactg catagaataa atccttcttg ggctctcagg atctggctgc gacctctggg 118020
tgaatgtagc ccggctcccc acattccccc acacggtcca ctgttcccag aagccccttc 118080
ctcatattct aggagggggt gtcccagcat ttctgggtcc cccagcctgc gcaggctgtg 118140
tggacagaat agggcagatg acggaccctc tctccggacc ctgcctggga agctgagaat 118200
acccatcaaa gtctccttcc actcatgccc agccctgtcc ccaggagccc catagcccat 118260
tggaagttgg gctgaaggtg gtggcacctg agactgggct gccgcctcct cccccgacac 118320
ctgggcaggt tgacgttgag tggctccact gtggacaggt gacccgtttg ttctgatgag 118380
cggacaccaa ggtcttactg tcctgctcag ctgctgctcc tacacgttca aggcaggagc 118440
cgattcctaa gcctccagct tatgcttagc ctgcgccacc ctctggcaga gactccagat 118500
gcaaagagcc aaaccaaagt gcgacaggtc cctctgccca gcgttgaggt gtggcagaga 118560
aatgctgctt ttggcccttt tagatttggc tgcctcttgc caggagtggt ggctcgtgcc 118620
tgtaattcca gcactttggg agactaaggc gggaggttcg cttgagccca ggagttcaag 118680
accagcctgg gcaacaatga gacccctgtg tctacaaaaa gaattaaaat tagccaggtg 118740
tggtggcacg cacctgtagt cccagctact tgggaggctg aggtgggagg attgcctgag 118800
tccgggaggc ggaagttgca aggagccatg atcgcgccac tgcacttcaa cctaggcaac 118860
agagtgagac tttgtctcaa aaaacaatca tataataatt ttaaaataaa tagatttggc 118920
ttcctctaaa tgtccccggg gactccgtgc atcttctgtg gagtgtctcc gtgagattcg 118980
ggactcagat cctcaagtgc aactgaccca cccgataagc tgaggcttca tcatcccctg 119040
gccggtctat gtcgactggg cacccgaggc tcctctccca ccagctctct tggtcagctg 119100
aaagcaaact gttaacaccc tggggagctg gacgtatgag acccttgggg tgggaggcgt 119160
tgatttttga gagcaatcac ctggccctgg ctggcagtac cgggacactg ctgtggctcc 119220
ggggtgggct gtctccagaa aatgcctggc ctgaggcagc cacccgcatc cagcccagag 119280
ggtttattct tgcaatgtgc tgctgcttcc tgccctgagc acctggatcc cggcttctgc 119340
cctgaggccc cttgagtccc acaggtagca agcgcttgcc ctgcggctgc tgcatggggc 119400
taactaacgc ttcctcacca gtgtctgcta agtgtctcct ctgtctccca cgccctgctc 119460
```

```
tcctgtcccc ccagtttgtc tgctgtgagg ggacagaaga ggtgtgtgcc gcccccaccc 119520

ctgcccgggc ccttgttcct gggattgctg ttttcagctg tttgagcttt gatcctggtt 119580

ctctggcttc ctcaaagtga gctcggccag aggaggaagg ccatgtgctt tctggttgaa 119640

gtcaagtctg gtgccctggt ggaggctgtg ctgctgaggc ggagctgggg agagagtgca 119700

cacgggctgc gtggccaacc cctctgggta gctgatgccc aaagacgctg cagtgcccag 119760

gacatctggg acctccctgg ggcccgcccg tgtgtcccgc gctgtgttca tctgcgggct 119820

agcctgtgac ccgcgctgtg ctcgtctgcg ggctagcctg tgtcccgcgc tctgcttgtc 119880

tgcggtctag cctgtgacct ggcagagagc caccagatgt cccgggctga gcactgccct 119940

ctgagcacct tcacaggaag cccttctcct ggtgagaaga gatgccagcc cctggcatct 120000

gggggcactg gatccctggc ctgagcccta gcctctcccc agcctggggg ccccttccca 120060

gcaggctggc cctgctcctt ctctacctgg gacccttctg cctcctggct ggaccctgga 120120

agctctgcag ggcctgctgt cccccctccct gccctccagg tatcctgacc accggccctg 120180

gctcccactg ccatccactc ctctcctttc tggccgttcc ctggtccctg tcccagcccc 120240

cctccccctc tcacgagtta cctcacccag gccagaggga agagggaagg aggccctggt 120300

cataccagca cgtcctccca cctccctcgg ccctggtcca ccccctcagt gctggcctca 120360

gagcacagct ctctccaagc caggccgcgc gccatccatc ctccctgtcc cccaacgtcc 120420

ttgccacaga tcatgtccgc cctgacacac atgggtctca gccatctctg ccccagttaa 120480

ctccccatcc ataaagagca catgccagcc gacaccaaaa taattcggga tggttccagt 120540

ttagacctaa gtggaaggag aaaccaccac ctgccctgca ccttgttttt tggtgacctt 120600

gataaaccat cttcagccat gaagccagct gtctcccagg aagctccagg gcggtgcttc 120660

ctcgggagct gactgatagg tgggaggtgg ctgcccccctt gcaccctcag gtgaccccac 120720

acaaggccac tgctggaggc cctggggact ccaggaatgt caatcagtga cctgcccccc 120780

aggccccaca cagccatggc tgcatagagg cctgcctcca agggacctgt ctgtctgcca 120840

ctgtggagtc cctacagcgt gccccccaca ggggagctgg ttctttgact gagatcagct 120900

ggcagctcag ggtcatcatt cccagaggga gcggtgccct ggaggccaca ggcctcctca 120960

tgtgtgtctg cgtccgctcg agcttactga gacactaaat ctgttggttt ctgctgtgcc 121020

acctacccac cctgttggtg ttgctttgtt cctattgcta aagacaggaa tgtccaggac 121080

actgagtgtg caggtgcctg ctggttctca cgtccgagct gctgaactcc gctgggtcct 121140

gcttactgat ggtctttgct ctagtgcttt ccagggtccg tggaagcttt tcctggaata 121200

aagcccacgc atcgaccctc acagcgcctc ccctctttga ggcccagcag ataccccact 121260

cctgcctttc cagcaagatt tttcagatgc tgtgcatact catcatattg atcacttttt 121320

tcttcatgcc tgattgtgat ctgtcaattt catgtcagga aagggagtga catttttaca 121380

cttaagcgtt tgctgagcaa atgtctgggt cttgcacaat gacaatgggt ccctgttttt 121440

cccagaggct cttttgttct gcagggattg aagacactcc agtcccacag tccccagctc 121500

ccctggggca gggttggcag aatttcgaca acacattttt ccaccctgac taggatgtgc 121560

tcctcatggc agctgggaac cactgtccaa taagggcctg ggcttacaca gctgcttctc 121620

attgagttac acccttaata aaataatccc attttatcct ttttgtctct ctgtcttcct 121680

ctctctctgc ctttcctctt ctctctcctc ctctctcatc tccaggtgca aatagtctac 121740

aaaccagttg acctgagcaa ggtgacctcc aagtgtggct cattaggcaa catccatcat 121800

aaaccaggta gccctgtgga aggtgagggt tgggacggga gggtgcaggg ggtggaggag 121860
```

```
tcctggtgag gctggaactg ctccagactt cagaaggggc tggaaaggat attttaggta 121920
gacctacatc aaggaaagtg ttgagtgtga aacttgcggg agcccaggag gcgtggtggc 121980
tccagctcgc tcctgcccag gccatgctgc ccaagacaag gtgaggcggg agtgaagtga 122040
aataaggcag gcacagaaag aaagcacata ttctcggccg ggcgctgtgg ctcacgcctg 122100
taattccagc actttgggag gccaaggtgg gtggatcatg aggtcaggag attgagacca 122160
tcctggctaa cacagtgaaa ccccgtctct actaaaaata caaaaaatta gccgggcgtg 122220
gtggtgggcg cctgtagtcc cagctactcc ggaggctgag gcaggaaaat ggcgtgaacc 122280
cggaaggcgg agcttgcagt gagcggagtg agcagagatc gcgccactgc actccagcct 122340
gggcgacaga gcgagactcc gtctcaaaaa aaaaaagcac atgttctcgc ttctttgtgg 122400
gatccaggag atagagaata gaaggatggt taccagaggc tgggaagggt agtgagggga 122460
tggtgggggg atggtcaatg ggtacaaaaa aaatagaata agacctagta tttgatagtg 122520
caacagggtg actatagtca ataataattt aattgtacat ttaaaaataa ctaaaagata 122580
gccgggtgca gtggcttacg tctgtaatcc cagtactttg ggaggctgag gtgggcgttt 122640
gagaccagcc tggccaacat ggtgaaaccc catctctact aaaaatacaa aaattagcca 122700
ggcatggtgg cgggcgcctg taatcccagc tactcgggag gctgaggcag gagaatcact 122760
tgaacctggg aggcagaggt tgcagtgagc cgagatcttg ccactgcact ccagcctggg 122820
tgacagtgaa actccgtctc aaaaataaaa ataaaaatac agctgggcac ggtggctcac 122880
gcctgtaatc ccagcacttt gggaggccga ggcgagcgga tcacaaggtc aggagatata 122940
gaccatcctg gctaacacgg tgaaacccgg tctctactaa aaatacaaaa aattagccag 123000
gcgtggtggc aggtgcctat agtcccagct actcacaagg ctgaggcagg agaatggcat 123060
gaacctggga ggcggagctt gcagtgagcc gagattgtgc cactgcactc cagcctgggc 123120
gagagagtga gactccgtct caaaacaaaa acaaaaacaa aaacaaaaac aaacacacaa 123180
caaaaaccta aaagaatata aatggattgt ttgtaacaca aaggacaaat gtttgagggg 123240
atggataccc cattttccat gatgtgatta ttatacattg tgtgtctgta tcaaaacatc 123300
tcatgagccc cataaatata tacacctaac tatgtaccca caaaaattaa aaaaatatat 123360
tttttaaggt gaagagggag gcgagatgct ggccttaacc cctaacccgt tgttctccct 123420
gcaagctgtc cacagggcct ctcagactcg aggttcagct atatggatgc atgagcttgg 123480
tccccagcca acatgggaga cacttcacca tcggcagcag ctacagcaca ggaaccctgg 123540
gtcactgcca tgtcccctct gtgactttgt ttaaacagaa aatgatgctc tgggccggct 123600
gtggtggccc acacctataa tcccagcacc ttgggaggcg ggggtgggca gattgcctga 123660
ggtcaggagt tggagatcag cctggccgac atggcgaaac cccatgtcta ctaaaaatac 123720
aaaaactagc caggcatggt ggcacatgcc tgtaatccca gctacttggg aggctgaagc 123780
aggagaatca cttgaaccca ggaggcagag gctgagtgag ccaagatcgt gccaatgcac 123840
tccagcttgg gtgagggagt gagactccgt ctcaaaaaaa aaaaaaaaga aagaaaaaga 123900
aaagaaagtg atcctactgg aaccatgctt actcccctcc ccacctcaca ctgtgtagaa 123960
attagtgctg tcggccaggc gcggtggctc atgcctgtaa tcgcagcact ttgggaggcc 124020
aaggcaggcg gatcacgagg tcaggagatc aagaccatcc tggctaacac agtgaaaccc 124080
tgtctctact aaaaatacaa aaaattagcc gggcatggtg gcaggcacct gtagtcccaa 124140
ctacttggga ggctgaggca ggagaatggc atgaacctgg gaggcggagc ttgcagtgag 124200
```

ccaagatcgc gccactgcat accagcctag gtgacagagt gagactcagc aaaaaaagaa 124260
agaaagaaag aaagaaatca gtgctgtcta tacttctttc tgcagtgatg gaaatattct 124320
gtatctgtgc tgtccagtat agtagccact agctacatgt ggcacttgaa acatggctgg 124380
tacagttgag gaagagtggc tgccatatcg gacgacacag ctatagattc tgtcacccca 124440
ccccgagagt ccagagcggg gacttctgcc ttaggcccta ttcagggctg atttttactt 124500
gaacccttac tgtgggaaga gaaggccatg agaagttcag tctagaatgt gactccttat 124560
tttctggctc ccttggacac tttgtgggat ttagtctccc tgtggaaagt attccacaag 124620
tggtgccact accccagctg tgagagcagc tgggagctgc ttttgtcatc tttccctgga 124680
aagtcctgtg ggctgtctct tcctcatgcc ttgtcccatg cttgggcatg gtgtcaagcg 124740
tcaggaggga gaaagggtcc ttatttattt atttagagag ggacccttct tctgttccca 124800
ggctggagtg cagtggtgcg atctcggctc actgcaacct ccgcctcctg ggttcaagtg 124860
attctcctgc ctcagcctcc tgagtagctg agattacagg cacatgccaa catgcccggc 124920
taattttttt tttttttttt tttttttttt tttttttttt tttgagatgg agttgtactc 124980
tcattgccca ggctggaatg taatggcaca atctcggctc actgcaacct ccacctcctg 125040
gattcaagca attctcctgt ctcagcttcc caagtagctg ggattacagg tgcccgccac 125100
catgctcaac taatttttgt attttttttt tagtagagac gaggtttcac catgttggtc 125160
agactggtct caaactcctg acctcaggtg atccacctgc ctcggcctcc caaagtgcta 125220
ggattacagg catgagccac cacgcccggc ctgaaagggt tcttatttag tgtgcatttt 125280
gacattcaat ttaattccaa ggtcttgtgg ggtcatggtt tacaggatgt tgatatagaa 125340
aagacttcac ttaatgggcc gggcgcagtg gctcatgcct gtaatcccag cactttggga 125400
ggccgaggca ggcagatcag gaggtcagga gattgagacc atcctggcta acacagtgaa 125460
accccatctc tactgaaaat acaaaaaatt agctgggcgt ggtggcaggc acctgtagtc 125520
ccagccactc ggttggctga ggcaggagaa tggcatgaac ccgggaggcg gagcttgcag 125580
tgagcagaga ccatgccact gcactccagc ctgggcgaca gagcaagact ctgtctcaag 125640
aaaaaaaaaa aaaaacagac tttacttact ggaagccaac caatgtatat ttagagtaat 125700
ttttcctggg ctgagctgtc atttactttt gcagtatctc aagaagaaga gtttacagtg 125760
taaatatttg atgcacactt tgattatata gatgaagcaa actattttca agagctttgc 125820
aaggacttac ttgtatccaa acaccattct aaaaggagtc ttacctactt ctaaaggctg 125880
gtctctactt ggaaccactt gcttggccct ggttcaagtc ctgctgcaaa cctggaagtc 125940
ctgtcattgt cttcttccct ccagagcagt ggcacccaat ctaatttttg ctgtgcccca 126000
gcagcccctg gcactttgcc ctgtagactg cagacctcat gtaatgtatg ttaagtccac 126060
agaaccacag aagatgatgg caagatgctc ttgtgtgtgt tgtgttctag gaggtggcca 126120
ggtggaagta aaatctgaga agcttgactt caaggacaga gtccagtcga agattgggtc 126180
cctggacaat atcacccacg tccctggcgg aggaaataaa aaggtaaagg gggtagggtg 126240
ggttggatgc tgcccttggg tatatgggca ttaatcaagt tgagtggaca aaggctggtc 126300
cagttcccag aggaggaaaa cagaggcttc tgtgttgact ggctggatgt gggccctcag 126360
cagcatccag tgggtctcca ctgcctgtct caatcacctg gagctttagc acgtttcaca 126420
cctgggcccc aacctggaga ggctgaccaa tgggtctcag gggcagctcg gttgctggag 126480
tttttgtttt tatttatttt tatgtattta aggcagggtc tctgtattag tccattctca 126540
cactgctaat aaagacatac ccaagactgg gtaatttata aaggaaagag gtttaatgga 126600
ctcacagttc cacatggctg gggaggcctc aaaatcatgg cggaaggcaa aggagaagca 126660
aaggcatttc ttacatggcg acaggcaaga gagcgtgtgc aggggaactc ccatttataa 126720
aaccatcaga cctcatgaga tttattcact atcatgagaa cagcatggga aagacccgcc 126780
cccatgattc agttacctcc cactgggtcc ctcccatgac acatggaatt atgggagcta 126840
caattcaaga tgagatttgg gtggggacac agccaaacca tatcagtctc cctctgtcat 126900
ccaggctgga gtgcactggc atgatctcgg ctcactgcag cctctacctc cctgggtcag 126960
gtgatcttcc cacctcagcc tcccaggtag ctggaactac aggtacctgc cactatgcct 127020
ggctaaatat tttgtatttc ctgtggagac gaggttttgc cacgttgccc aggctggtct 127080
tgaactcctg aggtcaagca atatgcccac ctcggcctcc caaggtgctg ggattacagg 127140
tgtgagccac agtgctcggc ctaagtcact gcagttttta aagctcccag gtgattcttc 127200
agtgcagtca aaagtgagaa ctggctgggt gcggtggctc atgcctgtaa tcccagcacc 127260
ttgggaggcg aaggtgggca gatggcttga ggtcaggagt tcaagaccag cctggccaac 127320
atggtaaaac cccatctcta ctaaaaatac aaaagttagc tgggtgtggt ggtgcgtgcc 127380
tgtaatccca gctacttggg aggctgaggc atgagaattg cttgaaccca ggggacagag 127440
gttgtagtga gccgagatcg tgccactgca ctccagcctg ggcaacagag tgagattcca 127500
tctcacaaaa aaaaaaaaaa gcgagaacca ctgtcctagg ccctgatgtt tgcaggcaac 127560
taaaaaagga agtggacatc cccagtcagc tgtggcgcac caagaacaag tcatgggaac 127620
ataacctaat tttctaaatg ggttactagg cacttagagc aaaacaatga tgccgaaatc 127680
ctgatttcag caaagcctct gcctgcctgt cttggaagta tccacatgag gctgctgggg 127740
ccttggtgtc cccagcagtt tctagtctct aggtcttgct gtgggtgtct gtgcagtgag 127800
ggtgtgtgtg gcgctgggtg agctctgtct aggcctggca caggatgcgg tctggtagct 127860
gctgcttctc ttctgcagaa gcgcagccaa gcaccctctg gggtttcagg cccacaccca 127920
gcctgaagtt ctgggagtgg ctcactttcc aaccttcagg gtctcccagc agctgactgg 127980
ggagtggtgg agggaaaagg gattgtatta gtccgttttc acgccgctga tgaagacata 128040
cccgatactg ggcagtctaa aagatagagg tctgatggac tcacagttcc acgtgactgg 128100
ggaggcctga caatcatggt ggaaggtgaa aggcttgtct cacacggtgg cagacaagag 128160
aaaagagctt gtgcagggga actccccttt ataaaaccat cagatctcgg gagacttatt 128220
cactatcatg agaacagcac gggaaagacc ctcctctatg attcaattac ctcccaccag 128280
gtccctccca caacatgtag gaattgtggg aactacaatt caagatgaca tttgggtggg 128340
gacacagcca aaccatatca gggcgtccca gaaagggtat agggtctgag acccaagtca 128400
gcatgagaaa gtatgcttct catggtggcc cagttgggtg gaagtggcag ccgggccgtc 128460
tttccaccag gccactcaag tagcagctga gagacccctg ccctggccag tccccgccct 128520
cccctcttgc cactgcctct ggttctgaac agatgggcac cctcatcttg tatttgtgat 128580
taatgtctaa caatgtagtt ttgtgagaag ggtttgctga tacagccttg ctgcagatgc 128640
tgcgaactgt ggcctggggc agaccttacc tccagacacg ccctgaggca ggggagggca 128700
ctggcccgta gctggccgag agctctcggg ttgcgcgaca gggatacttt tcagcggctg 128760
ggtcgctatc caaagtgaga aaacgaggag ggaccaggag gctgtccgcc tcaagagatg 128820
tgggggccag gtccagttat ctggggaagc agtaagcttc tctgctgttt ctaaccccag 128880
gcctcccctg gtctaaggca gggcctccca gcctcggggc actttaaaga tatctgggcc 128940

```
tggccccatc cccacagtct gactgagtgg gtctggatag ggcctgagca ttggtgattt 129000
cctgggtgaa aggaggcccc tcacagtctc tggaagcttc tctgtgttag gaaaagctct 129060
gggcttgact ctgctttgaa agtcaagatc cgcaaatcct ctcagcctca gtttctcctt 129120
cagcaagatg aaatggaaat gctgtaccta cgtcccgggg tggttgtgag acccaaaaaa 129180
gacaatgttc tggaaggttc ctggtgcgtt gcagtcctct aagaacctga gttagagcca 129240
cgctgagtct cagcttcttg gctccttctg tttcaaactc gtccatgtga tagctcagga 129300
agggtaggca gggccctgcc ccctactcag aaaacaccat cctggtcctg gggatccccg 129360
cagcattagt cccctgtttt cccagtgtat tgagaaaaat tgctaacaag cagtggggca 129420
caccaccagc ctcctgggtt cctttcagtt tggggatttt tggacattcc caggaatgtc 129480
ttaaaaaaca cttcaaaaaa cattaacata aatattttta tcaaagcctg tattaaatgg 129540
tctttcaaga aaatacagta acaggtcagg catggtggct catgcctgta accccagcac 129600
tttgggaggc caaggcaggc agatcacctg aaatcaggag ttcaagacca acctggccaa 129660
cacagccaaa tcccatctct acaaaaaata caaaaattag ctgggtgtgg tggcacacac 129720
ctgtagtccc agctacttgg gaggccgagg caggagaatt gcttgatccc ggaggcggag 129780
gttgcagtga gccgagatcg tgccactgca ctccagcgtg ggtgacaagg tgaatctttg 129840
tctcaaaaaa aaaaaaaaaa aaaagataaa atacagtata cagtaataga gaacaatcct 129900
tttttcaaag tagtgacccc aaatgaacaa aatatgcatc tagcttaaat gcgaacctgg 129960
ttttctctac gcccattcaa gcccctgcaa taggggccct tcaccccgca tccatggact 130020
cctaaaatta tatggaaaat ggctgtgtgt gagtgtggat ggacatgtgc acacatattt 130080
ttggctttac cagatgctca aagagcctag gacccaaaaa gggctgagaa tgaccgtgtc 130140
ggccacttca gggtcatcag gaattgctgt gcactgctca cttctccagt gaacactttc 130200
tgcttctgtg tttcctggta tcctttggga ctcctggcta ggtcatgtgt ttctctactt 130260
tcaaaagggc ttcagccagg cacgatggca tgagcctgta gtcccagttg ctctggaggt 130320
taaggtggga agattgcttg agcccaggaa tttgaggcca gcctgggcaa gtagataggt 130380
agatgattga tagatagata gatagataaa tagatggata gataagtcgc tagacagtca 130440
tccatccacc catccacaca taaaaaggcc tttgtcatgt catgttttgt ggcccacctg 130500
ccagtgttgc ccacagttgc tgcccctcca aactcatcag tcactggcaa acaggaggaa 130560
tgtgtggctc atgtctgggc atcagtggct gtgggagaca tccttgatct tctccagctt 130620
ctccttccac attttccttt gcaatctggc aatatctatt aaaataaaat gtgcatgcct 130680
tttgacctaa gagcttcact tctaggaccc acttacacgt gtgtgacatg atgttcatac 130740
gggtttattt atctgaggtt gttcatacac accattgcct gtaatcacta aaggcgggag 130800
cagcctacac atccatccac agaggagtag atgccttttg gtacatccgt ggcgacggaa 130860
tactaagcag cctgtgtatc tatacactca cacgtgtttg tttatgtgtg gaatatctct 130920
ggagggtaca caagaaactt aaaatgatca ctgtctctgg ggagggtacc tgggtgcctg 130980
ggaggcaggt cagggaagga gtgggcacag gtattaccaa ttggaagaca ataaaaacaa 131040
cagctcctgg ccaggcgcag tggctcacgc ctgtaatggc agcactctga gaggctgagg 131100
cgggcagatt gcttgcgtcc aggagttcaa gaccagcctg ggcaacatag caaaaccccg 131160
tttctattaa aaatacaaaa aattagccag gtgtggtggc atgcacctgt aatcccagct 131220
actcgggagg ctgaggtggg agaatcacct gagcctggga ggtcaaggct gcagtgaggt 131280
gagattgtgc caccgcactc tagcctgggc gatagagcaa gaccctgtct caaaaacaaa 131340
```

caaaaaacag tccctggcac tctgggccag gcctggcagg gcagttggca gggctggtct 131400
ttctctggca cttcatctca ccctccctcc cttcctcttc ttgcagattg aaacccacaa 131460
gctgaccttc cgcgagaacg ccaaagccaa gacagaccac ggggcggaga tcgtgtacaa 131520
gtcgccagtg gtgtctgggg acacgtctcc acggcatctc agcaatgtct cctccaccgg 131580
cagcatcgac atggtagact cgccccagct cgccacgcta gctgacgagg tgtctgcctc 131640
cctggccaag cagggtttgt gatcaggccc ctggggcggt caataattgt ggagaggaga 131700
gaatgagaga gtgtggaaaa aaaaagaata atgacccggc cccgccctc tgcccccagc 131760
tgctcctcgc agttcggtta attggttaat cacttaacct gcttttgtca ctcggctttg 131820
gctcgggact tcaaaatcag tgatgggagt aagagcaaat ttcatctttc caaattgatg 131880
ggtgggctag taataaaata tttaaaaaaa aacattcaaa aacatggcca catccaacat 131940
ttcctcaggc aattcctttt gattcttttt tcttcccct ccatgtagaa gagggagaag 132000
gagaggctct gaaagctgct tctgggggat ttcaagggac tgggggtgcc aaccacctct 132060
ggccctgttg tgggggtgtc acagaggcag tggcagcaac aaaggatttg aaacttggtg 132120
tgttcgtgga gccacaggca gacgatgtca accttgtgtg agtgtgacgg gggttggggt 132180
ggggcgggag gccacggggg aggccgaggc aggggctggg cagaggggag aggaagcaca 132240
agaagtggga gtgggagagg aagccacgtg ctggagagta gacatccccc tccttgccgc 132300
tgggagagcc aaggcctatg ccacctgcag cgtctgagcg gccgcctgtc cttggtggcc 132360
gggggtgggg gcctgctgtg ggtcagtgtg ccaccctctg cagggcagcc tgtgggagaa 132420
gggacagcgg gtaaaaagag aaggcaagct ggcaggaggg tggcacttcg tggatgacct 132480
ccttagaaaa gactgacctt gatgtcttga gagcgctggc ctcttcctcc ctccctgcag 132540
ggtagggggc ctgagttgag ggcttccct ctgctccaca gaaaccctgt tttattgagt 132600
tctgaaggtt ggaactgctg ccatgatttt ggccactttg cagacctggg actttagggc 132660
taaccagttc tctttgtaag gacttgtgcc tcttgggaga cgtccacccg tttccaagcc 132720
tgggccactg gcatctctgg agtgtgtggg ggtctgggag gcaggtcccg agcccctgt 132780
ccttcccacg gccactgcag tcacccctgt ctgcgccgct gtgctgttgt ctgccgtgag 132840
agcccaatca ctgcctatac ccctcatcac acgtcacaat gtcccgaatt cccagcctca 132900
ccaccccttc tcagtaatga ccctggttgg ttgcaggagg tacctactcc atactgaggg 132960
tgaaattaag ggaaggcaaa gtccaggcac aagagtggga ccccagcctc tcactctcag 133020
ttccactcat ccaactggga ccctcaccac gaatctcatg atctgattcg gttccctgtc 133080
tcctcctccc gtcacagatg tgagccaggg cactgctcag ctgtgaccct aggtgtttct 133140
gccttgttga catggagaga gcccttttccc ctgagaaggc ctggcccctt cctgtgctga 133200
gcccacagca gcaggctggg tgtcttggtt gtcagtggtg gcaccaggat ggaagggcaa 133260
ggcacccagg gcaggcccac agtcccgctg tcccccactt gcaccctagc ttgtagctgc 133320
caacctccca gacagcccag cccgctgctc agctccacat gcatagtatc agccctccac 133380
acccgacaaa ggggaacaca ccccccttgga aatggttctt ttcccccagt cccagctgga 133440
agccatgctg tctgttctgc tggagcagct gaacatatac atagatgttg ccctgccctc 133500
cccatctgca ccctgttgag ttgtagttgg atttgtctgt ttatgcttgg attcaccaga 133560
gtgactatga tagtgaaaag aaaaaaaaaa aaaaaaaagg acgcatgtat cttgaaatgc 133620
ttgtaaagag gtttctaacc caccctcacg aggtgtctct cacccccaca ctgggactcg 133680
tgtggcctgt gtggtgccac cctgctgggg cctcccaagt tttgaaaggc tttcctcagc 133740
acctgggacc caacagagac cagcttctag cagctaagga ggccgttcag ctgtgacgaa 133800
ggcctgaagc acaggattag gactgaagcg atgatgtccc cttccctact tccccttggg 133860
gctccctgtg tcagggcaca gactaggtct tgtggctggt ctggcttgcg gcgcgaggat 133920
ggttctctct ggtcatagcc cgaagtctca tggcagtccc aaaggaggct tacaactcct 133980
gcatcacaag aaaaaggaag ccactgccag ctggggggat ctgcagctcc cagaagctcc 134040
gtgagcctca gccacccctc agactgggtt cctctccaag ctcgccctct ggaggggcag 134100
cgcagcctcc caccaagggc cctgcgacca cagcagggat tgggatgaat tgcctgtcct 134160
ggatctgctc tagaggccca agctgcctgc ctgaggaagg atgacttgac aagtcaggag 134220
acactgttcc caaagccttg accagagcac ctcagcccgc tgaccttgca caaactccat 134280
ctgctgccat gagaaaaggg aagccgcctt tgcaaaacat tgctgcctaa agaaactcag 134340
cagcctcagg cccaattctg ccacttctgg tttgggtaca gttaaaggca accctgaggg 134400
acttggcagt agaaatccag ggcctcccct ggggctggca gcttcgtgtg cagctagagc 134460
tttacctgaa aggaagtctc tgggcccaga actctccacc aagagcctcc ctgccgttcg 134520
ctgagtccca gcaattctcc taagttgaag ggatctgaga aggagaagga aatgtggggt 134580
agatttggtg gtggttagag atatgccccc ctcattactg ccaacagttt cggctgcatt 134640
tcttcacgca cctcggttcc tcttcctgaa gttcttgtgc cctgctcttc agcaccatgg 134700
gccttcttat acggaaggct ctgggatctc ccccttgtgg gggcaggctc ttggggccag 134760
cctaagatca tggtttaggg tgatcagtgc tggcagataa attgaaaagg cacgctggct 134820
tgtgatctta aatgaggaca atccccccag ggctgggcac tcctcccctc ccctcacttc 134880
tcccacctgc agagccagtg tccttgggtg ggctagatag gatatactgt atgccggctc 134940
cttcaagctg ctgactcact ttatcaatag ttccatttaa attgacttca gtggtgagac 135000
tgtatcctgt ttgctattgc ttgttgtgct atggggggag gggggaggaa tgtgtaagat 135060
agttaacatg ggcaaaggga gatcttgggg tgcagcactt aaactgcctc gtaacccttt 135120
tcatgatttc aaccacattt gctagaggga gggagcagcc acggagttag aggcccttgg 135180
ggtttctctt ttccactgac aggctttccc aggcagctgg ctagttcatt ccctccccag 135240
ccaggtgcag gcgtaggaat atggacatct ggttgctttg gcctgctgcc ctctttcagg 135300
ggtcctaagc ccacaatcat gcctccctaa gaccttggca tccttccctc taagccgttg 135360
gcacctctgt gccacctctc acactggctc cagacacaca gcctgtgctt ttggagctga 135420
gatcactcgc ttcaccctcc tcatctttgt tctccaagta aagccacgag gtcggggcga 135480
gggcagaggt gatcacctgc gtgtcccatc tacagacctg cggcttcata aaacttctga 135540
tttctcttca gctttgaaaa gggttaccct gggcactggc ctagagcctc acctcctaat 135600
agacttagcc ccatgagttt gccatgttga gcaggactat ttctggcact tgcaagtccc 135660
atgatttctt cggtaattct gagggtgggg ggagggacat gaaatcatct tagcttagct 135720
ttctgtctgt gaatgtctat atagtgtatt gtgtgtttta acaaatgatt tacactgact 135780
gttgctgtaa aagtgaattt ggaaataaag ttattactct gattaaataa ggtctccatt 135840
catggattcc aaggacaaga aagtcatata gaatgtctat tttttaagtt ctttcccacg 135900
cacccttaga taatttagct cagaacagga aatgatagta ttaataaaag ctggacatca 135960
ggattaacag ctctctctgg ggccctgaag gtgagagttc tcagacttgc tcatttgcag 136020
ttgcttcttt gtgatgctgg caaaccatcc tagtcccatt caaagggcaa tacaaagcct 136080

```
tgtggctgac ctcacgatgc agcactcagt ttgcaagacc ggcaccagtg tatgcaaacc 136140

tgagaaggtt ggggatgagg atatgggatc tttcatccct ggaaatttag tccagaggcc 136200

tggggctgga gcagaacacc aagccaatca gcttaatgaa tggcttagat tcctgctagg 136260

tttgcagagc tgccttcttt cctttggtac cttattatag attgaggagt atttctgcta 136320

aaccaagata gggataacca gatagcatct tcatagcaat gccacaaagg aaaacaaaaa 136380

caaaacagta atccatcata ttattcctta gtaactatgc caaggtcatg atactgaatc 136440

cttagattgt ttcaaaatac tacttttctt tgctcttcct gatgtgtttg ccaccgcagg 136500

cagatgttta agtaaaacag attttaactg cagctacaaa agcagcaaca ggccagcaaa 136560

agagaagtgc tatctcagag agcatggctt tcagagccac aagagacagc ctcactggct 136620

gtttcagctt gactgccatg caaagaagag agcagaggga gaaccagccc cacccactta 136680

ttcatcttgt acaaaaaaaa agcacctacc agcctaggct acatagtgag acactatctc 136740

cacaaaaaac ccacgaaaac tagctgggta tggtggcaca tgcctacagt cccagctact 136800

ggtaaggctg tggtgggagg atctcttgag gccaggaagg agatccaggc tgcagtgagc 136860

caagattgca ccactgcact ccagtctgga caatcgagca agatcccatc tcaaacaata 136920

aaaaaaaaaa gcgtgtaacc tcctcagaag aaagatgtta taatctcagg cagcaggcaa 136980

gaaccaatcc aggctctaag c                                         137001
```

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5

```
aagattgggt ccctggacaa t                                             21
```

<210> SEQ ID NO 6
<211> LENGTH: 26
<212> TYPE: DNA
<213> ORGANISM: Artificial sequence
<220> FEATURE:
<223> OTHER INFORMATION: Primer

<400> SEQUENCE: 6

```
agcttgtggg tttcaatctt tttatt                                        26
```

<210> SEQ ID NO 7
<211> LENGTH: 19
<212> TYPE: DNA
<213> ORGANISM: Artificial sequence
<220> FEATURE:
<223> OTHER INFORMATION: Probe

<400> SEQUENCE: 7
cacccacgtc cctggcgga 19

<210> SEQ ID NO 8
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 8
ccgttttctt accaccct 18

<210> SEQ ID NO 9
<211> LENGTH: 23
<212> TYPE: DNA
<213> ORGANISM: Artificial sequence
<220> FEATURE:
<223> OTHER INFORMATION: Primer

<400> SEQUENCE: 9
aggacagagt gcagtcgaag atc 23

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
aggtcagctt gtgggtttca a 21

<210> SEQ ID NO 11
<211> LENGTH: 21
<212> TYPE: DNA
<213> ORGANISM: Artificial sequence
<220> FEATURE:
<223> OTHER INFORMATION: Probe

<400> SEQUENCE: 11
cacccatgtc cctggcggag g 21

COMPOUNDS AND METHODS FOR REDUCING TAU EXPRESSION

CROSS-REFERENCE TO RELATED APPLICATIONS

This application is a continuation of U.S. application Ser. No. 15/721,366, filed Sep. 29, 2017, now U.S. Pat. No. 10,407,680, which claims priority to U.S. Provisional Appl. No. 62/450,469 filed Jan. 25, 2017 and U.S. Provisional Appl. No. 62/401,723 filed Sep. 29, 2016, the content of all of which is incorporated by reference herein in their entirety.

SEQUENCE LISTING

The present application is being filed along with a Sequence Listing in electronic format. The Sequence Listing is provided as a file entitled BIOL0285USSEQ_ST25, created on Sep. 28, 2017, which is 176 KB in size. The information in the electronic format of the sequence listing is incorporated herein by reference in its entirety.

FIELD

Provided are compounds, methods, and pharmaceutical compositions for reducing the amount or activity of Tau mRNA in a cell or animal, and in certain instances reducing the amount of Tau protein in a cell or animal. Such compounds, methods, and pharmaceutical compositions are useful to ameliorate at least one symptom of a neurodegenerative disease. Such symptoms include loss of memory, loss of motor function, and increase in the number and/or volume of neurofibrillary inclusions. Such neurodegenerative diseases include tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome.

BACKGROUND

The primary function of Tau is to bind to and stabilize microtubules, which are important structural components of the cytoskeleton involved in mitosis, cytokinesis, and vesicular transport. Tau is found in multiple tissues, but is particularly abundant in axons of neurons. In humans, there are six isoforms of Tau that are generated by alternative splicing of exons 2, 3, and 10. Splicing of exons 2 and 3 at the N-terminus of the protein leads to inclusion of zero, one, or two 29 amino acid acidic domains and is termed 0N, 1N, or 2N Tau respectively. The influence of these domains on Tau function is not fully clear, though may play a role in interactions with the plasma membrane. Inclusion of exon 10 at the C-terminus leads to inclusion of the microtubule binding domain encoded by exon 10. Since there are 3 microtubule binding domains elsewhere in Tau, this Tau isoform (with exon 10 included) is termed 4R Tau, where 'R' refers to the number of repeats of microtubule binding domains. Tau without exon 10 is termed 3R Tau. Since more microtubule binding domains (4R compared with 3R) increases the binding to microtubules, 4R Tau presumably significantly increases microtubule binding and assembly. The ratio of 3R/4R Tau is developmentally regulated, with fetal tissues expressing exclusively 3R Tau and adult human tissues expressing approximately equal levels of 3R/4R Tau. Deviations from the normal ratio of 3R/4R Tau are characteristic of neurodegenerative FTD Tauopathies. It is not known how changing the 3R/4R Tau ratio at a later stage in the adult animal will affect Tau pathogenesis.

Serine-threonine directed phosphorylation regulates the microtubule binding ability of Tau. Hyperphosphorylation promotes detachment of Tau from microtubules. Other post translational modifications of Tau have been described; however the significance of these is unclear. Phosphorylation of Tau is also developmentally regulated with higher phosphorylation in fetal tissues and much lower phosphorylation in the adult. One characteristic of neurodegenerative disorders is aberrantly increased Tau phosphorylation. The microtubule network is involved in many important processes within the cell including structural integrity needed for maintaining morphology of cells and operating transport machinery. Since binding of Tau to microtubules stabilizes microtubules, Tau is likely to be a key mediator of some of these processes and disruption of normal Tau in neurodegenerative diseases may disrupt some of these key cellular processes. One of the early indicators that Tau may be important in neurodegenerative syndromes was the recognition that Tau is a key component of neurofibrillary inclusions in Alzheimer's disease. In fact, neurofibrillary inclusions are aggregates of hyperphosphorylated Tau protein. Along with amyloid beta containing plaques, neurofibrillary inclusions are a hallmark of Alzheimer's disease and correlate significantly with cognitive impairment. 95% of Tau accumulations in AD are found in neuronal processes and is termed neuritic dystrophy. The process(es) whereby this microtubule associated protein becomes disengaged from microtubules and forms accumulations of proteins and how this relates to neuronal toxicity is not well understood.

Neuronal Tau inclusions are a pathological characteristic of not only Alzheimer's disease, but also a subset of Frontotemporal dementia (FTD), PSP, and CBD. The link between Tau and neurodegeneration was solidified by the discovery that mutations in the Tau gene cause a subset of FTD. These genetic data have also highlighted the importance of the 3R:4R ratio of Tau. Many of the Tau mutations that cause FTD lead to a change in Tau splicing which leads to preferential inclusion of exon 10, and thus to increased 4R Tau. The overall Tau levels are normal. Whether the Tau isoform change or the amino acid change or both cause neurodegeneration remains unknown. Recent data suggest that PSP may also be associated with an increased 4R:3R Tau ratio.

To help understand the influence of Tau ratios on neurodegeneration, a mouse model based on one of the splicing Tau mutations (N279K) has been generated using a minigene that includes the Tau promoter and the flanking intronic sequences of exon 10. As in humans, these mice demonstrate increased levels of 4R Tau compared with transgenics expressing WT Tau and develop behavioral and motor abnormalities as well as accumulations of aggregated Tau in the brain and spinal cord.

Tau protein has been associated with multiple diseases of the brain including Alzheimer's disease, FTD, PSP, CBD, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration and others. Tau-associated disorders such as AD are the most common cause of dementia in the elderly. AD affects an estimated 15 million people worldwide and 40% of the population above 85 years of age. AD is characterized by two pathological hallmarks: Tau neurofibrillary inclusions (NFT) and amyloid-β (Aβ) plaques.

There is currently a lack of acceptable options for treating such neurodegenerative diseases. It is therefore an object herein to provide methods for the treatment of such diseases.

SUMMARY OF THE INVENTION

Provided herein are compounds and methods for reducing the amount or activity of Tau mRNA, and in certain embodiments reducing the amount of Tau protein in a cell or animal. In certain embodiments, the animal has a neurodegenerative disease. In certain embodiments, the animal has a tauopathy, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome. In certain embodiments, compounds useful for reducing expression of Tau mRNA are oligomeric compounds. In certain embodiments, Compound No. 814907 is useful for reducing expression of Tau mRNA and/or Tau protein.

Also provided are methods useful for preventing or ameliorating at least one symptom of a neurodegenerative disease. In certain embodiments, such symptoms are loss of memory, loss of motor function, and increase in the number and/or volume of neurofibrillary inclusions. In certain embodiments, prevention or amelioration results in maintaining or improving memory, maintaining or improving motor function, and/or maintenance or reduction in the number and/or volume of neurofibrillary inclusions. In certain embodiments, such prevention or amelioration of symptoms is the decrease in the rate of progression or delay in onest of such symptoms.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "administering" means providing a pharmaceutical agent to an animal.

As used herein, "animal" means a human or non-human animal.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound or oligomeric duplex capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom is loss of memory, loss of motor function, or increase in the number and/or volume of neurofibrillary inclusions. In certain embodiments, amelioration of these symptoms results in maintaining or improving memory, maintaining or improving motor function, and/or maintenance or reduction in the number and/or volume of neurofibrillary inclusions.

As used herein, "at least one symptom of a neurodegenerative disease" includes loss of memory, loss of motor function, or increase in the number and/or volume of neurofibrillary inclusions.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more sterorandom chiral centers. In certain embodiments, the molecules are modified oligonucleotides. In certain embodiments, the molecules are compounds comprising modified oligonucleotides.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methylcytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif. Unless otherwise indicated, the sugar moieties of the nucleosides of the gap of a gapmer are unmodified 2'-deoxyfuranosyl. Thus, the term "MOE gapmer" indicates a gapmer having a sugar motif of 2'-MOE nucleosides in both wings and a gap of 2'-deoxynucleosides. Unless otherwise indicated, a MOE gapmer may comprise one or more modified internucleoside linkages and/or modified nucleobases and such modifications do not necessarily follow the gapmer pattern of the sugar modifications.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, the term "internucleoside linkage" is the covalent linkage between adjacent nucleosides in an oligonucleotide. As used herein "modified internucleoside linkage" means any internucleoside linkage other than a phosphodiester internucleoside linkage. "Phosphorothioate linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substitutent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "MOE" means methoxyethyl. "2'-MOE" means a —$OCH_2CH_2OCH_3$ group at the 2' position of a furanosyl ring.

As used herein, "motif" means the pattern of unmodified and/or modified sugar moieties, nucleobases, and/or internucleoside linkages, in an oligonucleotide.

As used herein, "mRNA" means an RNA transcript that encodes a protein and includes pre-mRNA and mature mRNA unless otherwise specified.

As used herein, "nucleobase" means an unmodified nucleobase or a modified nucleobase. As used herein an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A "5-methylcytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a continuous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

As used herein "pharmaceutical composition" means a mixture of substances suitable for administering to a subject. For example, a pharmaceutical composition may comprise an antisense compound and a sterile aqueous solution. In certain embodiments, a pharmaceutical composition shows activity in free uptake assay in certain cell lines.

As used herein, "phosphorus moiety" means a group of atoms comprising a phosphorus atom. In certain embodiments, a phosphorus moiety comprises a mono-, di-, or tri-phosphate, or phosphorothioate.

As used herein "prodrug" means a therapeutic agent in a form outside the body that is converted to a different form within an animal or cells thereof. Typically conversion of a prodrug within the animal is facilitated by the action of an enzymes (e.g., endogenous or viral enzyme) or chemicals present in cells or tissues and/or by physiologic conditions.

As used herein, "reducing or inhibiting the amount or activity" refers to a reduction or blockade of the transcriptional expression or activity relative to the transcriptional expression or activity in an untreated or control sample and does not necessarily indicate a total elimination of transcriptional expression or activity.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "Self-complementary" in reference to an oligonucleotide means an oligonucleotide that at least partially hybridizes to itself.

As used herein, "standard cell assay" means the assay described in Example 1 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to an animal. For example, a therapeutically effective amount improves a symptom of a disease.

The present disclosure provides the following non-limiting numbered embodiments:

Embodiment 1: A modified oligonucleotide according to the following formula:

(SEQ ID NO: 8)

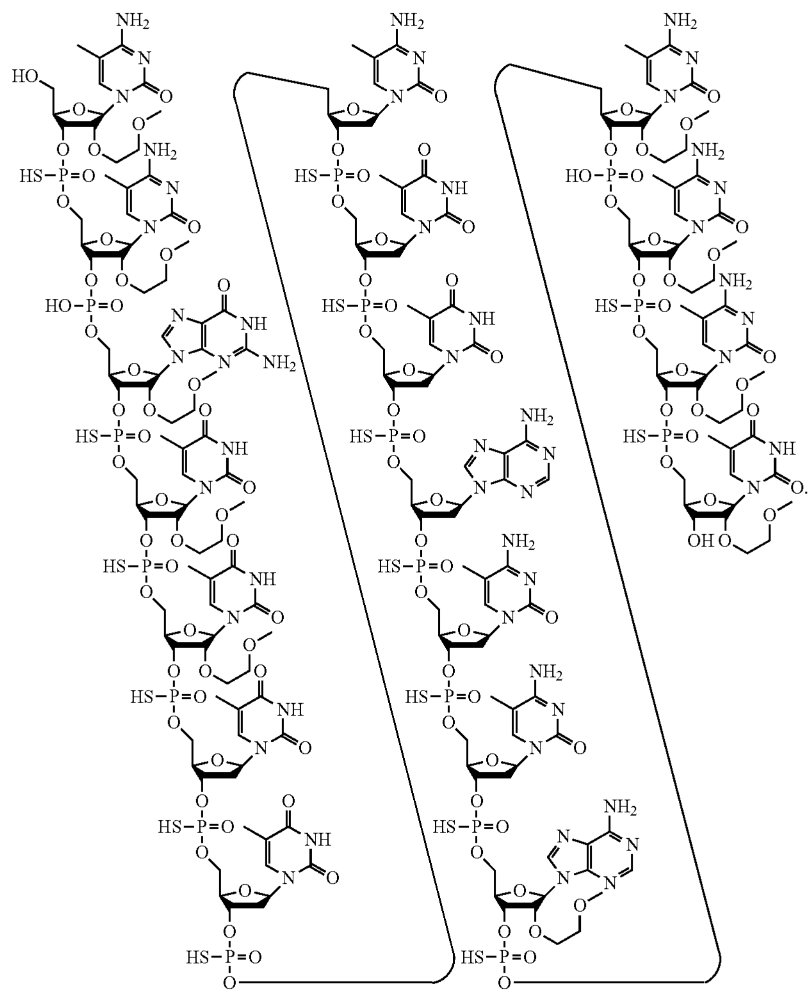

Consistent with the definitions and disclosure herein, compounds of Embodiment 1 may be made by deliberately controlling stereochemistry of any, all or none of the linkages.

Embodiment 2: An oligomeric compound comprising a modified oligonucleotide according to the following formula: mCes mCeo Ges Tes Tes Tds Tds mCds Tds Tds Ads mCds mCds Aes mCeo mCes mCes Te; wherein, A=an adenine, mC=a 5-methylcytosine, G=a guanine, T=a thymine, e=a 2'-MOE nucleoside, d=a 2'-deoxynucleoside, s=a phosphorothioate internucleoside linkage, and o=a phosphodiester internucleoside linkage.

Embodiment 3: The oligomeric compound of embodiment 2 comprising a conjugate group.

Embodiment 4: An oligomeric duplex comprising an oligomeric compound of embodiment 2 or embodiment 3.

Embodiment 5: An antisense compound comprising or consisting of a modified oligonucleotide according to embodiment 1, an oligomeric compound according to embodiment 2 or embodiment 3, or an oligomeric duplex according to embodiment 4.

Embodiment 6: A pharmaceutical composition comprising a modified oligonucleotide according to embodiment 1, an oligomeric compound according to embodiment 2 or embodiment 3, or an oligomeric duplex according to embodiment 4 or a salt thereof and a pharmaceutically acceptable carrier or diluent.

Embodiment 7: The composition of embodiment 6, wherein the salt is sodium.

Embodiment 8: A method comprising administering to an animal a pharmaceutical composition according to embodiment 6 or embodiment 7.

Embodiment 9: A method of treating a disease associated with Tau comprising administering to an individual having or at risk for developing a disease associated with Tau a therapeutically effective amount of a pharmaceutical composition according to embodiment 6 or embodiment 7; and thereby treating the disease associated with Tau.

Embodiment 10: The method of embodiment 9, wherein the disease associated with Tau is a neurodegenerative disease.

Embodiment 11: The method of embodiment 10, wherein the neurodegenerative disease is any of a tauopathy, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

Embodiment 12: The method of embodiment 10 or embodiment 11, wherein at least one symptom of the neurodegenerative disease is ameliorated.

Embodiment 13: The method of embodiment 12, wherein the symptom is any of loss of memory, loss of motor function, and increase in the number and/or volume of neurofibrillary inclusions.

Embodiment 14: A modified oligonucleotide according to the following formula:

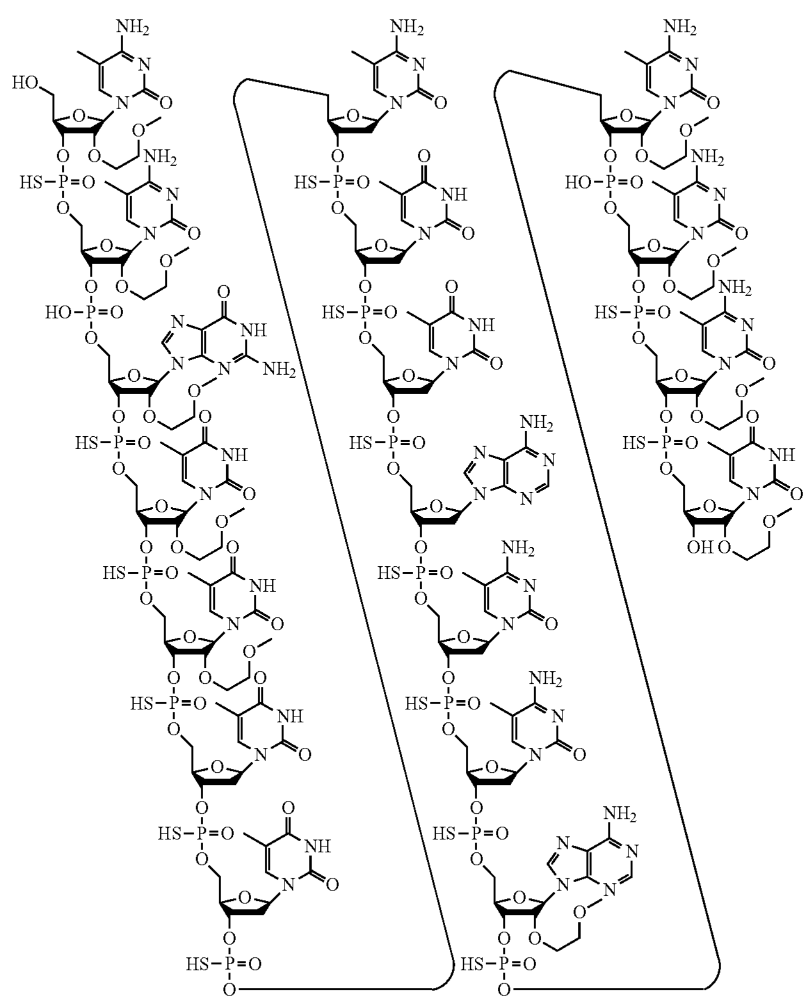

(SEQ ID NO: 8)

or a salt thereof.

Embodiment 15. The modified oligonucleotide of embodiment 14, which is a sodium salt of the formula.

Embodiment 16. A compound comprising a modified oligonucleotide, wherein the modified oligonucleotide is a gapmer consisting of a 5' wing segment, a central gap segment, and a 3' wing segment, wherein:

the 5' wing segment consists of five 2'-MOE nucleosides, the central gap segment consists of eight 2'-deoxynucleosides, and the 3' wing segment consists of five 2'-MOE nucleosides;

wherein the modified oligonucleotide has the nucleobase sequence 5'-CCGTTTTCTTACCACCCT-3' (SEQ ID NO: 8), wherein each cytosine is a 5-methylcytosine; and wherein the internucleoside linkages of the modified oligonucleotide are, from 5' to 3', sosssssssssssssoss, wherein each s is a phosphorothioate linkage and each o is a phosphodiester linkage.

Embodiment 17. A modified oligonucleotide, wherein the modified oligonucleotide is a gapmer consisting of a 5' wing segment, a central gap segment, and a 3' wing segment, wherein:

the 5' wing segment consists of five 2'-MOE nucleosides, the central gap segment consists of eight 2'-deoxynucleosides, and the 3' wing segment consists of five 2'-MOE nucleosides;

wherein the modified oligonucleotide has the nucleobase sequence 5'-CCGTTTTCTTACCACCCT-3' (SEQ ID NO: 8), wherein each cytosine is a 5-methylcytosine; and wherein the internucleoside linkages of the modified oligonucleotide are, from 5' to 3', sosssssssssssssoss, wherein each s is a phosphorothioate linkage and each o is a phosphodiester linkage.

Embodiment 18. A chirally enriched population of modified oligonucleotides of any of embodiments 14, 15 or 17 wherein the population is enriched for modified oligonucleotides comprising at least one particular phorphorothioate internucleoside linkage having a particular stereochemical configuration.

Embodiment 19. The chirally enriched population of embodiment 18, wherein the population is enriched for modified oligonucleotides comprising at least one particular phorphorothioate internucleoside linkage having the (Sp) configuration.

Embodiment 20. The chirally enriched population of embodiment 18, wherein the population is enriched for modified oligonucleotides comprising at least one particular phorphorothioate internucleoside linkage having the (Rp) configuration.

Embodiment 21. The chirally enriched population of embodiment 18, wherein the population is enriched for modified oligonucleotides having a particular, independently selected stereochemical configuration at each phosphorothioate internucleoside linkage Embodiment 22. The chirally enriched population of embodiment 21, wherein the population is enriched for modified oligonucleotides having the (Sp) configuration at each phosphorothioate internucleoside linkage.

Embodiment 23. The chirally enriched population of embodiment 21, wherein the population is enriched for modified oligonucleotides having the (Rp) configuration at each phosphorothioate internucleoside linkage.

Embodiment 24. The chirally enriched population of embodiment 21, wherein the population is enriched for modified oligonucleotides having the (Rp) configuration at one particular phosphorothioate internucleoside linkage and the (Sp) configuration at each of the remaining phosphorothioate internucleoside linkages.

Embodiment 25. The chirally enriched population of embodiment 18 or embodiment 21 wherein the population is enriched for modified oligonucleotides having at least 3 contiguous phosphorothioate internucleoside linkages in the Rp, Sp, and Sp configurations, in the 5' to 3' direction.

Embodiment 26. A chirally enriched population of modified oligonucleotides of any of embodiment 1-17, wherein all of the phosphorothioate internucleoside linkages of the modified oligonucleotide are stereorandom.

Embodiment 27. A pharmaceutical composition comprising the modified oligonucleotide of any of embodiments 14, 15, or 17 and a pharmaceutically acceptable diluent or carrier.

Embodiment 28. A pharmaceutical composition comprising the population of modified oligonucleotides of any of embodiments 18-26 and a pharmaceutically acceptable diluent or carrier.

Embodiment 29. The pharmaceutical composition of embodiment 27 or embodiment 28, wherein the pharmaceutically acceptable diluent is phosphate-buffered saline (PBS) or artificial CSF (aCSF).

Embodiment 30. The pharmaceutical composition of embodiment 27 or embodiment 28, wherein the pharmaceutical composition consists essentially of the modified oligonucleotide and phosphate-buffered saline (PBS) or artificial CSF (aCSF).

I. Certain Oligonucleotides

In certain embodiments, provided herein are oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-$OCH_3$ ("OMe" or "O-methyl"), and 2'-$O(CH_2)_2OCH_3$ ("MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, O—$C_1$-$C_{10}$ alkyl, O—$C_1$-$C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C({=}O){-}N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted non-bicyclic modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH{=}CH_2$, $OCH_2CH{=}CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C({=}O){-}N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside non-bicyclic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)—N(H)CH_3$ ("NMA").

In certain embodiments, a 2'-substituted non-bicyclic modified nucleoside comprises a sugar moiety comprising a non-bridging 2'-substituent group selected from: F, $OCH_3$, and $OCH_2CH_2OCH_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt"), 4'-$CH_2$-O—$CH_2$-2', 4'-$CH_2$—N(R)-2', 4'-CH$(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—$N(OCH_3)$-2' and analogs thereof (see, e.g., Prakash et al., U.S. Pat. No. 8,278,425), 4'-$CH_2$—O—$N(CH_3)$-2' (see, e.g., Allerson et al., U.S. Pat. No. 7,696,345 and Allerson et al., U.S. Pat. No. 8,124,745), 4'-$CH_2$—$C(H)(CH_3)$-2' (see, e.g., Zhou, et al., *J. Org. Chem.,* 2009, 74, 118-134), 4'-$CH_2$—$C(=CH_2)$-2' and analogs thereof (see e.g., Seth et al., U.S. Pat. No. 8,278,426), 4'-$C(R_aR_b)$—N(R)—O-2', 4'-$C(R_aR_b)$—O—N(R)-2', 4'-$CH_2$—O—N(R)-2', and 4'-$CH_2$—N(R)—O-2', wherein each R, $R_a$, and $R_b$, is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —$[C(R_a)(R_b)]_n$—, —$[C(R_a)(R_b)]_n$—O—, —$C(R_a)=C(R_b)$—, —$C(R_a)=N$—, —$C(=NR_a)$—, —C(=O)—, —C(=S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$, is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research,* 1997, 25(22), 4429-4443, Albaek et al., *J. Org. Chem.,* 2006, 71, 7731-7740, Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 20017, 129, 8362-8379; Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

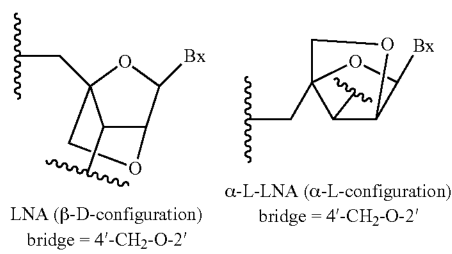

LNA (β-D-configuration) bridge = 4'-$CH_2$-O-2'

α-L-LNA (α-L-configuration) bridge = 4'-$CH_2$-O-2'

α-L-methyleneoxy (4'-$CH_2$—O-2') or α-L-LNA bicyclic nucleosides have been incorporated into oligonucleotides that showed antisense activity (Frieden et al., *Nucleic Acids Research,* 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

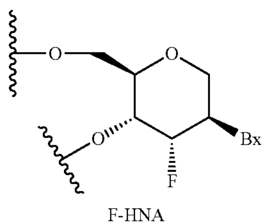

("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

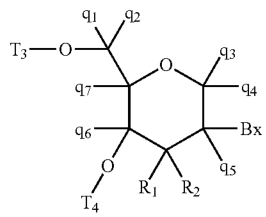

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1 q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

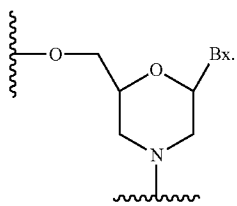

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—$CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino ($—CH_2—N(CH_3)—O—CH_2—$), thiodiester, thionocarbamate (—O—C(═O)(NH)—S—); siloxane ($—O—SiH_2—O—$); and N,N'-dimethylhydrazine ($—CH_2—N(CH_3)—N(CH_3)—$). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

($R_p$)

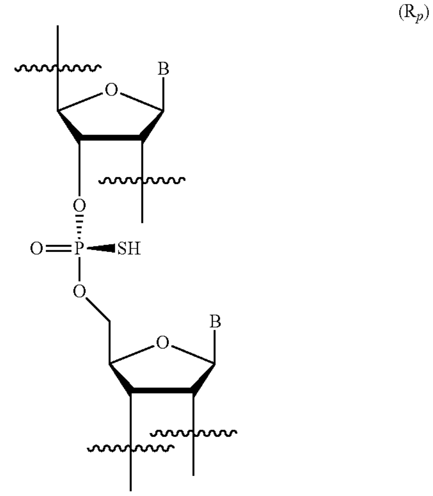

-continued

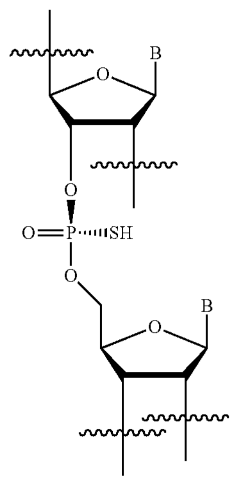

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-$CH_2$—$N(CH_3)$—O-5'), amide-3 (3'-$CH_2$—C(═O)—N(H)-5'), amide-4 (3'-$CH_2$—N(H)—C(═O)-5'), formacetal (3'-O—$CH_2$—O-5'), methoxypropyl, and thioformacetal (3'-S—$CH_2$—O—5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside.

In certain embodiments, the gap of a gapmer comprises 7-12 nucleosides. In certain embodiments, each nucleoside of the gap of a gapmer is an unmodified 2'-deoxy nucleoside.

In certain embodiments, the gapmer is a deoxy gapmer. In embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

Herein, the lengths (number of nucleosides) of the three regions of a gapmer may be provided using the notation [# of nucleosides in the 5'-wing]—[# of nucleosides in the gap]—[# of nucleosides in the 3'-wing]. Thus, a 5-8-5 gapmer consists of 5 linked nucleosides in each wing and 8 linked nucleosides in the gap. Where such nomenclature is followed by a specific modification, that modification is the modification in the wings and the gap nucleosides comprise unmodified deoxynucleosides sugars. Thus, a 5-8-5 MOE gapmer consists of 5 linked MOE modified nucleosides in the 5'-wing, 8 linked deoxynucleosides in the gap, and 5 linked MOE nucleosides in the 3'-wing. In certain embodiments, modified oligonucleotides are 5-8-5 MOE gapmers.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified.

In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines. In certain embodiments, all of the cytosine nucleobases are 5-methylcytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P═O). In certain embodiments, each internucleoside linking group of a modified oligonucleotide is a phosphorothioate internucleoside linkage (P═S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

C. Certain Lengths

It is possible to increase or decrease the length of an oligonuclotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target mRNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides D. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular sterochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

B. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a region complementary to a target nucleic acid and a second oligomeric compound having a region complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute.Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target RNA is a mature mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

A. Complementarity/Mismatches to the Target Nucleic Acid

It is possible to incroduce mismatch bases without eliminating activity. For example, Gautschi et al (J. Natl. Cancer Inst. 93:463-471, March 2001) demonstrated the ability of an oligonucleotide having 100% complementarity to the bc1-2 mRNA and having 3 mismatches to the bc1-xL mRNA to reduce the expression of both bc1-2 and bc1-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligomeric compounds comprise oligonucletoides that are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligomeric compound comprising an oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. Tau

In certain embodiments, oligomeric compounds comprise or consist of an oligonucleotide comprising a region that is complementary to a target nucleic acid, wherein the target nucleic acid is Tau. In certain embodiments, Tau nucleic acid has the sequence set forth in SEQ ID NO: 1 (GENBANK Accession No. NT_010783.14 truncated from nucleotides 2624000 to 2761000).

In certain embodiments, contacting a cell with an oligomeric compound complementary to SEQ ID NO: 1 reduces the amount of Tau mRNA, and in certain embodiments reduces the amount of Tau protein. In certain embodiments, contacting a cell in an animal with an oligomeric compound complementary to SEQ ID NO: 1 ameliroates one or more symptoms of a neurodegenerative disease. In certain embodiments, the symptom is loss of memory, loss of motor function, or increase in the number and/or volume of neurofibrillary inclusions. In certain embodiments, contacting a cell in an animal with an oligonucleotide complementary to SEQ ID NO: 1 results in maintaining or improving memory, maintaining or improving motor function, and/or maintenance or reduction in the number and/or volume of neurofibrillary inclusions.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in the central nervous system (CNS).

VI. Certain Pharmaceutical Compositions

In certain embodiments, described herein are pharmaceutical compositions comprising one or more oligomeric compounds or a salt thereof. In certain embodiments, the pharmaceutical composition comprises a pharmaceutically acceptable diluent or carrier. In certain embodiments, a pharmaceutical composition comprises a sterile saline solution and one or more oligomeric compound. In certain embodiments, a pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises one or more oligomeric compound and phosphate-buffered saline (PBS). In certain embodiments, a pharmaceutical composition consists of one or moreoligomeric compound and sterile PBS. In certain embodiments, the sterile PBS is pharmaceutical grade PBS.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal, intracerebroventricular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

VII. Certain Compounds

In certain embodiments, Compound No. 814907 is characterized as a 5-8-5 MOE gapmer, having a sequence of (from 5' to 3') CCGTTTTCTTACCACCCT (incorporated herein as SEQ ID NO: 8), wherein each of nucleosides 1-5 and 14-18 are 2'-MOE nucleosides and each of nucleosides 6-13 are 2'-deoxynucleosides, wherein the internucleoside linkages between nucleoside 2 and nucleoside 3 and nucleoside 15 to nucleoside 16 are phosphodiester internucleoside linkages and the remainder of the internucleoside linkages are phosphorothioate internucleoside linkages, and wherein each cytosine is a 5-methylcytosine.

In certain embodiments, Compound No. 814907 is characterized by the following chemical notation: mCes mCeo Ges Tes Tes Tds Tds mCds Tds Tds Ads mCds mCds Aes mCeo mCes mCes Te; wherein, A=an adenine, mC=a 5-methylcytosine, G=a guanine, T=a thymine, e=a 2'-MOE nucleoside, d=a 2'-deoxynucleoside, s=a phosphorothioate internucleoside linkage, and o=a phosphodiester internucleoside linkage.

In certain embodiments, Compound No. 814907 is characterized by the following chemical structure:

(SEQ ID NO: 8)

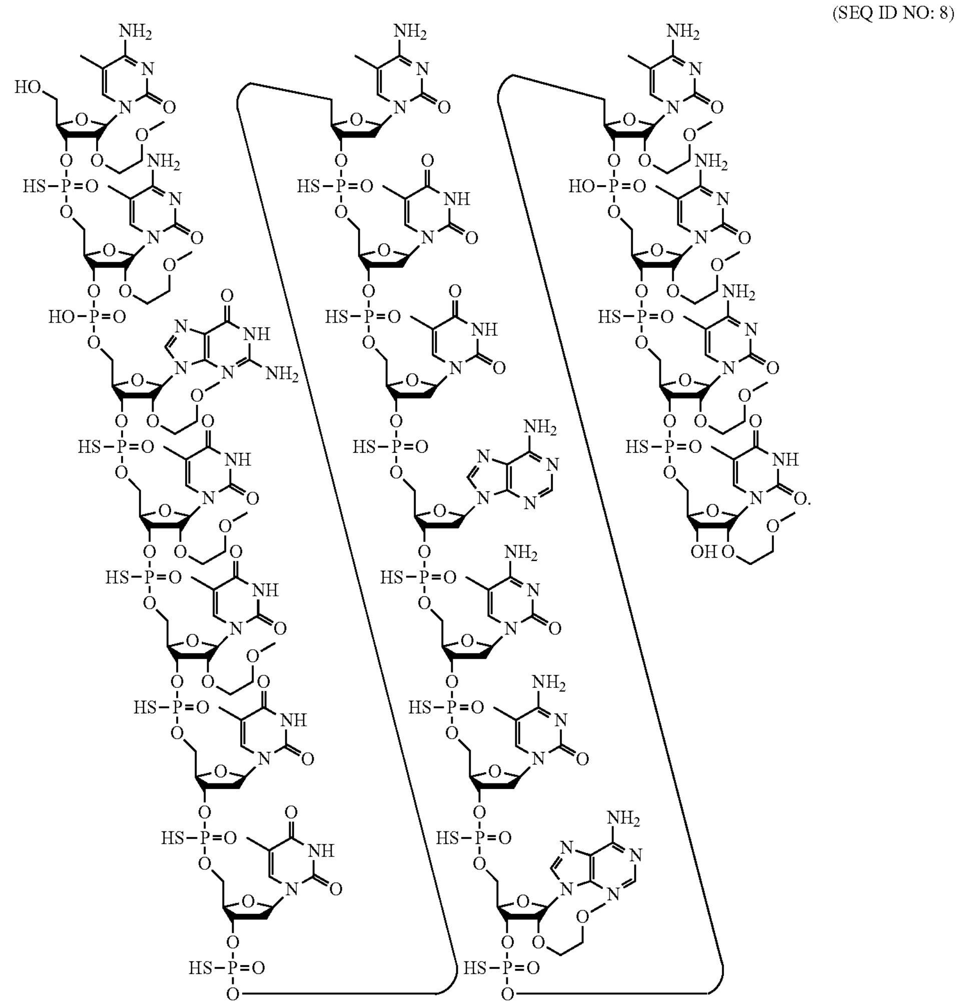

Structure 1. Compound No. 814907

VIII. Certain Benchmarks

In certain embodiments, Compound No. 623782 (characterized hereinbelow in Example 1), first described in WO 2015/010135, is a benchmark. Compound No. 623782 was a top performer among the compounds described in WO 2015/010135 in terms of potency, efficacy, and tolerability. Compound No. 623782 is provided as a benchmark to demonstrate the superior efficacy and tolerability of Compound No. 814907 (characterized hereinbelow in Example 1) as compared to Compound No. 623782 in comparative studies described hereinbelow in Example 1 and Example 2.

As demonstrated in Example 1, Compound No. 814907 achieved an $ED_{50}$ of 25 μg in Tau transgenic mice treated with 30 μg, 100 μg, 500 μg, whereas Compound No. 623782 achieved an $ED_{50}$ of 94 μg in Tau transgenic mice treated with 10 μg, 30 μg, 100 μg, 300 μg, 700 μg. Thus, Compound No. 814907 is more efficacious than Compound No. 623782.

As demonstrated in Example 2, administration of Compound No. 814907 to wild-type mice resulted in no Purkinje cell loss, whereas administration of Compound No. 623782 resulted in Purkinje cell loss in calbindin stained cerebellum sections in 3 of 11 animals. Therefore, Compound No. 814907 is more tolerable than Compound No. 623782.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^{m}$CGAUCG," wherein $^{m}$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, oligomeric compounds and modified oligonucleotides described herein are intended to include corresponding salt forms. The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}H$ hydrogen atoms. Isotopic substitutions encompassed by the compounds herein include but are not limited to: $^{2}H$ or $^{3}H$ in place of $^{1}H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effects of Modified Oligonucleotides on Human Tau mRNA in Transgenic Mice The modified oligonucleotides shown in the table below are 100% complementary to human Tau pre-mRNA (GENBANK Accession No. NT_010783.14, truncated from nucleotides 2624000 to 2761000, designated herein as SEQ ID NO: 1). The efficacies of the modified oligonucleotides were tested in human Tau transgenic mice (Duff et al., Neurobiology of Disease 7:87-98, 2000). Each mouse received a dose of a modified oligonucleotide listed in the table below, or PBS vehicle only, by ICV bolus injection. Each treatment group consisted of 2 to 4 mice. Several days after oligonucleotide administration, the mice were sacrificed and tissues were collected. RNA was extracted from the cortex and analyzed by RT-qPCR in order to determine human Tau mRNA levels. Primer probe set RTS3104, with the following sequences, was used: forward primer 5'-AAGATTGGGTCCCTGGACAAT-3', designated herein as SEQ ID NO: 5; reverse primer 5'-AGCTTGTGGGTTTCAATCTTTTTATT-3', designated herein as SEQ ID NO: 6; probe 5'-CACCCACGTCCCTGGCGGA-3', designated herein as SEQ ID NO: 7. Results are presented in the table below as the average percent inhibition of human Tau mRNA expression for each treatment group compared to the vehicle treated group. The half maximal effective dose ($ED_{50}$) for each modified oligonucleotide was calculated using nonlinear regression analysis.

TABLE 1

Percent inhibition of human Tau mRNA levels in hTau mice

| Compound No. | Sequence | Dose (μg) | Human Tau mRNA (% inhibition) | $ED_{50}$ (μg) | SEQ ID NO. |
|---|---|---|---|---|---|
| 623782 | $^{m}C_{es}{}^{m}C_{eo}G_{eo}T_{eo}T_{es}T_{ds}T_{ds}{}^{m}C_{ds}T_{ds}T_{ds}A_{ds}{}^{m}C_{ds}{}^{m}C_{ds}A_{eo}{}^{m}C_{eo}{}^{m}C_{es}{}^{m}C_{es}T_{e}$ | 10 | 10 | 94 | 8 |
| | | 30 | 17 | | |
| | | 100 | 54 | | |
| | | 300 | 79 | | |
| | | 700 | 90 | | |
| 814907 | $^{m}C_{es}{}^{m}C_{eo}G_{es}T_{es}T_{es}T_{ds}T_{ds}{}^{m}C_{ds}T_{ds}T_{ds}A_{ds}{}^{m}C_{ds}{}^{m}C_{ds}A_{es}{}^{m}C_{eo}{}^{m}C_{es}{}^{m}C_{es}T_{e}$ | 30 | 48 | 25 | 8 |
| | | 100 | 79 | | |
| | | 500 | 88 | | |

Subscripts: "e" represents a 2'-MOE nucleoside; "d" represents a 2'-deoxynucleoside; "o" represents a phosphodiester internucleoside linkage; and "s" represents a phosphorothioate internucleoside linkage.
Superscript "m" preceding a "C" indicates that the cytosine is a 5-methylcytosine.

Example 2: Tolerability of Modified Oligonucleotides Targeting Human Tau

The tolerability of the modified oligonucleotides described in Example 1 was tested in wild type mice. Each mouse received a 700 μg injection of Compound No. 623782 or Compound No. 814907 at 700 μg dose, or PBS vehicle alone. Eight weeks after the modified oligonucleotide administration, the mice were sacrificed, and tissues were collected. Histopathology was performed on sections of cerebellum using H&E, IBA1, GFAP, and calbindin stains, and no abnormality relative to vehicle treated mice was observed for Compound No. 814907 treated mice. In a comparable experiment, Purkinje cell loss was observed in calbindin stained cerebellum sections in 3 of 11 animals treated with Compound No. 623782.

Example 3: Effect of Compound No. 814907 in Cynomolgous Monkey Following Repeat-Dose Intrathecal Injection for 13-Weeks Cynomolgus monkeys were treated with Compound No. 814907 to determine the local and systemic tolerability and pharmacokinetics at three dose levels, following repeat intrathecal lumbar bolus injections for 13 weeks. Compound No. 814907 shares complete sequence homology to the monkey Tau mRNA and has demonstrated pharmacologic activity in this species.

Treatment

Cynomolgus monkeys ranging in age from 2-4 years were treated vehicle control (n=12) or Compound No. 814907 intrathecally (between L3-L4). Animals were dosed on Days 1, 14, 28, 56, and 84. Treatment groups received 4 mg (n=6), 12 mg (n=6), or 35 mg (n=14) of Compound No. 814907. Animals were sacrificed either on day 98 or 155 (4 animals from the vehicle control group and 4 animals from the 35 mg treatment group).

Tolerability

Assessment of tolerability was based on clinical observations, body weights, food consumption, physical and neurological examinations, neurobehavioral observations (modified Irwin test (Irwin, 1968)), electrocardiogram (ECG) and blood pressure evaluation, ophthalmology, coagulation, hematology, clinical chemistry (blood and cerebral spinal fluid [CSF]), cell count (CSF only), blood gas evaluation, urine analysis, and anatomic pathology evaluations. Complete necropsies were performed with a recording of any macroscopic abnormality. Organ weights were taken and microscopic examinations were conducted. Blood was collected for complement analysis. In addition, blood, CSF, and tissues (at necropsy) were collected for toxicokinetic evaluations.

Intrathecal administration of 4 mg, 12 mg, or 35 mg Compound No. 814907 for 13 weeks (bi-weekly for the first month, then monthly thereafter) showed good local and systemic tolerability in male and female cynomolgus monkeys at all tested dosing regimens.

Activity

Brain and spinal cord tissue was analyzed for inhibition of cynomolgous monkey Tau mRNA. Brain slices and spinal cord samples were collected and flash frozen in liquid nitrogen and stored frozen (−60° C. to −90° C.). At time of sampling, 2 mm biopsy punches were used to collect samples for RNA analysis from the frozen brain slices. Punches were taken from multiple spinal cord and brain regions.

Total RNA from brain and spinal cord samples from cynomolgous monkeys treated with control or Compound No. 814907 were purified using a Life Technologies mini-RNA purification kit and subjected to real time PCR analysis. Monkey primer probe set rhMATPT LTS01278 (forward sequence AGGACAGAGTGCAGTCGAAGATC, designated herein as SEQ ID NO: 9; reverse sequence AGGTCAGCTTGTGGGTTTCAA, designated herein as SEQ ID NO: 10; probe sequence CACCCATGTCCCTGGCGGAGG, designated herein as SEQ ID NO: 11) was used to measure RNA levels. Tau RNA was then normalized to the housekeeping gene Cyclophilin A. All qPCR reactions were run in triplicate. Data is reported relative to mRNA levels in animals treated with artificial CSF.

As shown in the Table below, there was a significant and dose responsive decrease in Tau RNA levels in spinal cord and multiple CNS regions after treatment with Compound No. 814907, as compared to control treated monkeys.

TABLE 2

Percent inhibition of cynomolgous Tau mRNA levels in cynomolgus monkeys

| | Brain Regions | | | | | | |
|---|---|---|---|---|---|---|---|
| Treatment | Thoracic Spinal Cord | Lumbar Spinal Cord | Cortical Spinal Cord | Frontal Cortex | Temporal Cortex | Hippocampus | Pons |
| aCSF | 0 | 0 | 0 | 0 | 0 | 0 | 0 |
| 4 mg 814907 | 51 | 63 | 31 | 41 | 29 | 18 | 29 |
| 12 mg 814907 | 60 | 60 | 47 | 60 | 56 | 52 | 43 |
| 35 mg 814907 | 58 | 71 | 60 | 77 | 70 | 74 | 66 |

Example 4: Phase I-IIa Human Clinical Trial with Compound No. 814907

Multiple ascending doses of Compound No. 814907 are evaluated in a randomized, double-blind, placebo-controlled study to evalulate the safety, tolerability, pharmokinetics and pharmacodynamics in patients with mild Alzheimer's Disease (AD) aged 50-74 years of age. Eligible patients will have CSF AD biomarker evidence of amyloid and tau pathology in addition to meeting clinical criteria for AD. Four ascending dose level cohorts of mild AD patients will be enrolled sequentially and randomized 3:1 to receive Compound No. 814907 or placebo. Each patient will receive 4 doses of Compound No. 814907 or placebo with a 28 day interval between doses. Patients will receive 4 intrathecal (IT) bolus doses of Compound No 814907 at 4 week intervals during the 3 month treatment period (on Days 1, 29, 57, 85). Each dose of Compound No. 814907 or placebo will be administered as a single 20 mL IT bolus injection. Administration will be via lumbar puncture using a small gauge needle inserted into the L3/L4 space.

Safety and Tolerability Evaluations

Patient safety will be monitored closely during the study. Safety and tolerability evaluations include: physical examination and standard neurological assessment (including fundi), vital signs (HR, BP, orthostatic changes, weight), ECG, AEs and concomitant medications, Columbia Suicide Severity Rating Scale (C-SSRS), CSF safety labs (cell counts, protein, glucose), plasma laboratory tests (clinical chemistry, hematology), urinalysis, and neuroimaging assessments will be conducted using a 3T MRI scanner. Clinical and volumetric neuroimaging measures will be used to monitor for unexpected deterioration.

Pharmacokinetic Evaluations

A CSF sample will be collected pre-dose on each administration day (Days 1, 29, 57, 85) and during the post-treatment period for PK analyses.

Exploratory Evaluations

Biochemical, neuroimaging, functioning/ability to perform activities of daily living, cognitive, and neuropsychiatric parameters will be evaluated.

Biochemical parameters include potential CSF and blood/plasma biomarkers, including target engagement, neuronal and synaptic injury markers, innate immune activation markers, complement components, and lipid-related biomarkers.

Neuroimaging paramers include structural MRI (hippocampal, whole brain, and ventricular volumes), Arterial Spin Labelling (ASL), diffusion tensor imaging (DTI), and FDG-PET (Cohorts C and D only).

Functioning/ability to perform activities of daily living parameters include evaluation by Functional Activities Questionnaire (FAQ).

Cognitive parameters include evaluation by Repeatable Battery for the Assessment of Neuropsychological Status (RBANS) and Mini-mental state examination (MMSE)

Neuropsychiatric parameters include evaluation by Neuropsychiatric Inventory—Questionnaire (NPI-Q).

The invention claimed is:

1. A method of reducing tau messenger ribonucleic acid (mRNA) expression in a human subject in need thereof, the method comprising administering to the human subject a therapeutically effective amount of a modified oligonucleotide according to the following formula:

(SEQ ID NO: 8)

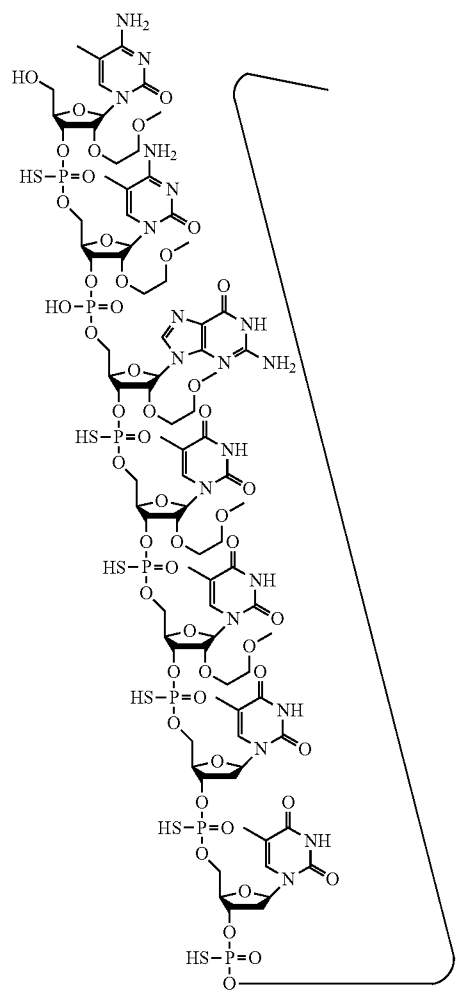

-continued

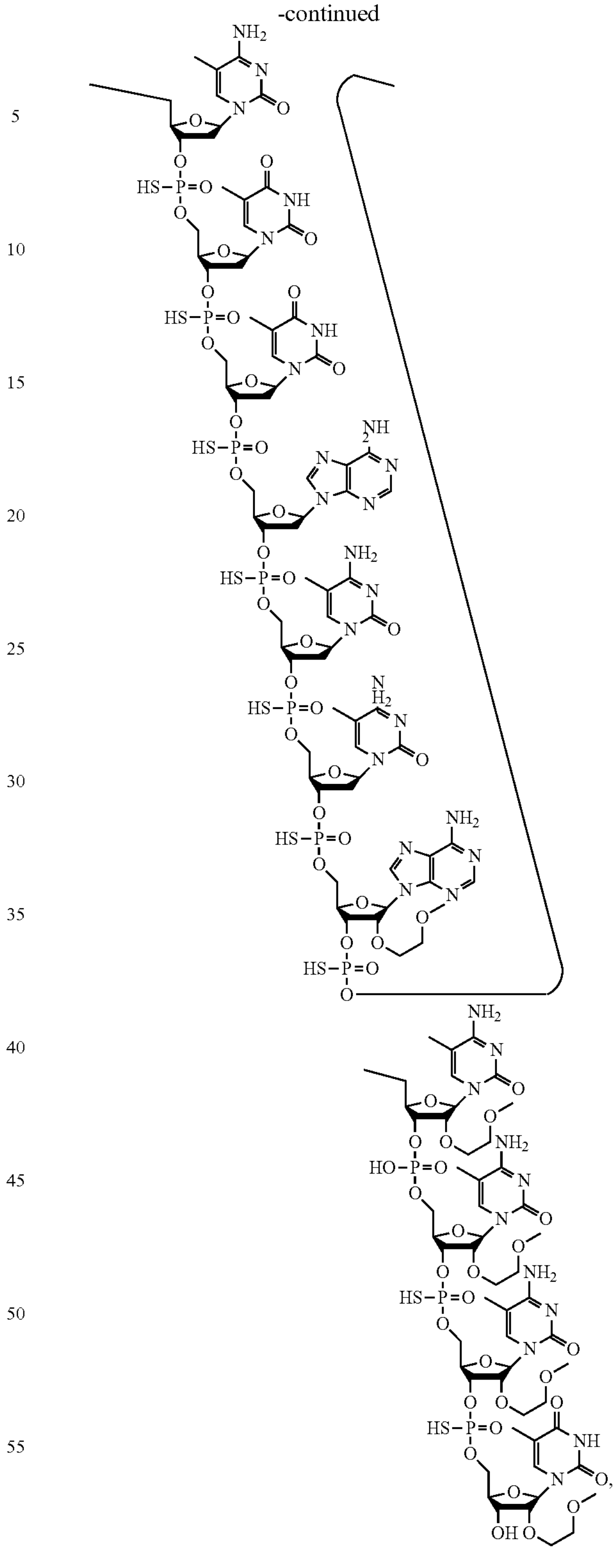

or a salt thereof.

2. The method of claim 1, wherein the salt is a sodium salt.

3. The method of claim 1, wherein the modified oligonucleotide or salt thereof is administered intrathecally.

4. The method of claim 2, wherein the modified oligonucleotide or salt thereof is administered intrathecally.

5. A method of reducing tau messenger ribonucleic acid (mRNA) expression in a human subject in need thereof, the method comprising administering to the human subject a therapeutically effective amount of a compound comprising a modified oligonucleotide, wherein the modified oligonucleotide is a gapmer consisting of a 5' wing segment, a central gap segment, and a 3' wing segment, wherein:

the 5' wing segment consists of five 2'-MOE nucleosides, the central gap segment consists of eight 2'-deoxynucleosides, and the 3' wing segment consists of five 2'-MOE nucleosides;

wherein the modified oligonucleotide has the nucleobase sequence 5'-CCGTTTTCTTACCACCCT-3' (SEQ ID NO: 8), wherein each cytosine is a 5-methylcytosine; and wherein the internucleoside linkages of the modified oligonucleotide are, from 5' to 3', sosssssssssssssoss, wherein each s is a phosphorothioate linkage and each o is a phosphodiester linkage.

6. The method of claim 5, wherein the compound is administered intrathecally.

7. A method of reducing tau messenger ribonucleic acid (mRNA) expression in a human subject in need thereof, the method comprising administering to the human subject a therapeutically effective amount of a modified oligonucleotide, wherein the modified oligonucleotide is a gapmer consisting of a 5' wing segment, a central gap segment, and a 3' wing segment, wherein:

the 5' wing segment consists of five 2'-MOE nucleosides, the central gap segment consists of eight 2'-deoxynucleosides, and the 3' wing segment consists of five 2'-MOE nucleosides;

wherein the modified oligonucleotide has the nucleobase sequence 5'-CCGTTTTCTTACCACCCT-3' (SEQ ID NO: 8), wherein each cytosine is a 5-methylcytosine; and wherein the internucleoside linkages of the modified oligonucleotide are, from 5' to 3', sosssssssssssssoss, wherein each s is a phosphorothioate linkage and each o is a phosphodiester linkage.

8. The method of claim 7, wherein the modified oligonucleotide is administered intrathecally.

9. A method of treating a neurodegenerative disease associated with tau in a human subject in need thereof, the method comprising administering to the human subject a therapeutically effective amount of a modified oligonucleotide according to the following formula:

(SEQ ID NO: 8)

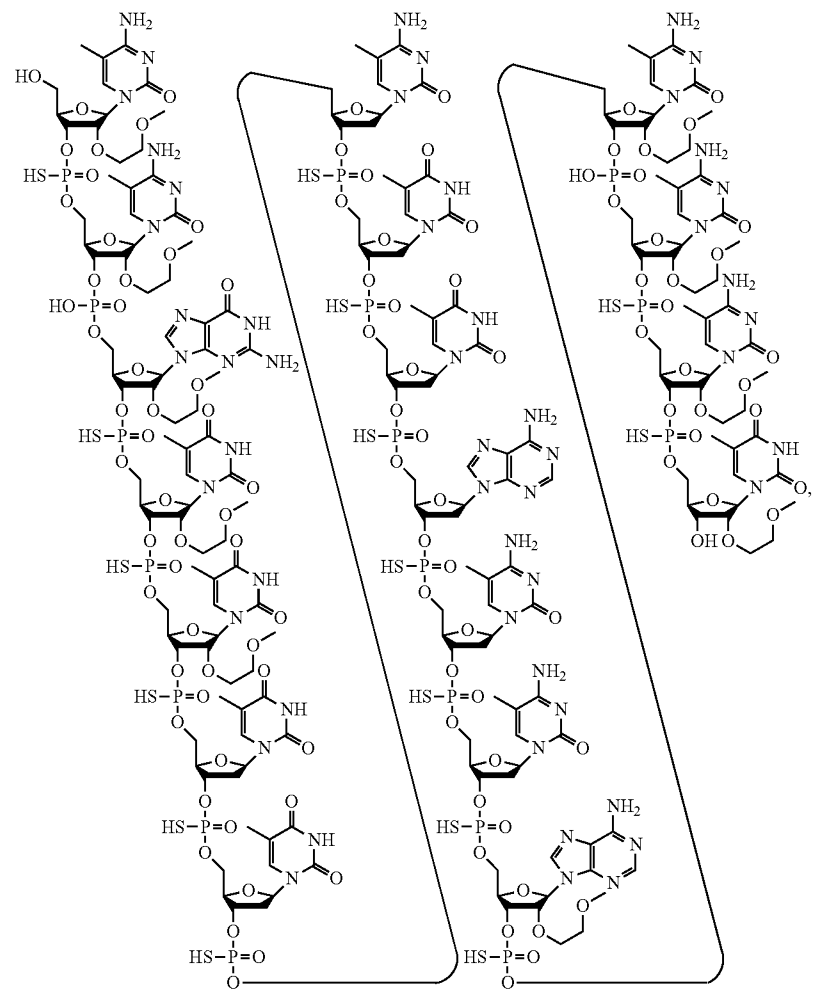

or a salt thereof.

10. The method of claim 9, wherein the salt is a sodium salt.

11. The method of claim 9, wherein the neurodegenerative disease is a tauopathy.

12. The method of claim 9, wherein the neurodegenerative disease is Alzheimer's disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

13. The method of claim 9, wherein the neurodegenerative disease is Alzheimer's disease.

14. The method of claim 9, wherein the modified oligonucleotide or salt thereof is administered intrathecally.

15. The method of claim 10, wherein the modified oligonucleotide or salt thereof is administered intrathecally.

16. The method of claim 11, wherein the modified oligonucleotide or salt thereof is administered intrathecally.

17. The method of claim 12, wherein the modified oligonucleotide or salt thereof is administered intrathecally.

18. The method of claim 13, wherein the modified oligonucleotide or salt thereof is administered intrathecally.

19. A method of treating a neurodegenerative disease associated with tau in a human subject in need thereof, the method comprising administering to the human subject a therapeutically effective amount of a compound comprising a modified oligonucleotide, wherein the modified oligonucleotide is a gapmer consisting of a 5' wing segment, a central gap segment, and a 3' wing segment, wherein:

the 5' wing segment consists of five 2'-MOE nucleosides, the central gap segment consists of eight 2'-deoxynucleosides, and the 3' wing segment consists of five 2'-MOE nucleosides;

wherein the modified oligonucleotide has the nucleobase sequence 5'-CCGTTTTCTTACCACCCT-3' (SEQ ID NO: 8), wherein each cytosine is a 5-methylcytosine; and wherein the internucleoside linkages of the modified oligonucleotide are, from 5' to 3', sosssssssssssssoss, wherein each s is a phosphorothioate linkage and each o is a phosphodiester linkage.

20. The method of claim 19, wherein the neurodegenerative disease is a tauopathy.

21. The method of claim 19, wherein the neurodegenerative disease is Alzheimer's disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

22. The method of claim 19, wherein the neurodegenerative disease is Alzheimer's disease.

23. The method of claim 19, wherein the compound is administered intrathecally.

24. The method of claim 20, wherein the compound is administered intrathecally.

25. The method of claim 21, wherein the compound is administered intrathecally.

26. The method of claim 22, wherein the compound is administered intrathecally.

27. A method of treating a neurodegenerative disease associated with tau in a human subject in need thereof, the method comprising administering to the human subject a therapeutically effective amount of a modified oligonucleotide, wherein the modified oligonucleotide is a gapmer consisting of a 5' wing segment, a central gap segment, and a 3' wing segment, wherein:

the 5' wing segment consists of five 2'-MOE nucleosides, the central gap segment consists of eight 2'-deoxynucleosides, and the 3' wing segment consists of five 2'-MOE nucleosides;

wherein the modified oligonucleotide has the nucleobase sequence 5'-CCGTTTTCTTACCACCCT-3' (SEQ ID NO: 8), wherein each cytosine is a 5-methylcytosine; and wherein the internucleoside linkages of the modified oligonucleotide are, from 5' to 3', sosssssssssssssoss, wherein each s is a phosphorothioate linkage and each o is a phosphodiester linkage.

28. The method of claim 27, wherein the neurodegenerative disease is a tauopathy.

29. The method of claim 27, wherein the neurodegenerative disease is Alzheimer's disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

30. The method of claim 27, wherein the neurodegenerative disease is Alzheimer's disease.

31. The method of claim 27, wherein the modified oligonucleotide is administered intrathecally.

32. The method of claim 28, wherein the modified oligonucleotide is administered intrathecally.

33. The method of claim 29, wherein the modified oligonucleotide is administered intrathecally.

34. The method of claim 30, wherein the modified oligonucleotide is administered intrathecally.

35. The method of claim 1, wherein the salt is a potassium salt.

36. The method of claim 35, wherein the modified oligonucleotide or salt thereof is administered intrathecally.

37. The method of claim 9, wherein the salt is a potassium salt.

38. The method of claim 37, wherein the modified oligonucleotide or salt thereof is administered intrathecally.

* * * * *